(12) United States Patent
Tsai et al.

(10) Patent No.: US 7,718,366 B2
(45) Date of Patent: May 18, 2010

(54) METHODS AND COMPOSITIONS RELATING TO COL2A1 GENE MUTATIONS AND OSTEONECROSIS

(75) Inventors: Shih-Feng Tsai, Miaoli County (TW); Yu-Fen Liu, Taipei (TW); Wei-Ming Chen, Taipei (TW)

(73) Assignee: National Health Research Institutes, Jhunan Township, Miaoli County (TW)

( * ) Notice: Subject to any disclaimer, the term of this patent is extended or adjusted under 35 U.S.C. 154(b) by 382 days.

(21) Appl. No.: 11/202,057

(22) Filed: Aug. 12, 2005

(65) Prior Publication Data

US 2006/0051794 A1 Mar. 9, 2006

Related U.S. Application Data

(60) Provisional application No. 60/602,319, filed on Aug. 18, 2004.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ............... 435/6; 435/91.2; 536/23.1; 536/24.33

(58) Field of Classification Search ............... None
See application file for complete search history.

(56) References Cited

U.S. PATENT DOCUMENTS

| | | | |
|---|---|---|---|
| 5,558,988 | A | 9/1996 | Prockop et al. |
| 5,593,859 | A | 1/1997 | Prockop et al. |
| 5,663,482 | A | 9/1997 | Prockop et al. |
| 5,948,611 | A | 9/1999 | Prockop et al. |
| 6,448,470 | B1 | 9/2002 | Khillan |

OTHER PUBLICATIONS

Jüppner H. 'Functional properties of the PTH/PTHrP receptor.' Bone. Aug. 1995;17(2 Suppl):39S-42S.*
Hacker UT et al 'Lack of association between an interleukin-1 receptor antagonist gene polymorphism and ulcerative colitis.' Gut. May 1997;40(5):623-7.*
Parmley JL et al 'How do synonymous mutations affect fitness?' Bioessays. Jun. 2007;29(6):515-9.*
Aerssens J et al 'Lack of association between osteoarthritis of the hip and gene polymorphisms of VDR, COL1A1, and COL2A1 in postmenopausal women.'Arthritis Rheum. Nov. 1998;41(11):1946-50.*
Liu Y-F et al 'Type II collagen gene variants and inherited osteonecrosis of the femoral head.' N Engl J Med. Jun. 2, 2005;352(22):2294-301.*
Williams CJ et al 'Spondyloepiphyseal dysplasia and precocious osteoarthritis in a family with an Arg75→Cys mutation in the procollagen type II gene (COL2A1).' Hum Genet. Nov. 1993;92(5):499-505.*
GenBank GI:15149477 '*Homo sapiens* collagen, type II, alpha 1 (primary osteoarthritis, spondyloepiphyseal dysplasia, congenital) (COL2A1), transcript variant 1, mRNA'. Aug. 13, 2001, pp. 1-7.*
Ahmad et al., *Proc. Natl. Acad. Sci. U.S.A.* 88:6624-6627 (1991).
Assouline-Dayan et al., *Semin. Arthritis Rheum.* 32:94-124 (2002).
Bauer et al., *Clin. Exp. Dermatol.* 28:53-60 (2003).
Bonadio et al., *Proc. Natl. Acad. Sci. U.S.A.* 87:7145-49 (1990).
Bonaventure et al., *Biochem. J.* 307:823-830 (1995).
Chen et al., *Am. J. Hum. Genet.* 75:310-317 (2004).
Chen et al., *Nature Genet.* 32:670-675 (2002).
Culver et al., *Hum. Gene Ther.* 1:399-410 (1990).
de Crombrugghe et al., *J. Rheumatol.* 22:1 Supp. 43:140-142 (1995).
Duffy et al., *J. Arthroplasty* 16:140-144 (2001).
Glueck et al., *Clin. Orthop.* 386:19-33 (2001).
Glueck et al., *Clin.Orthop.* 334:43-56 (1997).
Harvey et al., *Am. J. Pathol.* 162:873-885 (2003).
Jones et al., *J. Rheumatol.* 30:783-791 (2003).
Kasid et al., *Proc. Natl. Acad. Sci. U.S.A.* 87:473-477 (1990).
Knoell et al., *Am. J. Health Syst. Pharm.* 55:899-904 (1998).
Li et al., *Genes Dev.* 9:2821-30 (1995).
Liu et al., *N. Engl. J. Med.* 352:2294-2301 (2005).
Mankin, *N. Engl. J. Med.* 326:1473-1479 (1992).
Mont et al., *J. Bone Joint Surg. Am.* 77:459-474 (1995).
Niyibizi et al., *Gene Ther.* 11:408-416 (2004).
Raymon et al., *Exp. Neurol.* 144:82-91 (1997).
Woodley et al., *Nature Med.* 10:693-695 (2004).

* cited by examiner

*Primary Examiner*—Stephen Kapushoc
(74) *Attorney, Agent, or Firm*—Finnegan, Henderson, Farabow, Garrett & Dunner, LLP

(57) ABSTRACT

Methods, compounds, and kits for the diagnosis or screening of osteonecrosis are described, and the development of animal models for COL2A1 function in osteonecrosis is put forth. Novel mutations in the COL2A1 gene are identified that are associated with avascular necrosis of the femoral head. Methods of treatment of osteonecrosis and avascular necrosis of the femoral head, including gene therapy approaches comprising introduction of COL2A1 nucleic acid are contemplated.

6 Claims, 7 Drawing Sheets

(1)
(2)
(3)

A

B

C

METHODS AND COMPOSITIONS RELATING TO COL2A1 GENE MUTATIONS AND OSTEONECROSIS

RELATED APPLICATIONS

This application claims the benefit of U.S. Provisional Application No. 60/602,319 filed Aug. 18, 2004, the contents of which are incorporated herein in their entirety.

BACKGROUND

Osteonecrosis, including avascular necrosis, is a relatively common disorder that has been associated with a wide range of conditions, affecting patients with a variety of risk factors. The majority of cases are secondary to trauma. However, for non-traumatic cases, there often remains a diagnostic challenge in defining the cause of bone death. Non-traumatic osteonecrosis has been associated with corticosteroid usage, alcoholism, infections, hyperbaric events, storage disorders, marrow infiltrating diseases, coagulation defects, and some autoimmune diseases. However, a large number of idiopathic cases of osteonecrosis have been described without an obvious associated risk factor. (Assouline-Dayan et al., *Semin. Arthritis Rheum.* 32(2):94-124 (2002)).

Avascular necrosis of the femoral head (ANFH) is a debilitating disease that usually leads to destruction of the hip joint in the third to fifth decade of life. The disease prevalence is unknown, but it has been estimated that 10,000-20,000 new cases per year are diagnosed in the United States. (Mankin, N. *Engl. J. Med.* 326:1473-1479 (1992); Mont et al., *J. Bone Joint Surg. Am.*, 77:459-474 (1995)) Nearly half the patients with ANF require hip replacement before 40 years of age. Despite continued improvement in the design and technique of hip arthroplasty, the durability of total hip arthroplasty in young and active patients remains poor. Furthermore, the failure rate of arthroplasties is around 30%, after an average of 10 years follow-up. (Duffy et al., *J. Arthroplasty*, 16:140-144 (2001))

It has been suggested that a common pathogenesis pathway of ANFH involves the interruption of blood circulation to the antero-lateral part of the femoral head, leading to ischemic insult and bone collapse. The disease is aggravated by mechanical disruption (e.g., trauma, hip fracture), external pressure on or damage to a vessel wall (e.g., vasculitis, radiation therapy, systemic lupus erythematosus), arterial thrombosis or embolism (e.g., sickle cell disease, corticosteroid use, alcohol abuse) and venous or blood outflow occlusion (e.g., infection). Cases of ANFH that were initially considered idiopathic have been associated with heritable thrombophilia (an increased tendency for intravascular thrombosis) or hyperfibrinolysis (a reduced ability to lyse thrombi). (Glueck et al., *Clin. Orthop.*, 43-56 (1997); Glueck et al., *Clin. Orthop*, 19-33 (2001); Jones et al., *J. Rheumatol.* 30:783 (2003)). Although many ANFH cases are associated with known underlying risk factors and classified as secondary ANFH, 15-30% of patients showing no apparent risk factors are classified as primary or idiopathic avascular necrosis of the femoral head (idiopathic ANFH). (Assouline-Dayan et al., *Semin. Arthritis Rheum.* 32:94-124 (2002)).

Accordingly, early detection of osteonecrosis is important for surgical and other medical treatment options because a patient's prognosis may depend on the stage and location of the lesion. If the development of osteonecrosis can be detected early, corrective surgery or alternative therapy can be effectively carried out with more successful prognosis. Further, the development of additional treatment options for subjects with ANFH or osteonecrosis is desirable, including gene therapy and cell therapy approaches.

SUMMARY

Methods of the invention may be used in the diagnosis, screening, or development of animal models of osteonecrosis. The methods may also be used for detecting a genetic predisposition to osteonecrosis, including avascular necrosis of the femoral head.

Methods are provided for the comparison of a nucleotide sequence of a region of COL2A1 of an individual to be tested to the corresponding region of a standard DNA sequence of COL2A1, whereby a difference in the test sample as compared with the standard sequence indicates an increased likelihood of osteonecrosis.

The methods of the invention make it possible to detect mutations in the collagen gene in persons not otherwise known to have a risk factor for osteonecrosis. For example, prior to undergoing steroid treatment, a patient may be screened to identify a risk of developing ANFH with the methods provided.

Accordingly, the methods provided herein are also useful for detecting genetic familial predisposition to osteonecrosis or avascular necrosis of the femoral head. In methods of the invention, the location of a mutation in the COL2A1 gene of a first family member known or suspected of having osteonecrosis is determined. The nucleotide sequence of at least the mutated region is then compared to the corresponding region of the COL2A1 gene of a second family member, whereby the presence in the second family member of the mutated region indicates an increased likelihood of bone necrosis in the second family member.

Additionally, the methods of the invention may be used to provide models for the study of ANFH, such animal models, or in vitro models. These models would facilitate the development of treatments to slow the progression of the disease, or the development of drugs to prevent ANFH in patients undergoing steroid therapy.

Nucleic acids encoding type II procollagen or collagen are provided herein, as are polypeptides encoded by certain mutant COL2A1 nucleic acids associated with osteonecrosis. In some embodiments, the mutation associated with the necrosis is in a region of COL2A1 nucleic acid encoding a G-X-Y region of polypeptide. The mutation associated with necrosis may be in exon 33 or 50 of the COL2A1 nucleic acid encoding a G-X-Y domain. In further embodiments, the mutation causes a substitution of a conserved glycine residue in a G-X-Y region of a polypeptide encoded by COL2A1, in some instances with a serine residue.

Methods of treating osteonecrosis or ANFH in a subject, including in vivo or ex vivo gene therapy techniques are provided herein. Exemplary methods comprise introducing nucleic acid to a cell to inhibit or suppress mutant COL2A1 activity, to supplement wild-type COL2A1 activity, and/or to replace endogenous COL2A1 nucleic acid. Ex vivo techniques comprising excising cells or tissues from a individual, introducing a nucleic acid comprising a COL2A1 nucleic acid into the excised cells or tissues, and reimplanting the cells or tissues into the subject.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

FIG. 2 depicts COL2A1 mutations in ANFH families.

FIG. 3 shows the disease phenotype in ANFH patients.

BRIEF DESCRIPTION OF THE SEQUENCES

Figure 1A:
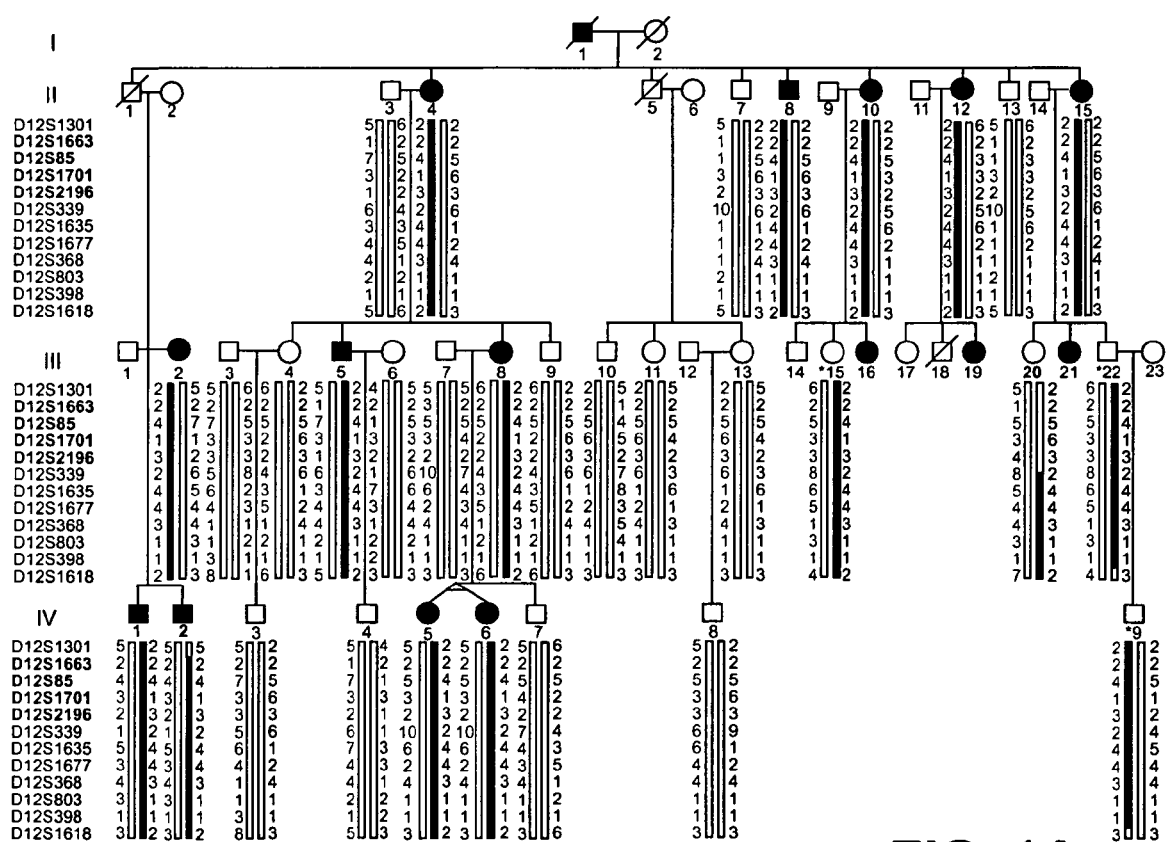
FIG. 1A depicts a pedigree and haplotype analysis of ANFH family A, and 1B depicts a similar analysis of family B. Short Tandem Repeat (STR) markers spanning the ANFH candidate region of chromosome 12 were used to construct the haplotype. A graphical depiction of individuals from family A, their family relations, and the relevant chromosome with STR markers is presented. Symptomatic individuals are depicted with a black square or circle, and asymptomatic or undiagnosed individuals are shown with white symbols. In the pedigrees, each individual is assigned a unique identifier, with roman numerals identifying the generation, and numbers identifying the individual within the generation. Data of family members III:20 and IV:2 identify recombination breakpoints and define a critical region of chromosome 12, narrowing it to a 8.2 cM interval between D12S1301 and D12S339. The STR markers that identify recombination breakpoints and define a critical region are shown in grey. The disease-associated haplotype of family A, defined by markers between D12S1663 and D12S2196, is different from family B.

The following table is provided as a reference for the sequences referred to in this application.

TABLE 1

| Reference | Type* | Sequence |
| --- | --- | --- |
| SEQ ID NO: 1 | DNA | COL2A1 genomic DNA |
| SEQ ID NO: 2 | DNA | COL2A1 cDNA |
| SEQ ID NO: 3 | AA | COL2A1 amino acid sequence |
| SEQ ID NO: 4 | DNA | G1170S variant COL2A1 cDNA (G –> A at nt 3665) |
| SEQ ID NO: 5 | AA | G1170S COL2A1 aa sequence |
| SEQ ID NO: 6 | DNA | G717S variant COL2A1 cDNA (G –> A at nt 2306) |
| SEQ ID NO: 7 | AA | G717S COL2A1 aa sequence |
| SEQ ID NOS: 8-28 | AA | COL2A1 polypeptide regions (Table 3) |
| SEQ ID NO: 29 | DNA | Exon 33, nt 2252-2350 of SEQ ID NO: 2 |
| SEQ ID NO: 30 | AA | Exon 33, aa 699-728 of SEQ ID NO: 3 |
| SEQ ID NO: 31 | DNA | Exon 50, nt 3647-3754 of SEQ ID NO: 2 |
| SEQ ID NO: 32 | AA | Exon 50, aa 1164-1193 of SEQ ID NO: 3 |
| SEQ ID NOS: 33-110 | DNA | primers/probes relating to COL2A1 (Table 2) |

DETAILED DESCRIPTION

This invention is based in part on the discovery of genetic mutations associated with osteonecrosis observed in three families that show an autosomal dominant mode of inheritance of ANFH. In family A, 16 affected individuals, including two monozygotic twin sisters, were noted among 75 family members. Unexpectedly, three genes associated with thrombophilia and hypofibrinolysis are not associated with idiopathic ANFH in the families. Instead novel mutations in the type II procollagen gene are associated with ANFH. Whereas prior mutations in the COL2A1 gene have been implicated in cartilage defects including various forms of chondrodysplasia or osteoarthritis, we herein report a novel pathology associated with mutations of COL2A1.

Mutations in the gene for type II procollagen and in the resulting procollagen and collagen nucleic acids and polypeptides are associated with development of avascular necrosis of the femoral head. In heritable forms, affected family members have the mutation in COL2A1 in the same location. Thus, if one family member develops an avascular necrosis, other family members may be at risk of developing bone disease. Asymptomatic relatives of the family member or other individuals can be screened to determine if they have the mutated gene and therefore are prone to develop an osteonecrotic disorder. Additionally, mutations in COL2A1, including the promoter are associated with sporadic forms of ANFH. SNPs from the COL2A1 gene identify genetic markers for ANFH or osteonecrosis.

Definitions

"Osteonecrosis" refers to a disease or disorder characterized by bone loss, bone and cell death, or defective bone maintenance or repair. One form of osteonecrosis is avascular necrosis of the bone, including avascular necrosis of the femoral head. In ANFH, hip joint tissue is affected. Necrosis of the bone may be detected in an individual with histopathological or radiographic methods, such as conventional or cross-sectional X-rays, magnetic resonance imaging, or other techniques known in the art. Idiopathic osteonecrosis of the femoral head is defined as a disease that causes ischemic osteonecrosis of the femoral head without trauma or sepsis according to the proposal of the Association Research Circulation Osseous (ARCO) committee put forth in 1993. Steroid-induced osteonecrosis and alcohol-associated osteonecrosis are also included in this disease category. The pathogenesis of osteonecrosis may involve vascular compromise, cell death, or deficient bone repair.

An individual having a predisposition or having a disorder may be "symptomatic" which refers to any morbid phenomenon or departure from the normal in structure, function, or sensation, experienced by a patent and indicative of the disorder. Symptoms of ANFH or osteonecrosis may include gradual or sudden onset with progressive pain in the groin, mechanical failure of the subcondral bone, degradation of the hip joint, death of cells in the cancellous bone, and poor blood supply to an area of bone causing ischemia, bone collapse, and/or bone death. The methods described herein may be applied to pre-symptomatic, asymptomatic, and symptomatic individuals. ANFH symptoms may be unilateral or bilateral, affecting one or both hip joints in an individual.

A polypeptide encoded by COL2A1 includes collagen or procollagen type II polypeptides from human, mammalian, or other sources, and may be found as collagen polymers in tissue matrices. Type II collagen or procollagen transcript variants and post-translational modifications are known in the art and include hydroxylation, glycosylation, and di-sulfide bond formation. The DNA or deoxyribonucleic acid sequences encoding COL2A1 polypeptides or fragments thereof can be genomic DNA or cDNA prepared from RNA. Accordingly, COL2A1 DNA may include regions of DNA that encode type II collagen, non-transcribed, and/or non-translated regions. Nucleic acids may be purified or derived from a sample of cells or tissues taken from an individual. Nucleic acid may also be extracted from bodily fluids containing lysed cells.

The term "individual," as used herein, denotes a mammal of any species, including humans and non-human animals. Preferably, the subject will be a mammal. Preferred mammals include primates such as humans, baboons, and chimpanzees, domestic animals such as horses, cows, pigs, dogs, and cats. The term "family member" is used to refer to individuals, including humans and other mammals, genetically related to one another in any degree, such as, for example, parent-child, siblings, cousins, grandparent, etc. Such genetic relatedness may be determined using standard methods known in the art, including, for example, pedigree analysis or DNA "fingerprinting."

A "fragment" of COL2A1 nucleic acid refers to a portion of the gene sequence encoding all or part of type II procollagen or of type II collagen. The nucleic acid may include a coding or non-coding sequence, including an exon, intron, promoter, enhancer, or other regulatory sequence. In one embodiment, the fragment of COL2A1 comprises a nucleic acid encoding a domain or region containing a G-X-Y repeat, triple helix repeat, or triplex-repeat portion of type II procollagen and collagen. In other embodiments, the fragment encodes only a portion of a G-X-Y domain. In still other embodiments, a fragment may be 12, 15, 25, 50, 75, 100, 125, 150, 200, 250, 300, 350, or more residues in length. Fragments of a polypeptide encoded by COL2A1 nucleic acid are similarly defined.

The primers and probes of the invention embrace oligonucleotides of sufficient length and appropriate sequence so as to provide initiation of polymerization on a significant number of nucleic acids and/or specific hybridization to a mutation of COL2A1 associated with osteonecrosis. Specifically, the term "primer" as used herein refers to a sequence comprising 5 or more deoxyribonucleotides or ribonucleotides, preferably more than 12 or 15, and most preferably at least 18, 19, 20, 21, 22, 23, 24, or 25 nucleotides of the COL2A1 gene. A primer or probe is preferably single stranded, but may be doubled stranded. If double stranded, the primer is first treated to separate its strands before being used to prepare extension products to detect a COL2A1 mutation. The exact length of the primer or probe will depend on many factors, including temperature, buffer, carrier, nucleic acid, and nucleotide composition.

The term "specific" used in relation to binding, reaction, or recognition refers to a situation in which one member of a specific binding pair will not show significant binding to molecules other than its specific binding partner(s). The term is also applicable where one member of a binding pair will show significant binding to at least some homologs of the other binding member. Typically, binding is considered specific if its affinity constant Ka is higher than $10^6 M^{-1}$, more preferably if it is higher than $10^7 M^{-1}$ or higher than $10^8 M^{-1}$. Specific binding conditions for nucleic acid and protein interaction are well known in the art, and a skilled artisan using routine techniques can select appropriate conditions. The conditions are usually defined in terms of concentration of the molecule of interest, ionic strength of the solution, temperature, time allowed for binding, concentration of non-related molecules (e.g. serum albumin, milk casein), etc.

The term "isolated" refers to a molecule that is substantially free of its natural environment. For instance, an isolated protein is substantially free of cellular material or other proteins from the cell or tissue source from which it is derived. Likewise, isolated nucleic acid is substantially free of other cellular material from the source from which it is derived. The term refers to preparations where an isolated protein or nucleic acid is at least 70% to 80% (w/w) pure, more preferably, at least 80% to 90% pure, even more preferably, 90-95% pure, and most preferably, at least 95%, 96%, 97%, 98%, 99% or 100% pure.

A "subject" refers to any person or non-human animal in need of a specific nucleic acid, protein, polypeptide, or peptide agent, or to any subject for whom treatment may be beneficial, including humans and non-human animals. Preferably, the subject will be a mammal. Preferred mammals include primates such as humans, baboons, and chimpanzees, domestic animals such as horses, cows, pigs, dogs, and cats. One of skill in the art will, of course, recognize that the choice of agent will depend on the disease or condition to be treated in a particular system.

An individual may be predicted to be "at risk of developing osteonecrosis" or "at risk of developing ANFH" by determining the presence or absence of genetic or environmental factors associated with a predisposition to develop the disorder. One or more genetic and/or environmental factors may cause a predisposition for developing osteonecrosis, including ANFH. Subjects may be asymptomatic or symptomatic; including those having a predisposition to develop osteonecrosis or ANFH. Environmental risk factors for osteonecrosis, including ANFH, include mechanical disruption, hip fracture, external pressure on or damage to a vessel wall, vasculitis, radiation therapy, systemic lupus erythematosus, arterial thrombosis or embolism, sickle-cell disease, corticosteroid use, and alcohol abuse.

The terms "therapeutic compound" and "therapeutic" refer to any compound capable of treating, reversing, ameliorating, halting, slowing progression of, or preventing clinical manifestations of a disorder, or of producing a desired biological outcome.

The terms "inhibit" and "suppress" refer to any decrease or reduction in COL2A1 gene transcription, COL2A1 gene translation, COL2A1 splicing, COL2A1 activity, or any other COL2A1-related activity. The terms encompass inhibition or suppression that results in weak, partial loss of COL2A1 function, strong, partial loss of COL2A1 function, and loss COL2A1 function. Further, symptoms of a COL2A1-related disorder such as osteonecrosis may be inhibited or suppressed as a therapeutic endpoint.

The term "stimulate" refers to any increase in COL2A1 gene transcription, COL2A1 gene translation, COL2A1 splicing, COL2A1 activity, or any other COL2A1-activity. The invention encompasses low levels of increase in COL2A1 activity, moderate levels of increase in COL2A1 activity, and high levels of increase in COL2A1 activity.

Methods of Detection, Diagnosis, or Screening

In one embodiment, individuals not otherwise known to have a necrotic disease or disorder are screened to detect mutations in the procollagen type II gene which would indicate an increased likelihood of developing osteonecrosis, or more particularly, avascular necrosis. Nucleic acid from a cell of an individual is isolated and the presence or absence of a mutation in a region of COL2A1 is detected by comparing the test DNA with a DNA standard, whereby the presence of the mutation indicates a genetic predisposition for osteonecrosis in the individual.

The DNA sequence and structure of the COL2A1 gene obtained from an individual may be compared to the normal gene sequence provided herein or to sequences known or available in computerized databanks. Any difference in the base sequence from the DNA of the individual tested as compared to the standard sequence is evaluated to determine whether it indicates an increased likelihood of the individual suffering from osteonecrosis or a related disorder. If an individual having a COL2A1 mutation associated with osteonecrosis is identified, family members who may be at risk of developing bone disease can be screened to determine if they have the mutated gene and therefore are prone to develop an osteonecrotic disorder.

Another embodiment provides that the mutation may be detected by examination of the nucleotide base sequence of a fragment of DNA of COL2A1. The DNA coding for the type II collagen chain can be genomic DNA or cDNA prepared from RNA.

In further embodiments, the mutation detected by the methods of the invention is an amino acid substitution of a glycine in a G-X-Y domain of type II collagen. Particularly, the mutation may cause a glycine to serine substitution at a position corresponding to position 717 of human type II procollagen. Alternatively, the mutation detected is a glycine to serine substitution at a position corresponding to position 1170 of type II procollagen. Still other embodiments provide a nucleic acid that encodes a collagen or procollagen polypeptide or polypeptide fragment that contains a mutation identified above.

Detection of the presence or absence of mutation may be accomplished by a variety of methods known in the art. For example, amplification of nucleic acid by polymerase chain reaction may be used to directly detect a mutation associated with osteonecrosis. Alternately, sequencing methods may provide the detailed base sequence that defines the mutation at the nucleotide level, or site-specific restriction endonucleases may differentiate mutations in the COL2A1 DNA. Mutations may also be detected using Southern blot or dot blot hybridization techniques. Other methods for detection of a mutation in a gene are well known in the art, and described, for example, in U.S. Pat. Nos. 5,266,459, 6,083,698, 6,248,518, 6,448,015, 6,492,109, 6,566,141, and 6,623,927.

Hybridization methods are provided which are intended to describe conditions for hybridizations and washes under which nucleotide sequences that are significantly identical or homologous to each other remain complementarily bound to each other. "Stringent" hybridization conditions are known in the art and can be found in Current Protocols in Molecular Biology, John Wiley & Sons, Inc. (1995), sections 2, 4, and 6.

Additionally, methods of partially denaturing gel electrophoresis can be used to detect the presence or absence of a mutation in a region of COL2A1. See, for example, U.S. Pat. No. 6,566,141. A nucleic acid may be directly or indirectly detected by any suitable method including radioisotope, fluorescent, bioluminescent, chemiluminescent, or chelating labels. Primers, probes, or fragments specific for hybridization to a mutation of COL2A1 associated with osteonecrosis, or designed for sequencing the same are herein provided. The sequences of primers for detecting mutations are listed in Table 2.

TABLE 2

| SEQ ID NO | Detected region | Primer Reference | and Sequence |
|---|---|---|---|
| 33 | Promoter | COL2A1-P1-1-F | GCGTCAGGCGTTTGGGAGT |
| 34 | | COL2A1-P1-1-R | GGGGCCGACTGGGAAATT |
| 35 | Promoter | COL2A1-P1-2-F | CCGCTGGGCTGTAACCTGA |
| 36 | | COL2A1-P1-2-R | ACCAGGTACTGCAGGGAAGG |
| 37 | Exon 1 | COL2A1-E1-P1-F | ACCCTGGGACAGAGTCCTTG |
| 38 | | COL2A1-E1-P1-R | TTCAGGTTACAGCCCAGCG |
| 39 | Exon 2 | COL2A1-E2-P1-F | AACTAGCCCCTCTGCTTTGC |
| 40 | | COL2A1-E2-P1-R | CAACATGGTGCAAGGTGCAT |

TABLE 2-continued

| SEQ ID NO | Detected region | Primer Reference | Sequence |
|---|---|---|---|
| 41 | Exon 3-Exon 7 | COL2A1-E3-E7-P1-F | AAGATGACAGCAAGGCCAGG |
| 42 | | COL2A1-E3-E7-P1-R | CGCCTTCCTTGATTGTGTCC |
| 43 | Exon 3-Exon 7 | COL2A1-E3-E7-P2-F | ACAGGCCTGAGGGCAAAGC |
| 44 | | COL2A1-E3-E7-P2-R | CGCGCAAGTTACTGATCTGC |
| 45 | Exon 8 | COL2A1-E8-P1-F | ATCTCCCCATCTTCATTC |
| 46 | | COL2A1-E8-P1-R | TTGCCACTGTCATCTAAT |
| 47 | Exon 9-Exon 10 | COL2A1-E9-E10-P1-F | TGGTCCTTGCCACATTGG |
| 48 | | COL2A1-E9-E10-P1-R | CCCCTTGCCCACAGAGTAAC |
| 49 | Exon 11 | COL2A1-E11-P1-F | TTCTCAATTTCCCTTCCTGG |
| 50 | | COL2A1-E11-P1-R | TGTCCTAACAGCCCCCTTTC |
| 51 | Exon 12-Exon 15 | COL2A1-E12-E15-P1-F | TTCCTGGGAAACCACGAGC |
| 52 | | COL2A1-E12-E15-P1-R | AAAGGCATGGAGGGCTGG |
| 53 | Exon 12-Exon 15 | COL2A1-E12-E15-P2-F | GCACAAGGTCAGTGTCTGGG |
| 54 | | COL2A1-E12-E15-P2-R | CAGGGCAGCTTTCCACTGTT |
| 55 | Exon 16 | COL2A1-E16-P1-F | AATCATGCTTTCACCCATCG |
| 56 | | COL2A1-E16-P1-R | ACTGCAAGGAGCAAGGTGTG |
| 57 | Exon 17 | COL2A1-E17-P1-F | GACTGCTGAAAGGATGGCTG |
| 58 | | COL2A1-E17-P1-R | CGACAGAGCCAGACTCCGTC |
| 59 | Exon 18 | COL2A1-E18-P1-F | CCTGCCAGGCCTATGGTGT |
| 60 | | COL2A1-E18-P1-R | CCTTCTGAAGCCAGGCAAAG |
| 61 | Exon 19-Exon 23 | COL2A1-E19-E23-P1-F | GATCCTTTGGCTCCAGGAA |
| 62 | | COL2A1-E19-E23-P1-R | AGGGTTGGGTGCATGTGC |
| 63 | Exon 19-Exon 23 | COL2A1-E19-E23-P2-F | GGCCTGTGCCTCATAGAACA |
| 64 | | COL2A1-E19-E23-P2-R | GGGGTTCATTCTTTGCTGCT |
| 65 | Exon 19-Exon 23 | COL2A1-E19-E23-P3-F | CCACAAGGACTCCACTTCCC |
| 66 | | COL2A1-E19-E23-P3-R | CCCAAGGGAGAACCTGTGAG |
| 67 | Exon 24-Exon 26 | COL2A1-E24-E26-P1-F | ACTTCAGGCCTCCCTAACCC |
| 68 | | COL2A1-E24-E26-P1-R | GTGGGTTAGTGGGATGGACC |
| 69 | Exon 27 | COL2A1-E27-P1-F | CTGGGCACTGCCACATGGA |
| 70 | | COL2A1-E27-P1-R | GGGGGAATGATGACATCGTG |
| 71 | Exon 28 | COL2A1-E28-P1-F | GCTGTTCTCAGCATGGAAGC |
| 72 | | COL2A1-E28-P1-R | GCAGTGGGGGTCTGTATGTG |
| 73 | Exon 29-Exon 33 | COL2A1-E29-E33-P1-F | GTCCAGGACATTCCCAGGCC |
| 74 | | COL2A1-E29-E33-P1-R | AAGACGCCTGTGCTGCCCAC |
| 75 | Exon 29-Exon 33 | COL2A1-E29-E33-P2-F | CCTGAGCCCGCTCCTCTTCT |
| 76 | | COL2A1-E29-E33-P2-R | GGCTCTTTGGACCTGCAACC |
| 77 | Exon 34 | COL2A1-E34-P1-F | GCTGTGGTCTCAGGGTGGGT |
| 78 | | COL2A1-E34-P1-R | TGGGAGTCCCACTGAGCAG |
| 79 | Exon 35-Exon 36 | COL2A1-E35-E36-P1-F | CCTTGGCCGAGGGTGACAGT |
| 80 | | COL2A1-E35-E36-P1-R | TGGGCAGGGACTGGGCTTT |
| 81 | Exon 37 | COL2A1-E37-P1-F | AGAGACGGGATCTGAAAGC |
| 82 | | COL2A1-E37-P1-R | GCAGTGTTCCCTGTTGGGTG |
| 83 | Exon 38-Exon 39 | COL2A1-E38-E39-P1-F | CAGGCCTGCGAACCATCCTC |
| 84 | | COL2A1-E38-E39-P1-R | AGAAGCAGGTCAGGCAGCGG |
| 85 | Exon 40 | COL2A1-E40-P1-F | CCCCGGGTCTGGTCATAGA |
| 86 | | COL2A1-E40-P1-R | CAAGTCTCCTGTGGCAGAGG |
| 87 | Exon 41 | COL2A1-E41-P1-F | TGTCCTGCCCACCAAGCCA |
| 88 | | COL2A1-E41-P1-R | ATTCCCCAGCCCGAGGCTT |
| 89 | Exon 42-Exon 44 | COL2A1-E42-E44-P1-F | CCAGGCAAGCCAGGGAAT |
| 90 | | COL2A1-E42-E44-P1-R | CCCCAGAGAGGAAACTGCTG |

TABLE 2-continued

| SEQ ID NO | Detected region | Primer Reference and Sequence | |
|---|---|---|---|
| 91 | Exon 42-Exon 44 | COL2A1-E42-E44-P2-F | TCTATGCCCGTCTCTCTCCC |
| 92 | | COL2A1-E42-E44-P2-R | TGGGCCACTGTCAGTTCTCA |
| 93 | Exon 45-Exon 49 | COL2A1-E45-E49-P1-F | TGAGCGCAGCGTCAGAGA |
| 94 | | COL2A1-E45-E49-P1-R | GTTGGGCAGAAGAGGAGAGG |
| 95 | Exon 45-Exon 49 | COL2A1-E45-E49-P2-F | CTCCAGCCCTGAGGAAATCC |
| 96 | | COL2A1-E45-E49-P2-R | GGGTTTCCGCAGTCTCTGG |
| 97 | Exon 45-Exon 49 | COL2A1-E45-E49-P3-F | TTTGGCCAAGAACCAGCAGG |
| 98 | | COL2A1-E45-E49-P3-R | ACTGCCTGCGTGGGACTTCC |
| 99 | Exon 50 | COL2A1-E50-P1-F | TTTCCCAGCACTGATCATGG |
| 100 | | COL2A1-E50-P1-R | GCCTCTCGCTGTCAGACAGA |
| 101 | Exon 51 | COL2A1-E51-P1-F | AAGAGAGGAACCCTCTGGCG |
| 102 | | COL2A1-E51-P1-R | TGGTCCTCGCCTGCTACA |
| 103 | Exon 52 | COL2A1-E52-P1-F | TGGAGCAAGCTCAGAGGACC |
| 104 | | COL2A1-E52-P1-R | CCTCCTTTCAGGCCACATG |
| 105 | Exon 53 | COL2A1-E53-P1-F | CCCTCAAACTCATGCCTCTG |
| 106 | | COL2A1-E53-P1-R | GCTCCACTCCTGGAAGCAAA |
| 107 | Exon 54 | COL2A1-E54-P1-F | TTTTGCAGTCTGCCCAGTTC |
| 108 | | COL2A1-E54-P1-R | CCTGCCGCTAAGGATAGGA |
| 109 | Exon 54 | COL2A1-E54-P2-F | GGACTGCTATTTGGGCATGC |
| 110 | | COL2A1-E54-P2-R | GCCGGTCTGCTTCTTGTAAA |

Oligonucleotides, including COL2A1 fragments such as primers or probes, may be prepared using any suitable method, such as conventional phosphotriester and phosphodiester methods or automated embodiments thereof. In one such automated embodiment, diethylphosphoramidites are used as starting materials and may be synthesized as described by Beaucage, et al., *Tetrahedron Letters* 22:1859-1862 (1981). One method for synthesizing oligonucleotides on a modified solid support is described in, e.g., U.S. Pat. No. 4,458,066.

Diagnostic Kits of the Invention

Further, the invention provides diagnostic kits comprising one or more COL2A1 specific primers or probes along with the required buffers and accessories suitable for identification of COL2A1 mutations associated with osteonecrosis. The invention further provides diagnostic kits comprising at least one or more allele-specific oligonucleotides as described in Table 2. Often, the kits in one or more pairs of allele-specific oligonucleotides hybridizing to different forms of a polymorphism. In some kits, the allele-specific oligonucleotides are provided immobilized to a substrate. For example, the same substrate can comprise allele-specific oligonucleotide probes for detecting at least one or all of the mutations described herein. Optional additional components of the kit include, for example, restriction enzymes, reverse transcriptase or polymerase, the substrate nucleoside triposphates, means used to label (for example, an avidinenzyme conjugate and enzyme substrate and chromogen if the label is biotin), and the appropriate buffers for reverse transcription, PCR, or hybridization reactions. A kit may be designed to detect the mRNA encoding a type II collagen protein in a biological sample. Such kits generally comprise at least one oligonucleotide probe or primer, as described above, that hybridizes to a polynucleotide encoding a type II collagen. Such an oligonucleotide may be used, for example, within a PCR or hybridization assay. Usually, a kit also contains instructions for use. An example of a kit using PCR detection of a mutation is found in U.S. Pat. No. 5,741,678.

Methods of Therapeutic Use

The present invention also provides for use of therapeutic compositions in carrying out the methods of the invention. An "effective amount" of the therapeutic composition refers to an amount sufficient to inhibit the expression of a polynucleotide in a patient. An "effective amount" also refers to an amount sufficient to reduce polynucleotide or protein activity, or to reduce or ameliorate symptoms. A reduction in symptom frequency or severity is a reduction in symptoms, for example by ameliorating symptoms of mild, moderate, or severe osteonecrosis. The compositions of the invention may also be used in appropriate association with other pharmaceutically active compounds. The following methods and excipients are merely exemplary and are not meant to be limiting.

The compositions may include, depending on the composition desired, physiologically acceptable, nontoxic carriers, which are defined as vehicles commonly used to formulate compositions for animal or human administration. In general, the carrier is also pharmacologically acceptable, i.e., it does not affect the biological activity of the combination. Examples of such carriers are distilled water, physiological phosphate-buffered saline, Ringer's solution, dextrose solution, and Hank's balanced salt solution. Also included may be carrier molecules such as proteoglycans. Specific examples of such carrier molecules include, but are not limited to, glycosaminoglycans such as heparin sulfate, hyaluronic acid, keratin-sulfate, chondroitin 4-sulfate, chondroitin 6-sulfate, heparin sulfate and dermatin sulfate, perlecan, and pento polysulfate. In addition, the composition may include other excipients, adjuvants, or nontoxic, nontherapeutic, nonimmunogenic stabilizers, and the like.

The composition of the invention may be formulated into preparations for injection by dissolving, suspending, or emulsifying the composition in a physiologically acceptable carrier. Carriers include sterile liquids, such as water, oils, with or without the addition of a surfactant, and glycols. Oils may be petroleum derivatives or of animal, vegetable, or synthetic origin, for example, peanut oil, soybean oil, and mineral oil. Examples of glycols include propylene glycol and polyethylene glycol. The compositions may also contain conventional additives such as solubilizers, isotonic agents, suspending agents, emulsifying agents, stabilizers, and preservatives. The composition of this invention may also be used in a sustained release form, for example, a depot injection, implant preparation, or osmotic pump, which can be formulated in such a manner as to permit a sustained release of the active ingredients.

The composition of the invention may be utilized in an aerosol composition to be administered via inhalation or pulmonary delivery. The composition of the present invention may be formulated into pressurized propellants such as dichlorodifluoromethane, nitrogen, and the like.

Administration of the composition of the invention may be accomplished by any convenient means, including parenteral injection, surgical introduction, and may be systemic or localized in delivery. Administration of the composition may be achieved in various ways, including oral, buccal, rectal, parenteral, intraperitoneal, intradermal, transdermal, intratracheal, intrathecal, intranasal, gastric, intramuscular, intracranial, subdermal, etc., administration. Local application of the therapeutic agent by injection (Wolff et al., 1990, Science, 247, 1465-1468), surgical implantation, instillation or any other means may be useful where effects are to be restricted to specific bones, cartilages or regions of bone or cartilage. This method may also be used in combination with local application by injection, surgical implantation, instillation or any other means of delivery to cells responsive to the therapeutic agent so as to increase the effectiveness of that treatment. The active agent(s) may be systemic after administration or may be localized by the use of regional administration, intramural administration, or use of an implant that acts to retain the active components at the site of implantation.

Those of skill in the art will readily appreciate that dose levels can vary as a function of the specific composition, the mode of administration or introduction, the severity of the symptoms, and the susceptibility of the subject to side effects. Additionally, some of the specific compositions of the invention may be more potent than others. Dosages for a given composition are readily determinable by those of skill in the art by a variety of means, for example by the gene delivery assays described below.

The present invention also relates to the treatment of a subject, or for the benefit of a subject, by administration of a nucleic acid vector or biological vector in an amount sufficient to direct the expression by the stimulation or inhibition or suppression of COL2A1 activity in a patient. Gene supplementation and gene replacement approaches are useful for treatment of COL2A1 mutations associated with ANFH and osteonecrosis. To treat a subject having osteonecrosis, including ANFH, in vivo and ex vivo approaches to gene therapy are contemplated.

Ex vivo gene therapy protocols may be adopted to treat subjects with autosomal dominant mutations in COL2A1 nucleic acids associated with osteonecrosis, including ANFH. Ex vivo gene therapy involves excising cells or tissues from a individual, such as stem cells, bone marrow-derived cells, mesenchymal stem cells, bone marrow-derived mesenchymal stem cells, or bone marrow stromal cells, for example, introducing the nucleic acid, nucleic acid vector or biological vector into the excised cells or tissues, and reimplanting the cells or tissues into the subject. Exemplary techniques are described in Knoell D. L., et al., (1998) *Am. J. Health Syst. Pharm.* 55:899-904; Raymon H. K., et al., (1997) *Exp. Neurol.* 144:82-91; Culver K. W., et al., (1990) *Hum. Gene Ther.* 1:399-410; Kasid A., et al., (1990) *Proc. Natl. Acad. Sci. U.S.A.* 87:473-477, which are incorporated by reference in their entirety. Similar techniques have been applied to the treatment of osteogenesis imperfecta, relating to type I collagen mutations (see, Niyibizi et al., 2004, Gene Therapy 11: 408-416.)

Bone regenerates with quiescent stem cells undergoing proliferation and differentiation. As cells turn over, cell therapy approaches allow the replacement of mutant osteoblasts or other differentiated cells with cells from transplanted progenitors. Treated progenitor cells may optionally be transplanted to a subject after treatment of the recipient's bone marrow, for example by irradiation, or as in a bone marrow transplantation procedures.

Administration of the nucleic acid vector or biological vector may provide the expression of a desired gene(s) that is deficient or non-functional in a subject. The nucleic acid vector or biological vector may be introduced into excised cells or tissues for ex vivo therapy by transfection, transformation, or infection, such as by the methods described above. The nucleic acid, nucleic acid vector, or biological vector may be directly introduced into a subject, for example, by intravenous or intramuscular injection, surgical implantation, or by aerosolization into the lungs.

Conventional gene transfer methods may be used to introduce DNA or RNA into target cells in vivo or ex vivo. Physical methods for the introduction of DNA into cells include microinjection and electroporation. Chemical methods such as co-precipitation with calcium phosphate and incorporation of DNA into liposomes are also standard methods of introducing DNA into mammalian cells. DNA may be introduced using standard vectors, such as those derived from, human, murine and avian retroviruses. Other viral vectors include adeno virus, adeno associated virus, and lenti virus (see, e.g., Gluzman et al., 1988, *Viral Vectors*, Cold Spring Harbor Laboratory, Cold Spring Harbor, N.Y.). Techniques for operably inserting genes into expression vectors are found in, for example, Sambrook et al., *Molecular Cloning: A Laboratory Manual*, 2nd Ed., Cold Spring Harbor Laboratory, Cold Spring Harbor, N.Y.; Ausubel et al. (Eds.), *Current Protocols in Molecular Biology*, John Wiley and Sons. Viral vectors for gene therapy have been developed and successfully used clinically (Rosenberg et al., 1990, *N. Engl. J. Med.* 323:370).

Methods of gene delivery to increase stability and/or specificity may be used, including viral vectors, retroviral vectors, liposome entrapped DNA systems, cationic amphiphilic compounds, PEGylation (see U.S. application Ser. No. 09/335,689 published as 20010048940), or antigen binding polypeptides (single chain or multivalent) that specifically bind nucleic acids via a basic amino acid region and target particular cells or cell-types (see U.S. Pat. No. 6,764,853). Optionally, one or more delivery procedures may be used to optimize treatment of a subject.

Methods of delivery are tested for efficacy and utility of a delivery system, including the use of marker genes. A marker gene such as that encoding β-galactosidase (β-gal), LacZ, chloramphenicol acetyl transferase (CAT), etc. is used for convenience to determine whether a protein can be expressed in a particular recombinant construct delivered by the present method and/or whether a nucleic acid is introduced to a cell, in vivo or ex vivo. In addition, marker genes allow the quantity and duration of expression to be assayed. The use of, for example, neomycin resistance to determine the efficacy of gene delivery has been described in human testing with the desired gene. PCR analysis similarly assays the presence of a nucleic acid, its expression, and its fate over time. Thus, the efficacy of delivery of a particular vector construct in a particular target tissue and host may be optimized.

In additional embodiments, the invention may include the use of nucleic acids to inhibit or suppress COL2A1 activity in a subject. Such gene suppression or gene silencing approaches may be useful for certain COL2A1 nucleic acid mutations, including autosomal dominant mutations. Approaches for inhibiting or suppressing COL2A1 activity to treat osteonecrosis include, but are not limited to, an antisense RNA or DNA molecule complimentary to the mRNA of the mutant protein, RNA ribozymes with regions designed to be complementary to the RNA of the mutant protein, double-stranded, small interfering RNAs (siRNAs) and their precursor dsRNA molecules, oligodeoxynucleotides, and a DNA or RNA molecule that promotes targeted trans-splicing of the RNA of the mutant protein (Niyibizi et al., 2004, Gene Therapy 11: 408-416; Bauer and Lanschuetzer, 2003, Clinical and Experimental Dermatology 28: 53-60). Gene suppression techniques create paired mRNA/DNA hybrids to selectively target the impaired or mutant COL2A1 nucleic acid for degradation by RNase, or paired mRNA/RNA hybrids that initiate degradation of the target mRNA, or a ribozyme that is specific for a mutant allele over the wild-type allele of COL2A1, for example (see, Niyibizi et al., 2004, Gene Therapy 11: 412-413).

Ribozymes can be used to achieve allele-specific suppression, differentiating between highly similar nucleic acid sequences. Ribozymes are short RNA molecules composed of a hairpin loop with two binding arms. The binding arms are designed to be complementary to the mutant RNA. Ribozymes, for example, from hammerhead, target the mutant RNA so that the catalytic core of the hairpin loop is opposite the cleavage site on the target mRNA. Using this approach, ribozymes directed against normal and mutated COL2A1 gene transcripts may be able to recognize and cleave specific targets even in the presence of high levels of nontarget RNA (Niyibizi et al., 2004, Gene Therapy 11: 408-416). Further, a mutation-independent strategy to suppress mutant alleles in which the ribozyme or other active nucleic acid targets a polymorphism associated with the COL2A1 gene that allows selective or differential suppression of the mutant form.

Another possible approach is to use double-stranded RNA (dsRNA) in a method sometimes referred to as RNA interference. In this approach, dsRNA for a specific target gene is delivered into cells. The dsRNA then. undergoes degradation, generating 21-25-nucleotide-long small interfering RNAs (siRNAs) which initiate degradation of target RNA. Direct delivery of double-stranded siRNAs or DNA constructs expressing a siRNA into mammalian cells can be effective in down-regulating specific gene expression (Niyibizi et al., 2004, Gene Therapy 11: 408-418; Caplem et al., 2001, Proc. Nat'l Acad. Sci USA, 98: 9742-9747).

Spliceosome-mediated RNA trans-splicing. (SMaRT) may also be used as a potential therapeutic method. SMaRT uses the introns preceding or following an exon harboring a mutation as a hinge to introduce a corrected species of RNA into a given premtRNA via a 3' trans-splicing reaction. This technique reduces the size of a corrective insert into a viral vector, which is of particular interest in genes coding for large proteins such as COL2A1 (Bauer and Lanschuetzer, 2003, Clinical and Experimental Dermatology 28: 56-58).

In yet another embodiment, the invention contemplates the administration by therapeutic methods, including gene therapy, of nucleic acids to inhibit or suppress mutant and/or COL2A1 activity in conjunction with supplementation of wild-type COL2A1 activity. Supplementation includes, but is not limited to, administration of a nucleic acid vector, biological vector, or COL2A1 polypeptide to increase wild-type COL2A1 activity. Gene replacement may be used as a supplement or in conjunction with gene therapy to inhibit or suppress mutant gene or protein activity. Alternatively, gene therapy may be performed using a mutation-independent approach by targeting polymorphic sites within procollagen genes in conjunction with collagen gene supplementation (Niyibizi et al., 2004, Gene Therapy 11: 412-413).

Animal Models: Mutant COL2A1 +/− and −/− Organisms

In one embodiment, the invention employs non-human organisms that are either heterozygous (+/−) or homozygous (−/−) for a COL2A1 mutation associated with osteonecrosis, or more particularly avascular necrosis of the femoral head. Such organisms may be made according to the methods of U.S. Pat. No. 6,448,470. A non-human transgenic organism allows the study of the type II collagen mutations identified in humans or non-human homologs of human COL2A1 DNA.

Mutations may be studied, for example, in the COL2A1 -null mice expressing human COL2A1 described in U.S. Pat. No. 6,448,470. Such null mutations in a COL2A1 homolog of the mouse gene, allow study of non-human vertebrate, preferably mammalian homologs. Those of skill in the art also appreciate that the methods of the invention can be employed with any vertebrate having such loss-of-function mutations; preferably, the methods of the invention employ a mammal.

Methods for inactivating collagen genes in an animal model by viral insertion or by knock-out of collagen genes or portions of collagen genes are known to one skilled in the art. (Bonadio et al., Proc. Natl. Acad. Sci. USA 87:7145-49; Li et al., Genes and Dev. 9:2821-30 (1995)). One skilled in the art would readily appreciate how to apply the methods and reagents of transgenic animal models for chondrodysplasia to the COL2A1 mutations associated with osteonecrosis herein described. Collagen multimerizes to form fibrils, and because the mouse collagen gene can multimerize with human collagen chains, heterozygous and homozygous mutant phenotypes will be useful for the study of osteonecrosis. COL2A1 heterozygous mice may be generated by homologous recombination and mated to produce double mutant mice using methods known in the art. Similar mutation phenotypes may occur naturally or can be induced by other means, and the invention encompasses the use of COL2A1 mutation +/− and/or COL2A1 −/− organisms, regardless of how the mutations originated.

Transgenic lines of mice may be prepared by any suitable method. In a preferred embodiment, a DNA sequence comprising a COL2A1 mutation of the invention is microinjected into mouse embryos. Transgenic lines are then established from the founder mice.

Transgenic lines of mice are prepared by microinjecting a genomic clone of the COL2A1 gene by suitable methods, such as injection into the cavity of a blastocyst in accordance with Bradley et al., Nature 309:255-266 (1984). The embryos are transferred to pseudopregnant females to obtain chimeric animals. These chimeras are crossed with normal animals to obtain germline transmission of the mutated gene. Two heterozygous animals are crossed to obtain homozygous animals for the specific mutation of interest. (See, Li et al., Genes and Dev. 9:2821-2830 (1995)). Due to the autosomal dominant inheritance of the COL2A1 mutations associated with ANFH, the mutant COL2A1 gene may introduce a dominant negative effect and the heterozygous animals are useful models of osteonecrotic disease. Several animal and in vitro models are available for the study of COL2A1 mutations of the invention. (See, for example, U.S. Pat. Nos. 5,593,859, 5,663, 482, and 6,448,470.)

Model systems allowing for the study of these events are extremely useful. COL2A1 −/− mice expressing mutant forms of the human COL2A1 gene are an excellent model for studying osteonecrosis. Transgenic mice expressing the COL2A1 gene mutation are especially useful in the development of compositions and methods of treating human type II collagen-related osteonecrotic diseases. Furthermore, the chondrocytes, the cells that synthesize procollagen type II from the transgenic animals that express the normal human COL2A1 gene, are similarly useful.

Techniques of detecting defective type II collagen activity or structure are known in the art. Such assays include electron microscopic analysis of collagen fibrils, microscopic evaluation of bone and cartilage tissues or cells, collagen multimerization assays, and molecular evaluation of collagen structure and stability. (See, de Crombrugghe et al., *J. Rheumatol.* 22:1 Supp. 43:140-142 (1995)). Further it is possible to measure disease progression with bone scan and MRI (magnetic resonance imaging) techniques.

Collagen

The COL2A1 gene encodes type II collagen, which is the main component of the fibrillar matrix of hyaline cartilage. Collagens have the capacity to form extra cellular fibrils or network-like structures and fulfill a variety of essential biological functions in vertebrates. Structurally, collagens are characterized by repeats of the amino acid sequence G-X-Y (where G=glycine, X=proline, and Y=hydroxyproline.) Collagen monomers multimerize into a triple helix through interactions involving the G-X-Y repeats. This assembly influences the polymerization of collagen fibrils. Mutations affecting the level of synthesis of type II procollagen or causing the synthesis of a defective form of type II procollagen have been linked to degeneration and malformation of cartilage.

Structural features of type II collagen and procollagen (encoded by the COL2A1 gene) are known in the art. The COL2A1 gene maps on chromosome 12, at 12q13.11-q13.2. This gene covers 31520 bp, from 48115008 to 48083489 (NCBI Build 33), on the reverse strand of chromosome 12 (SEQ ID NO:1), and genomic nucleic acid sequences of COL2A1 are set forth in SEQ ID NO:1. Protein encoded by COL2A1 constitutes a major structural protein in the extra cellular matrix of cartilages. Full length amino acid sequences of the Col2A1 protein, the G1170S Col2A1 variant, and the G717S variant are disclosed in SEQ ID NOs:3, 5, and 7, respectively. SEQ ID NOs:2, 4, and 6 contain the nucleic acid sequences encoding these proteins. As shown in FIG. 2A, a 3665G>A transition (GenBank NM_001844) that caused a Gly11170Ser amino acid change (GenBank NP_001835) was identified in all 12 patients in Family A (FIG. 1A) and 11 patients in Family B (FIG. 1B). In Family C (FIG. 1C), a G>A substitution was identified at nucleotide position 2306 (GenBank NM_001844). Similarly, the mutation in the COL2A1 gene resulted in the substitution of glycine with serine in the G-X-Y repeat at amino acid position 717 (GenBank NP_001835) of the predicted protein. The two mutations do not occur in 61 control individuals we analyzed.

A single nucleotide polymorphism (SNP) at position −767 in the promoter region, which displayed significant difference in allele frequency (P=0.0003) as well as genotype frequency (P=0.0001) between sporadic ANFH patients and healthy controls is prevalent in sporadic instances of ANFH. In silica transcription factor binding analysis predicted that the −767C>A substitution would alter a Sp1 binding site, and promoter function assay showed it affected COL2A1 gene expression.

Figure 2A:
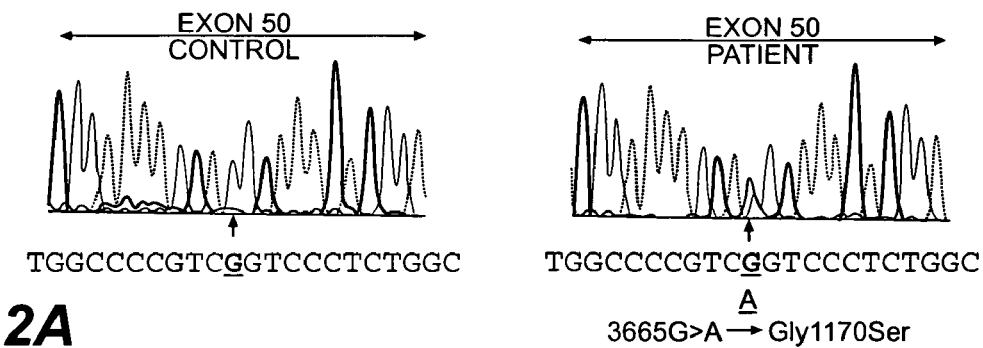
FIG. 2A depicts direct sequencing of PCR amplified fragments and reveals a G>A nucleotide substitution in exon 50 in the mutant allele from a patient in family A replacing a glycine codon with one for serine. The sequences depicted in FIG. 2A encompass positions 3655-3676 of SEQ ID NO:2.
Figure 2B:
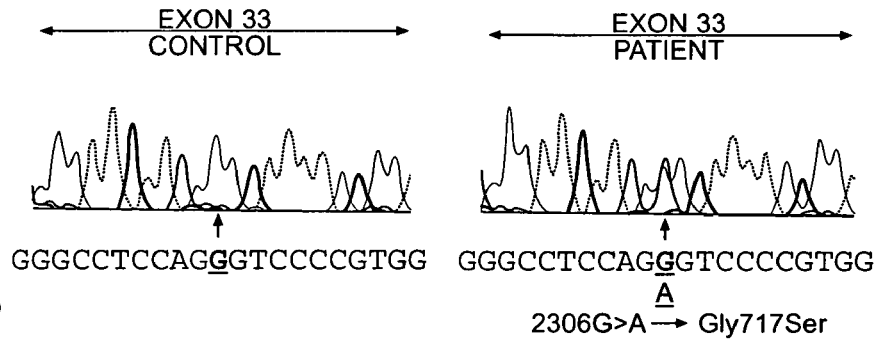
FIG. 2B depicts direct sequencing of PCR amplified fragments and reveals a G>A substitution in the mutant allele in exon 33 from a patient in family C. The sequences depicted in FIG. 2B encompass positions 2296-2316 of SEQ ID NO:2.
Figure 2C:
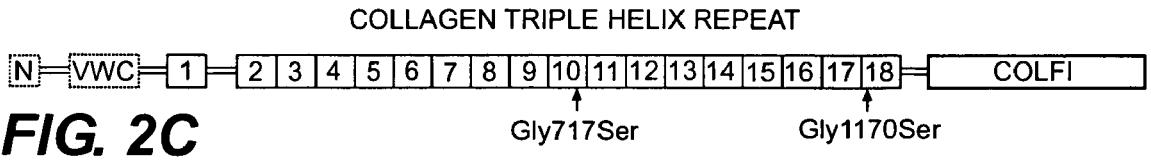
FIG. 2C shows a schematic diagram of the type II alpha 1 collagen COL2A1 gene product. The N-terminal signal domain is shown by "N", the von Willebrand factor (type C) domain by "VWC", the collagen triple helix repeats are numbered 1-18, and a region showing homology to a C-terminal fibrillar collagen domain is designated COLF1. Relative positions of the glycine 717 and glycine 1170 mutations are indicated with arrows.
Figure 3A:
FIG. 3A depicts that hip joint X-rays that were taken for (a) a normal control; (b) an affected individual (IV:5 in family A) showing stage III state according to Ficat classification; and (c) an asymptomatic carrier of a mutant allele (III22).
Figure 3A:
Figure 3A:
Figure 3B:
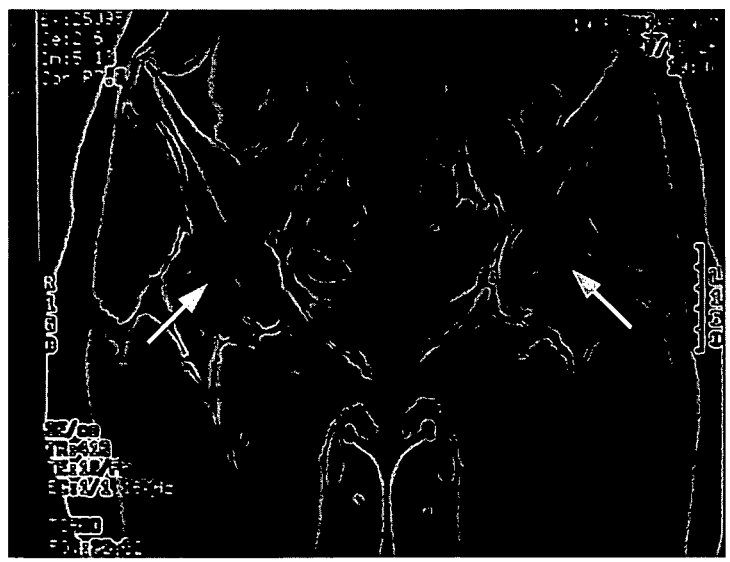
FIG. 3B depicts magnetic resonance imaging (MRI) scan on an affected individual (IV:5 in family A).

Some relevant structural features of the type II alpha 1 collagen (see FIG. 2(c) for schematic) are listed in the following table.

TABLE 3

Secondary Structural Features of COL2A1 protein: 1487 amino acid residues

| Reference | Amino Acids | Region |
|---|---|---|
| SEQ ID NO: 8 | 1-25 | N: N-terminal signal domain |
| SEQ ID NO: 9 | 34-89 | VWC: von Willebrand factor, type C |
| SEQ ID NO: 10 | 117-176 | Collagen triple helix repeat 1 |
| SEQ ID NO: 11 | 199-257 | Collagen triple helix repeat 2 |
| SEQ ID NO: 12 | 258-317 | Collagen triple helix repeat 3 |
| SEQ ID NO: 13 | 318-377 | Collagen triple helix repeat 4 |
| SEQ ID NO: 14 | 378-437 | Collagen triple helix repeat 5 |
| SEQ ID NO: 15 | 438-497 | Collagen triple helix repeat 6 |
| SEQ ID NO: 16 | 498-557 | Collagen triple helix repeat 7 |
| SEQ ID NO: 17 | 558-617 | Collagen triple helix repeat 8 |
| SEQ ID NO: 18 | 618-677 | Collagen triple helix repeat 9 |
| SEQ ID NO: 19 | 678-737 | Collagen triple helix repeat 10 |
| SEQ ID NO: 20 | 738-797 | Collagen triple helix repeat 11 |
| SEQ ID NO: 21 | 801-860 | Collagen triple helix repeat 12 |
| SEQ ID NO: 22 | 861-920 | Collagen triple helix repeat 13 |
| SEQ ID NO: 23 | 921-980 | Collagen triple helix repeat 14 |
| SEQ ID NO: 24 | 981-1040 | Collagen triple helix repeat 15 |
| SEQ ID NO: 25 | 1041-1100 | Collagen triple helix repeat 16 |
| SEQ ID NO: 26 | 1101-1160 | Collagen triple helix repeat 17 |
| SEQ ID NO: 27 | 1161-1220 | Collagen triple helix repeat 18 |
| SEQ ID NO: 28 | 1269-1486 | COLFI: Fibrillar collagen, C-terminal |

Procollagen a chain and collagen polypeptides are arranged as left-handed helices with three amino residues per turn. In these polypeptides, the amino acid glycine in every third position favors helix conformation. As depicted in FIG. 2C, collagen triple helix repeats are arranged in series along a COL2A gene product. These triple repeats are characterized by the G-X-Y sequence, in which the first position of the repeat is generally glycine, and the second and third positions can be any residue but are frequently proline and hydroxyproline. In a collagen molecule, three α chains are wrapped around one another to form a triple-stranded helical rod. A glycine's small side chain allows it to occupy the crowded interior of the triple helix. The ring structure of proline and hydroxyproline may stabilize the helical conformations of the polypeptide chains. The unusual amino acid hydroxyproline is formed within the endoplasmic reticulum by modification of proline residues that have already been incorporated into collagen polypeptide chains.

Sequences of the COL2A1 gene can be found in the literature and appear in the sequence listing. It will be appreciated that the genomic organization of the COL2A1 gene is complex. The COL2A1 gene covers a transcription unit of 31,511 bp, including 54 exons. By alternative splicing, 8 types of transcripts can be expressed, encoding 8 different potential protein isoforms that differ in the N-terminus, C-terminus, or collagen triplet repeat portion (G-X-Y region). It remains to be determined whether the differential expression of protein isoforms in various tissues contributes to the diverse clinical phenotypes in the COL2A1 gene mutations. Certain mutations in the COL2A1 gene are associated with a wide spectrum of disorders that are attributed to anomalous expression of the gene in cartilage or in the vitreous humor of the eye (see, Ahmad et al., 1991, *Proc. Nat'l. Acad. Sci. USA* 88: 6624-6627; Bonaventure et al., 1995, *Biochem. J.* 307: 823-830.)

Two specific mutations are exemplified herein as associated with heritable avascular necrosis of the femoral head. In each, a conserved glycine within a G-X-Y region is substituted. The glycine to serine substitution at position 717 described herein occurs in collagen triple helix repeat 10 and is encoded by exon 33, whereas the Gly to Ser substitution at 1170 occurs in collagen triple helix repeat 18 and is encoded by exon 50. Two embodiments of the invention, i.e., the single base substitutions depicted in FIG. 2, are exemplary of the invention. One of skill in the art would recognize that due to redundancy in the genetic code, the alternate codons TCT, TCC, TCA, TCG, or AGC would function identically to the AGT codon depicted in FIG. 2 to encode a serine residue at the mutated positions of FIG. 2. Additionally, substitution of a codon encoding an amino acid that is structurally or chemically similar to serine, or dissimilar from glycine may suffice. Similarly, replacement of a different conserved glycine in a G-X-Y repeat, such as the sequences of exon 33 or 50 would be highly structurally similar to the molecules depicted in FIG. 2.

The multiplex ANFH families reported here present a clinical picture that is indistinguishable from that of most sporadic ANFH cases, commonly seen in orthopedic practice. Other than the hip joint problem, the affected individuals are normal, displaying normal height and physical appearance. There are no anomalies in the ocular or auditory system. Unlike previous reports of generalized osteoarthritis, chondrodysplasia, or skeletal deformities, the ANFH cases from families A, B, and C have arthropathy limited to the hip joint. Furthermore, mutations in the two families involve a G-to-S amino acid change in the critical G-X-Y repeat, with each residing in a separate exon.

ANFH is a disease frequently diagnosed in patients receiving hip joint replacement. It has been suggested that a common pathogenesis pathway of ANFH involves the interruption of blood circulation to the antero-lateral part of the femoral head, leading to ischemic insult and bone collapse. The disease is aggravated by mechanical disruption, external pressure on or damage to a vessel wall, arterial thrombosis or embolism. The autosomal dominant form of ANFH represent a new group of skeletal disorder due to COL2A1 mutation, thus further expanding the phenotypic spectrum associated with this gene. Sporadic forms of ANFH cases may also be causally related to abnormal type II collagen function, see Example 4, and below. The exclusion of a pathogenesis pathway related to intravascular coagulation in the familial ANFH and the inclusion of ANFH as a form of type II collagenopathy might bear implications on the diagnosis and management of this important disease in orthopedics.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

EXAMPLE 1

A genetic approach to map the chromosomal position of the disease locus allowed identification of the gene responsible for the autosomal dominant ANFH families.

ANFH Genetic Analysis 30 ml samples of blood were drawn from each of the 31 members of the family, including 12 individuals with idiopathic ANFH. Genomic DNA from peripheral blood leucocytes was extracted manually as described. (Blin et al., *Nucleic Acids Res.* 3:2303-2308 (1976)). In addition, RNA was extracted using the Tri-Reagent® kit according to the manufacturer's protocol (Molecular Research Center, INC., Cincinnati, Ohio). A lymphoblastoid cell line was established by Epstein-Barr virus transformation. Twelve microsatellite markers were employed to test linkage between idiopathic ANFH and three candidate genes. Markers D2S410, D2S1328, D2S2271, D2S368 and D2S1334, spanning 19.9 cM, were selected for the protein C gene region. Markers D3S4529, D3S1271, and D3S2459, covering a 6.6 cM distance, were for the protein S gene. The PAI gene, residing on chromosome 7q21.3-q22, was investigated using the markers D7S657, D7S821, D7S515, and D7S1799, spanning 9.1 cM. Assignment of these markers to the cytogenetic bands was based on the NCBI human genome resources and detailed information about these markers is available at the NCBI Entrez UniSTS web site. Inter-marker distance was calculated from the genetic map of Center for Medical Genetics, Marshfield Medical Research Foundation.

Polymerase chain reaction (PCR) was performed in 96-well microtiter plate format, including in each well a 10 µl final volume of 40 ng of DNA template, 6 µl True Allele™ PCR Premix (Applied Biosystems) and 1 pmol of each primer. Thermal cyclying was carried out in a 96-Well Gene-Amp® PCR System 9700 (Applied Biosystems) with the following condition: initial heat step at 95° C. for 12 min, followed by 60 cycles of 94° C. for 15 sec, 55° C. for 15 sec and 72° C. for 30 sec. The final step is 72° C. for 10 min. The PCR products were electrophoresed on a 4.75% denaturing polyacrylamide gel (12 cm) with run module GS12C-2400 in a 377 ABI PRISM sequencer (Applied Biosystems), using TAMRA GS-500 as internal size standard. Mutiplex electrophoresis was carried out by mixing and co-loading different dye-labeled PCR products in the same lane. Overlapping DNA fragments were distinguished by using 5' end-labeled primers with three different fluorescent dyes: (FAM), (TET), (HEX) (Applied Biosystems). These three phosphoamidite dyes can be excited by blue, green, and yellow laser light respectively in a wavelength range 530 nm to 590 nm. Alternative fluorescing agents may be substituted. CEPH 1347-02 DNA of known genotype was included in each PCR reaction and electrophoretic analysis as a reference. Electrophoretic results were processed by the GENESCAN® software (version 3.1) (Applied Biosystems) and allele size was assigned by the Genotyper® software (version 2.5) (Applied Biosystems). Two researchers blinded to the clinical status independently read the genotypes.

Linkage Analysis

Computer simulation analysis of the familiar idiopathic ANFH pedigree was performed by the SLINK program. (Ott et al., *Proc. Natl. Acad. Sci.* 86:4175-4178 (1989)). A dominant model with a disease gene frequency of 0.0001 and a penetrance of 0.99 was assumed. Two hundred replicates for this family were simulated. The pedigree has a probability of 79% to detect a lod score greater than 3.

Two-point lod scores between ANFH and the markers were calculated by using the MLINK program from the LINKAGE computer package (version 5.2). A dominant genetic model was assumed with a disease gene frequency of 0.0001 and a penetrance of 0.99. Allele frequency for each marker was calculated from 31 collected individuals in the pedigree. Multipoint lod score was also calculated by using the LINKMAP program of the LINKAGE packages. (Lathrop et al., Am. J. Hum. Genet. 37:482-498 (1985)). The middle interval of three-point lod scores was extracted to plot a continuous multipoint lod score graph.

Figure 1B:
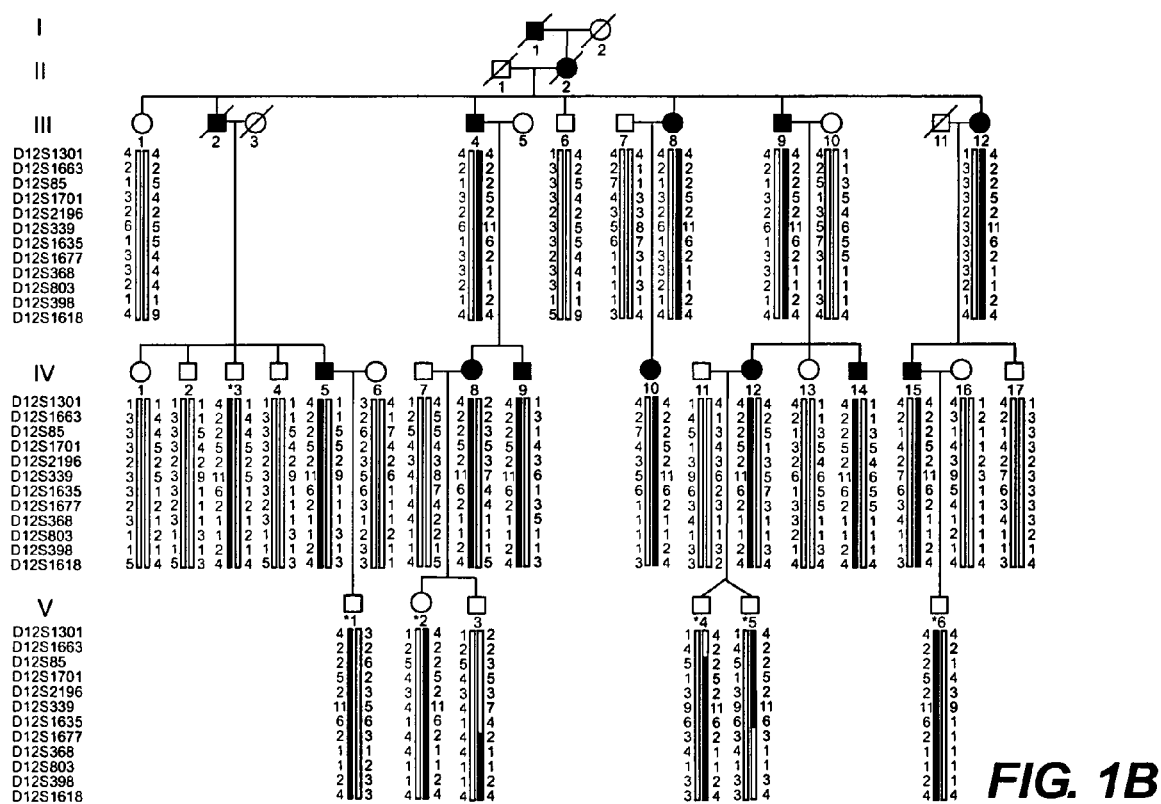
FIG. 1C depicts a pedigree of ANFH family C, similarly depicted. No Haplotype analysis is shown for family C. Analysis of the families' pedigrees results of a linkage analysis for chromosome 12.
Figure 1C:
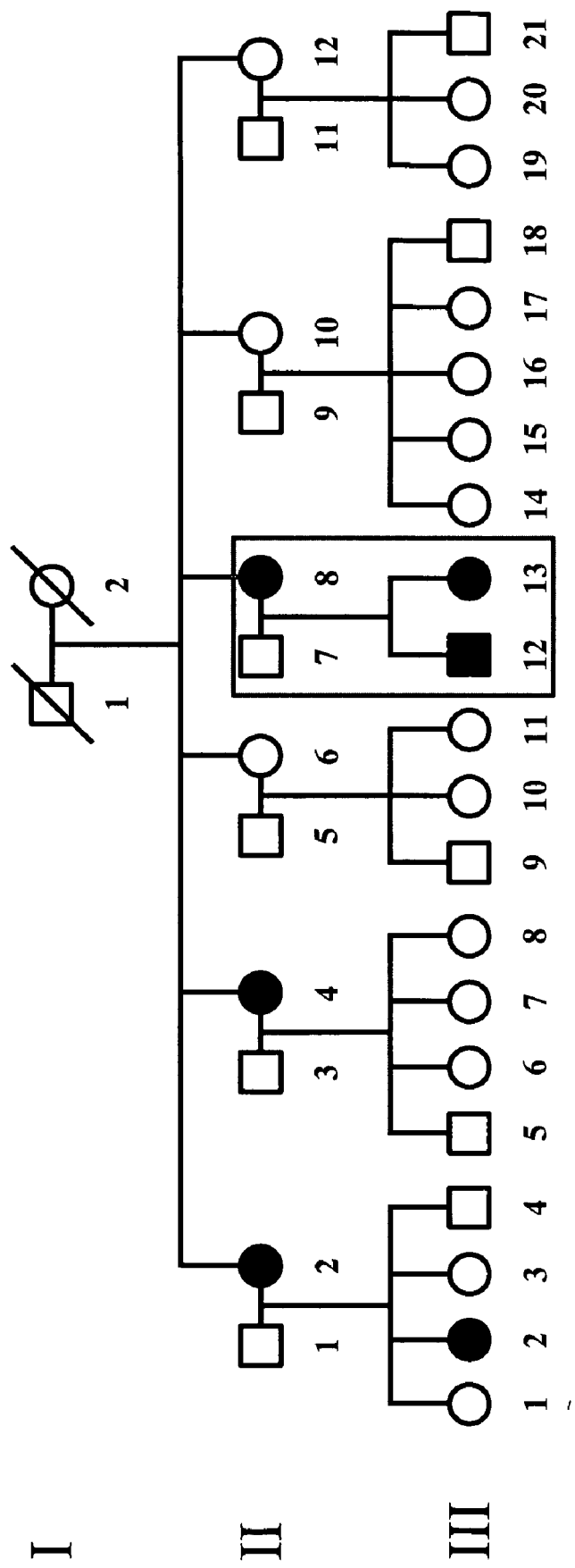

Among 75 members in family A, there are five males and eleven females affected with idiopathic ANFH, including two twin sisters (FIG. 1(a)). DNA samples are available from thirty-one family members (12 affected, 19 unaffected). In this pedigree, the mode of inheritance is apparently autosomal dominant and the average age of onset in the twelve patients is 25 years (range: 15-48 yr). Biochemical analysis of the twins showed that no possible risk factors, including SLE (Systemic lupus erythematosus), sickle cell disease or Gaucher disease, were associated with this hereditary form of idiopathic ANFH. Furthermore, except for the individual member of family A identified in FIG. 1 (a) as II:9, the patients are not alcohol users. According to the Ficat index, eight patients were graded as stage IV and four as stage I. For surgical treatment, arthroplasty has been performed on eight patients in the family.

Two-point lod scores for all flanking markers used for protein C, protein S, and PAI genes at a variety of recombination fractions were calculated. Overall, all markers generated negative lod scores at different recombination fractions. Lod scores<−2.0 were observed at small recombination fractions ($\Theta<0.01$) for all the markers and were still negative even at higher recombination fractions ($\Theta=0.40$) for most markers. Furthermore, multipoint linkage results, yielded by the LINKMAP program, also showed negative lod scores ranging from −2.03 to −21.99 for the gene protein C, −8.72 to −15.17 for protein S, and −6.81 to −17.1 for PAI gene. By using criterion of a lod score less than −2, the results from both two-point and multipoint linkage analysis exclude these genes as candidates for idiopathic ANFH in this family.

Linkage analyses were conducted on three genes related to thrombophilia and hypofibrinolysis: protein C, protein S, plasminogen activator inhibitor. Negative lod scores were obtained by both two-point and multipoint linkage analysis for the polymorphic markers close to these genes. Together, the results exclude a linkage relationship between these genes and the ANFH family.

EXAMPLE 2

Whole-genome screening was then conducted in two phases. A marker set of moderate density was applied to identify candidate positions first. Then, regions showing significant lod score were further scrutinized with high-density markers selected from each candidate locus. As shown in FIG. 1, significant multipoint lod scores (lod>3) spanning from the marker D12S1663 to marker D12S326 were obtained in an interval of 25 cM with a maximum lod score of 4.31 between the marker D12S1663 and D12S85 on the chromosome 12q13-14. Haplotype analysis indicated that a critical interval 8.2 cM between D12S1301 and D12S339 might harbor a gene for the ANFH family.

In the 5.13 Mb ANFH critical region, 21 known genes and 25 predicted genes were identified in the genome browser (NCBI build 33, April 2003). See Table 4 for an exemplary list of candidate genes.

TABLE 4

Genes between marker D12S 1663 and D12S 2196
Region: 44000000.000000 . . . 49000000.000000

| start | stop | cyto. | full name |
|---|---|---|---|
| 44033003 | 44044324 | 12p11.22 | similar to 52 kDa repressor of the inhibitor of the protein kinase |
| 44072395 | 44133320 | 12p11.22 | similar to eukaryotic translation elongation factor 1 alpha 2 |
| 44147650 | 44148111 | 12q12 | LOC121698 |
| 44201524 | 44231622 | 12p11.22 | hypothetical protein DKFZp434G1415 |
| 44231813 | 44260932 | 4 | interleukin-1 receptor associated kinase 4 |
| 44266559 | 44279211 | 12p11.22 | protein tyrosine kinase 9 |
| 44308803 | 44862570 | 12p11.22 | hypothetical protein DKFZp434K2435 |
| 44870937 | 44872247 | 12p11.22 | LOC160782 |
| 44981095 | 45349168 | 12q13.11-q13.12 | NEL-like 2 (chicken) |
| 45419888 | 45502813 | 12p11.21 | similar to contactin - human |
| 45535431 | 45538224 | 12p11.21 | FKSG42 |
| 45645863 | 45688819 | 12q | putative glycolipid transfer protein |
| 45875910 | 45905160 | 12p11.21 | similar to chromosome 11 open reading frame 25 |
| 46019522 | 46121197 | 12p11.21 | LOC144754 |
| 46127006 | 46178054 | 12 | LOC255659 |
| 46198840 | 46200718 | 12p11.21 | LOC144755 |
| 46201557 | 46202207 | 12p11.21 | LOC121707 |
| 46309758 | 46315047 | 12p11.21 | similar to hypothetical 139.1 KD protein C08B11.3 in chromosome II |
| 46323784 | 46379196 | 12p11.21 | KIAA1557 protein |
| 46390293 | 46463280 | 12p11.21 | splicing factor, arginine/serine-rich 2, interacting protein |
| 46658943 | 46740306 | 12p11.21 | solute carrier family 38, member 1 |
| 46829349 | 46843933 | 12q | solute carrier family 38, member 2 |
| 46854202 | 46872656 | 12p11.21 | LOC160793 |
| 46911661 | 46967413 | 12p11.21 | similar to Olfactory receptor 7A5 (Olfactory receptor TPCR92) |
| 46984965 | 47049308 | 12p11.21 | LOC160436 |
| 47056705 | 47058033 | 12p11.21 | similar to serine/threonine kinase |
| 47138920 | 47223421 | 12q12-q13 | solute carrier family 38, member 4 |
| 47266908 | 47302170 | 12p11.21 | similar to transient receptor protein 6 |
| 47332135 | 47370165 | 12p11.21 | LOC121063 |
| 47474875 | 47555813 | 12 | similar to adlican |
| 47559211 | 47559626 | 12 | similar to Interferon-induced transmembrane protein 3 |
| 47564786 | 47598765 | 12 | LOC254362 |
| 47620907 | 47641296 | 12p11.21 | hypothetical protein BC008360 |
| 47746246 | 47746727 | 12p11.21 | similar to ubiquitin/ribosomal protein CEP52 fusion protein - *Leishmania major* |
| 47788624 | 47872767 | 12p11.21 | LOC160432 |
| 47889413 | 47986545 | 12p11.21-p11.1 | similar to genethonin 1 |
| 47997846 | 48059310 | 12p11.1 | similar to ubiquitin C; polyubiquitin C |
| 48067930 | 48110658 | 12p11.1 | hypothetical protein FLJ21908 |
| 48114383 | 48130205 | 12q13.1 | protease, serine, 22 |
| 48132789 | 48135236 | 12p11.1 | LOC144266 |
| 48139310 | 48140347 | 12q13.1 | hypothetical protein HSU7927 5 |

TABLE 4-continued

Genes between marker D12S 1663 and D12S 2196
Region: 44000000.000000 . . . 49000000.000000

| start | stop | cyto. | full name |
|---|---|---|---|
| 48141696 | 48163410 | 12q13 | Rap1 guanine-nucleotide-exchange factor directly activated by cAMP |
| 48178030 | 48189193 | 12p11.1 | hypothetical protein FLJ20489 |
| 48189169 | 48205583 | 12q13.1 | histone deacetylase 7A |
| 48221568 | 48225271 | 12p11.1 | LOC160799 |
| 48230340 | 48240370 | 12p11.1 | LOC160798 |
| 48247982 | 48311429 | 12q12-q14 | vitamin D (1,25-dihydroxyvitamin D3) receptor |
| 48369982 | 48375315 | 12q13.1 | hypothetical protein MGC5576 |
| 48379437 | 48410949 | 12q13.11-q13.2 | collagen, type II, alpha 1 (primary osteoarthritis, spondyloepiphyseal dysplasia) |
| 48451595 | 48512107 | 12q13.1 | sentrin/SUMO-specific protease |
| 48525530 | 48544102 | 12q13.3 | phosphofructokinase, muscle |
| 48562541 | 48564221 | 12p11.1 | similar to olfactory receptor MOR259-1 |
| 48689557 | 48690261 | 12p11.1 | similar to Protamine P1 containing protein |
| 48702331 | 48711093 | 12p11.1 | similar to zinc finger protein 202 |
| 48832867 | 48833262 | 12p11.1 | acidic (leucine-rich) nuclear phosphoprotein 32 family, member D |
| 48842734 | 48856588 | 12p11.1 | LOC121273 |
| 48885834 | 48886772 | 12p11.1 | similar to olfactory receptor MOR160-1 |
| 48920106 | 48923165 | 12p11.1 | similar to olfactory receptor MOR160-1 |
| 48927894 | 48930255 | 12q13 | lactalbumin, alpha- |
| 48932754 | 48989024 | 12p11.1 | similar to olfactory receptor MOR122-1 |

EXAMPLE 3

Association of COL2A1 Mutation with ANFH

Figure 4:
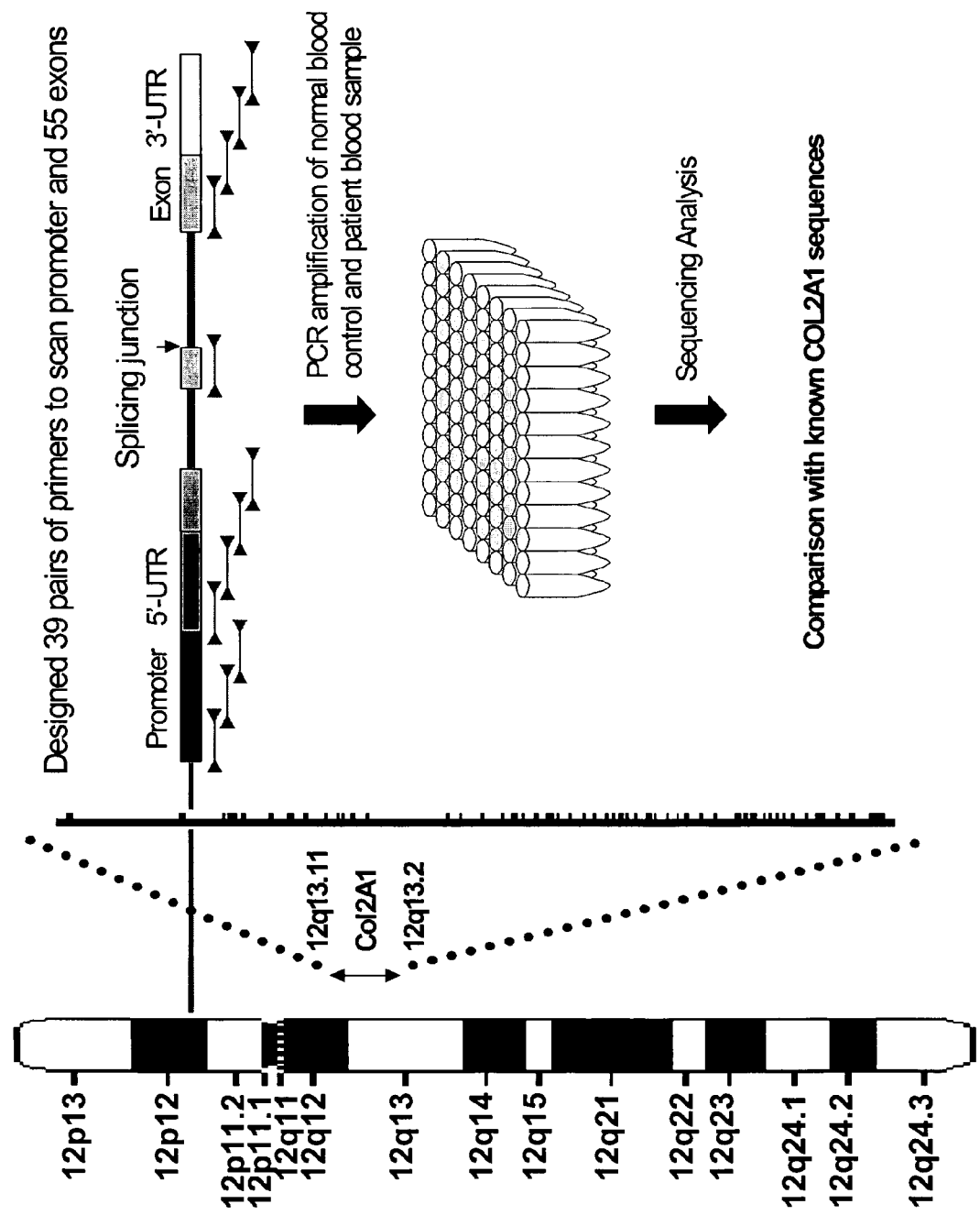
FIG. 4 represents an experimental procedure for identification of COL2A1 mutations. The coding exons as well as the 5'-UTR and 3'-UTR of the COL2A gene were analyzed for the core members in ANFH families (III:7, III:8, IV:5, IV:6, IV:7 in family A, III:9, III:10, IV:12, IV:13, IV:14 in family B, and II:7, II:8, III:12, III:13 in family C). Additionally, genomic PCR and sequencing were performed of exons 33 and 50 for all available ANFH family members and 61 control individuals.

A resequencing strategy was applied to investigate the possible involvement of COL2A1 and to uncover genetic alteration(s) associated with ANFH. See FIG. 4. As shown in FIG. 2a, a 3665G>A transition (according to RefSeq NM_001844) which caused a Gly1170Ser codon change (according to RefSeq NP_001835) was identified in all 12 patients. These RefSeq locus identifiers are NCBI accession numbers for publicly available homo sapiens collagen, type II, alpha I (COL2A1) mRNA and polypeptide sequences.

Resequencing strategy: The coding exons as well as the 5'-UTR and 3'-UTR of the COL2A gene were analyzed for the core members in ANFH families (III7, III8, IV5, IV6, IV7 in Family A, and II7, II8, III12, III13 in Family B). Additionally, genomic PCR and sequencing were performed for exons 33 and 50 for all available ANFH family members and 61 control individuals. Twenty-five ng of genomic DNA from each sample was used to amplify genomic fragments of the COL2A1 promoter, exons, and exon-intron junctions in 39 PCR reactions. Oligonucleotide primers were designed using Primer3. (See Table 2; Rozen et al., Methods Mol. Biol. 132: 365-386 (2000)). PCR was initiated at 95° C. for 10 minutes, followed by 45 cycles of 95° C. for 30 seconds, annealing temperature for 30 seconds, and 72° C. for 45 seconds. The final step was at 72° C. for 3 minutes. The optimal annealing condition for each pair of primer was pre-tested. PCR products were treated with exonuclease I in order to remove excess primers. DNA sequencing reaction was performed using Dye-terminator (Applied Biosystems Inc., Foster, Calif.) with the same primers for PCR amplification. Sequencing reaction products were electrophoresed on ABI 3700 or ABI3730 PRISM DNA sequencer to determine the sequence of amplified fragments. The sequencing result was analyzed using Phrap-Phred and PolyPhred (ver. 10) software. (Ewing et al., *Genome Res.* 8:175-185 (1998); Ewing et al., *Genome Res.* 8:186-194 (1998); Gordon et al., *Genome Res.* 8:195-202 (1998); phred/phrap/polyphred/consed pipeline; Nickerson et al., *Nucleic Acids Res.* 25:2745-2751 (1997)) Heterozygous variation was defined by the existence of double peaks at one nucleotide position.

This mutation in the COL2A1 gene is associated with the disease in family A based in three data points. First, the mutation segregated with the disease. Second, the variant sequence does not occur in 122 control chromosomes of 61 normal individuals. Third, the amino acid change falls on a critical residue in the G-X-Y domain of the encoded collagen molecule. Point mutations resulting in the replacement of glycine with a bulkier amino acid have been reported to be the cause of several inherited diseases of collagens (Kuivaniemi et al., 1997).

To gather additional evidence, the COL2A1 sequence in another family was investigated. The pedigree is shown in FIG. 1 (c), and a core family agreed to participate in this study. Whole blood was collected from a couple and their two affected children. As shown in FIG. 2b, a G>A substitution was identified at nucleotide position 2306 (RefSeq NM_001844). Again, the mutation in the COL2A1 gene resulted in the substitution of glycine with serine in the G-X-Y repeat at amino acid position 717 (RefSeq NP_001835) of the predicted protein. This variant sequence does not occur in the same 61 control individuals analyzed.

EXAMPLE 4

COL2A1 Mutations in Family Members

DNA sequencing of family members in the pedigree A identified individuals at risk of developing ANFH. Among 19 individuals who presented no symptom in the initial medical examination, 16 had G/G sequence at nucleotide position 3665, while 3 (III15, III22, IV9) had G>A transition. For markers in the critical interval between D12S1301 and D12S339, these individuals carry the same haplotype as the ANFH patients (FIG. 1). One subject (III22) was recalled for further investigation by X-ray. As shown in the FIG. 3, in two years time, the disease has advanced to the late stage of ANFH and only recently has the subject begun experiencing pain in the groin. Haplotype and sequence analysis can, potentially, offer presymptomatic diagnosis to ANFH families, and the results of DNA test corroborate with clinical manifestation, although there is individual variability in age of onset and tolerance to the disease symptoms.

EXAMPLE 5

Association of COL2A1 SNP with Sporadic ANFH

Figure 5:
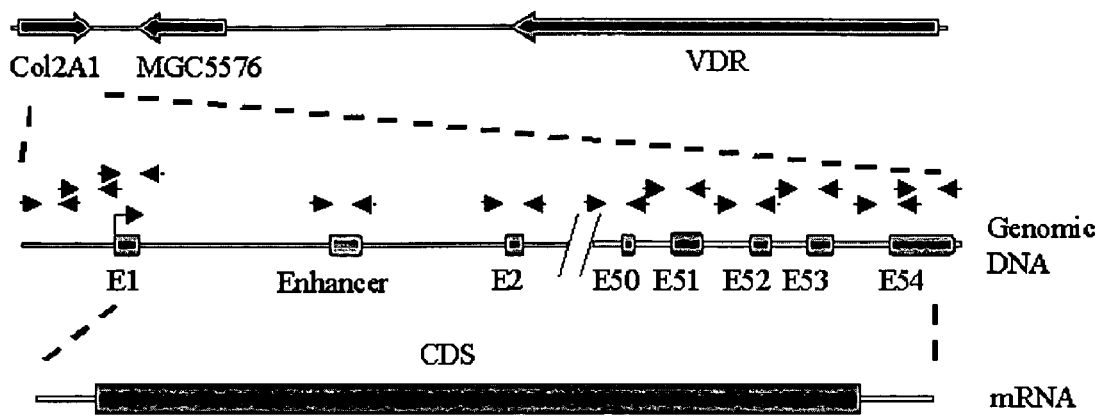
FIG. 5A depicts a re-sequencing strategy of the exonic sequences and promoter region of the COL2A1 gene that was conducted in sporadic ANFH cases and control subjects.
FIG. 5B shows a diagram of a promoter function analysis using a transfection experiment.
FIG. 5C, quantitates relative reporter gene function, indicating that a C>A substitution at the −767 position reduced promoter activity by 2.5 fold in this assay.
Figure 5:
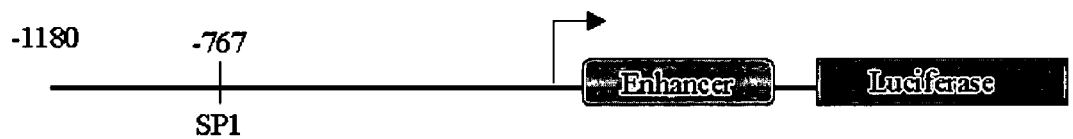
Figure 5:
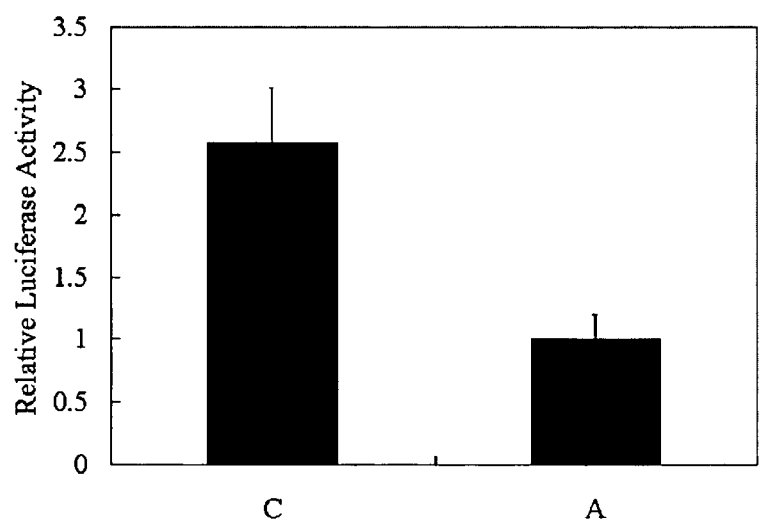

For sporadic ANFH cases and control subject, the exonic sequences and promoter region of the COL2A1 gene were re-sequenced to reveal any sequence variation that is associated with the disease (FIG. 5A). A total of 39 PCR amplifications were performed on each selected DNA sample to cover the target sequence, and 23 SNPs in the COL2A1 gene have been identified (data not shown). In this collection, one SNP, −767A, (SNP rs 3809324) was present at higher frequency in the patient group (35%) than in the control group (18%) (P=0.0003) (Table 4). Moreover, out of the 65 sporadic ANFH cases, 10 (15.4%) are homozygous and 26 (40.0%) are heterozygous for the −767A allele. In contrast, 30 (19 heterozygous and 11 homozygous individuals) out of 113 controls (26.6%) have at least one allele containing this −767A variant. The frequency of homozygous genotype plus heterozygous genotype is significantly different between the two groups (P=0.0001), indicating that the −767A may be useful as a disease susceptibility allele, or predictor of disease phenotype.

TABLE 4

SNP analysis of the COL2A1 gene in sporadic ANFH

| SNP rs | Nucleotide change | Genotype 11/12/22* | | | Minor allele frequency | | |
|---|---|---|---|---|---|---|---|
| | | ANFH (n = 65) | Control (n = 113) | P value | ANFH (n = 130) | Control (n = 226) | P value |
| 3809324 | −767C > A | 29/26/10 | 83/19/11 | 0.0001 | 0.354 | 0.181 | 0.0003 |

*"1" denotes the major allele; "2" denotes the minor allele.

Further analysis revealed that this SNP −767A occurs in a consensus binding site for the transcription factor Sp1. We next carried out promoter function analysis using a transfection experiment with a chondrosarcoma-derived cell line (FIG. 5B). As shown in FIG. 5C, the C>A substitution on the −767 position reduced the promoter activity by 2.5 fold as indicated by the luciferase reporter. This result suggests strongly that the SNP at the Sp1 site affects the COL2A1 promoter function.

The function of COL2A1 promoter was assayed as follows. The COL2A1 promoter region was synthesized by PCR amplification. The sense primer was Col2A1-En-1F: 5'-CA-GAAAGGAGCCAGCGCC, (SEQ ID NO. 115), and the anti-sense primer, was Col2A1-Pro-2R: 5'-GGCTAAGGT-GAGAGAGGG, (SEQ ID NO. 116). PCR amplification conditions were 95° C. for 5 min, followed by 45 cycles at 95° C. for 30 sec, 60° C. for 30 sec, 72° C. for 4 min, and a final extension at 72° C. for 10 min. The 3,960-bp amplified fragment was subcloned into the pGEM-T-Easy vector (Promega). This intermediate construct was then subjected to a SrfI/BsaBI fragment (2.1 kb) deletion and self-ligation, forming pGEM-T-Col2A1-Pro-En. The SphI/SpeI fragment (1.8 kb) of this plasmid includes the promoter and the enhancer region of the human COL2A1 gene. This fragment was then subcloned into a luciferase reporter vector, pGL3-Promoter (Promega). The final recombinant construct, pGL3-Col2A1-Pro-En, was verified by restriction mapping and DNA sequencing.

For transient transfection, SW1353 cells (human chondrocyte cell line) were maintained at 37° C. with 5% CO2 in DMEM medium (GibcoBRL) supplemented with 10% heat inactivated fetal bovine serum (GibcoBRL) and 1% Gluta-MAX (GibcoBRL). For luciferase reporter assays, 3.5×106 of the cells were seeded in 6-well plates (Falcon) for 16 hours before transfection. The cells were transfected with lipofectamin 2000 (Invitrogene), using 4 mg of total DNA consisting of 3.2 mg of test plasmid and 0.8 mg of pCMV (cytomegalovirus)-βgal. The pCMV-βgal plasmid contains the human cytomegalovirus promoter in front of the bacterial β-galatosidase gene and was used to correct for variation in transfection efficiency. After 48 hours, the transfected cells were harvested with 200 ml M-PER buffer (Pierce). Cell lysates were collected and analyzed for luciferase (LucLite, Packard) and β-galatosidase (Invitrogen) according to the manufacturers' instruction.

All publications and patents and sequences cited in this disclosure are incorporated by reference in their entirety. To the extent the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series.

The specification is most thoroughly understood in light of the teachings of the references cited within the specification. The embodiments within the specification provide an illustration of embodiments of the invention and should not be construed to limit the scope of the invention. Those skilled in the art will recognize, or be able to ascertain using no more than routine experimentation, many equivalents to the specific embodiments of the invention described herein. Such equivalents are intended to be encompassed by the following claims.

What is claimed is:

1. A method of detecting a genetic predisposition for avascular necrosis of the femoral head (ANFH) in a human subject, said method comprising:

obtaining nucleic acid from the human subject; and detecting the presence of an adenine nucleotide at a position corresponding to position 3665 of SEQ ID NO:2 in a type II alpha 1 collagen (COL2A1) DNA or in a COL2A1 DNA fragment that includes a position corresponding to position 3665 of SEQ ID NO:2, whereby the presence of the adenine nucleotide indicates a genetic predisposition for ANFH in the human subject.

2. The method of claim 1, wherein the presence of said adenine nucleotide is detected by examination of the nucleotide sequence of the COL2A1 DNA or fragment thereof in the human subject.

3. The method of claim 1, wherein the nucleotide sequence of the COL2A1 DNA or fragment thereof is detected and compared with the corresponding region of a standard DNA.

4. A method of identifying a human at risk of developing avascular necrosis of the femoral head, said method comprising:

purifying nucleic acid from a human subject; and detecting the presence of an adenine nucleotide in a COL2A1 sequence in the nucleic acid at a position corresponding to position 3665 of SEQ ID NO:2, whereby the presence of the adenine nucleotide indicates an increased risk for developing avascular necrosis of the femoral head in the human subject.

5. The method of claim 4, further comprising comparing a COL2A1 gene sequence of a family member of the human subject to a COL2A1 gene sequence of the human subject, whereby the presence of the adenine nucleotide at said position in the COL2A1 gene sequence of the family member indicates an increased likelihood of avascular necrosis of the femoral head in the family member.

6. A human genetic screening method for identifying a COL2A1 gene mutation comprising detecting in a nucleic acid sample from a human subject the presence of an adenine nucleotide at a position corresponding to nucleotide position 3665 of SEQ ID NO:2, thereby identifying the mutation.

* * * * *

SEQUENCE LISTING

<160> NUMBER OF SEQ ID NOS: 116

<210> SEQ ID NO 1
<211> LENGTH: 31511
<212> TYPE: DNA
<213> ORGANISM: Homo sapiens

<400> SEQUENCE: 1

| | | | | |
|---|---|---|---|---|
| acgcagagcg ctgctgggct gccgggtctc ccgcttcccc ctcctgctcc aagggcctcc | | | | 60 |
| tgcatgaggg cgcggtagag acccggaccc gcgccgtgct cctgccgttt cgctgcgctc | | | | 120 |
| cgcccgggcc cggctcagcc aggccccgcg gtgagccatg attcgcctcg ggctccccca | | | | 180 |
| gacgctggtg ctgctgacgc tgctcgtcgc cgctgtcctt cggtgtcagg ccaggatgt | | | | 240 |
| ccgtaagtct tcccccgccc ctgcctgcct gcctgctttc catgcgtccc tcagcatcct | | | | 300 |
| tctcccggc ccgctccagc tctggagccc gcggctccgg gctaaaacgg ctcccggggt | | | | 360 |
| cgtagcgcgc cgacttaggc acaggacacg cagaagttca ccaagaagag ttctgccaat | | | | 420 |
| caaggactct gtcccagggt cctcggtgcc catcgcagtt gcaagtattt gcaggtccct | | | | 480 |
| acgttgcgct agaatactga acttgcaaag tgttggctcg gagaagtttg cgcacagata | | | | 540 |
| taaatgggct cttttccacc agctttgata attaggcgca catgcacaca gctcgcctct | | | | 600 |
| tcgaagcact tcgagttcag caaaaacaga tctcaactca tcgaacttag gtgaagtagg | | | | 660 |
| aaagagagag cgcgagcgag ggagcaagca aacgccaaag ggttgacttc acagcctgtc | | | | 720 |
| caaggcttgg tggctggtgg gctcaaagca gagttagaca aaggggacta acactctgac | | | | 780 |
| actggtgggt gaaatccca ggccacaaag aacggcttcc gataggccct ctgagacctc | | | | 840 |
| agcgcctctt tagggtaccc tcccctccc agctggccct ggagcaaggt gcagccctag | | | | 900 |
| cgctcatctc gacttccctc cgtccgcctg cgcctctctt ctgataaagg gtacagaaac | | | | 960 |
| ttccagtagg agaggccatc tgaaagacga taacattcca accagaccgt gcttttcaaa | | | | 1020 |
| tgccccgaa aatagcgccc ccttcccgc ggtcttaccc cattcccgc cgccccgagg | | | | 1080 |
| tactacaatg agttactttt ctaaattctg gaactcaccg agccaggctg cgtggtgtgt | | | | 1140 |
| gtgtgtgtgc gtgtgtgtgt gtgtatgtgt gtgtcaggga aggggagcag gctggtcgat | | | | 1200 |
| tgctacggtt gctacaacta tttcaaccgg tatagttaga gatggctctt gtagtcgggt | | | | 1260 |
| ccaaatgctg ttcggactgc acctttctac ccctcctttg gtaaggtcca ctgtctggga | | | | 1320 |
| ttatattcag gacaaacgaa gcctggaaag tgtattaggt agagaggatt ttttttttcca | | | | 1380 |
| cgtgtttggg cacgtttccg acggctggga ttccagccct gtctttgtat gttacagatt | | | | 1440 |
| gtaaatcaat cgcagaggga aactcttcgg cggggggaat aaaagttctc tgccttcgag | | | | 1500 |
| gctctgtggg ccctctcctg ccaccaggct gtttccaggg atagcgtgga aggcggcggg | | | | 1560 |
| ctcaggcggg ctttccggtc attagcgcag cgggggcagg gctggagcct gcggcgcagc | | | | 1620 |
| tgcgaggagc cgggagcagg agactctggc cgggtcaccc ggtagtgcgc taagctggag | | | | 1680 |
| gcgcgctcct gggcatttga ggaatacagc gtgactatac gtggcctgga ctcagactga | | | | 1740 |
| ctatattttt gtactacatt tacaagcaca cgcccacaaa gctgtcttct tgactgaccc | | | | 1800 |
| ctgccttagt gcgcaatgga attagctggg tggctttaaa ataattctca aattctccat | | | | 1860 |
| ccggtattag ggtcgcttgc ttaattaggc ggtagagctc tctcatcgcc gcatctttcc | | | | 1920 |
| tgggagggag tgattccaca gcttctccgg cccaaacctt ccagtcgctc ctcctcccag | | | | 1980 |
| agggagtgtg attctgcatc cgagaggctg attttgcgcc ctggagcatc ccacctttta | | | | 2040 |

```
taacttcccc cgcctggggt cagcggaccc aaaggtgtga cgtggggaaa tgcgcagtct    2100
gcgtggacgt caggaatgtc agacacctag agctcggcca caccctcct ctccatcttt    2160
ccacgagttt gagaaactta ctggcggcgg cgtctttgac cctcatctgc atttcagagc    2220
cctcgcctcc gaaagtgccc ctggctcagg ggagagatct caatcctcct ttgtgaggct    2280
tgtttgcatt gggagattgg cagcgatggc ttccagatgg ggctgaaacg ctgcccgtat    2340
ttatttaaac tggttcctcg cggagacctg tgaatcgggc tctgtgtgcg ctcgagaaaa    2400
gccccattca tgagagacga ggtccagtgg gttctctcgt actcccagac ccctctcccc    2460
acaatgcccc cctgtgcccg cccgccgcca cctctcggct ccagccctgc gcagagcggc    2520
ggtgaagcaa aacagttccc cgaaagaggt agcttttttaa ttggcttgcc acaaagaatc    2580
acttatacgg ccctgcggta atgaggggaa ccggatcagg cgcgccggga tgctatcggc    2640
agccgttttg gagcagcaat tatggtggtc ctgggctcct ccgtccacac ctaggggatc    2700
cggttacggc gctggctcct ttctggggca gtcatttaat cccactttc actctcccgg    2760
tgtctgtgag cgagccgtgt ccagagccga agccacagag tcactcagcg gctcttacac    2820
ccagcgcagc ctggccccgc ccctgcgccg gcgcttcccg ggccgccctt ccccgggaaa    2880
tctgatccgc acggggagtg gcccctctcc tagcatttcc cctctcctc cctgggtcct    2940
catgggcgag ggtgggctct cctgtagtct gggctggagc gcattaaccg atgcccctc    3000
tcccacacct tcctcaccgc ctgcattcca ctgctccagc tattttaacg gcgggtgtgt    3060
ccccgcaact tctgtatttt ccctggaatc cctcacccct ctgtgattat cttgcccaaa    3120
ggctaggcgg atttcttcta gtgggaaagt aaaaaggaaa gtttatcttt ggattttcac    3180
tctctttaaa gagcagtggg caggctcgtt tctttctcgc cctctgggtt tgtggctctt    3240
tcctattatt catcccctgc tgctgctatt gccttgggga ttttgatgag aaaaacagcg    3300
ctgggcgctc cctagcacgt ggtgcgggct ctacagccct tggctgctaa ggagcgctct    3360
tgtcagcaca ggtttcattt gcagcatgaa ttccagacgg cagggcgctg gtggaggaga    3420
ctagtccctg ctattcttcc tctgcagtct tggaggagc caggcctgga ctggccaatc    3480
ttagccctag ccaggtattc aacgaccct gctccccaaa ctggggtgct gttttcagat    3540
ggaggcaggg cctctccagg cagggctaca gtggaggtc agcactgggg gcgctttggc    3600
tccactggcc tcctaagcag tttattagcc tgcccaagcc ccaagtgtat tgtttgaatg    3660
ggtctatccc cctccccaaa ttggtcctaa ttcaatatg gttcaaagaa tgagacaaga    3720
tcctaattct aatagctcgt cttttcaccc ccctttctta tatacctatt tttggagcct    3780
cactgcttat agattccaat ttttgtaggt agaattttct acattccctc tgaatgttag    3840
ttgtcagttg tatttagcta atcccataat tcccagagga aggcagaaga aagaagactt    3900
ctctgctcct gggctggtgg aagggaggtc tcgccatttt tctgtctcct ttcttttat    3960
agtcccagaa ttcctattca gaatatcttg tctcctccct tccgctcacc ctccaactcc    4020
ctccacccac tccatcacct ggtctccccc gtattaggtg ggtaaagaga atatagtata    4080
gtaaccccc accttcattg ctgggtcaag attttcactg gtgaatagac aacatggtgc    4140
aagtgcata ataaatattt gttgaataca tggaaaaatc aatgatgttt taggaaaata    4200
atttttaagt tctatatgtc caggtggccc cagcctacat tcttcagcat ttgaattctg    4260
tcaagttgac tgcaacctct ctcttttct ctctggctcc ccaccccctc cttcccttgg    4320
ctctctgctt ctccctcccc acccttggtg cagaggaggc tggcagctgt gtgcaggatg    4380
```

```
ggcagaggta taatgataag gatgtgtgga agccggagcc ctgccggatc tgtgtctgtg   4440
acactgggac tgtcctctgc gacgacataa tctgtgaaga cgtgaaagac tgcctcagcc   4500
ctgagatccc cttcggagag tgctgcccca tctgcccaac tgacctcgcc actgccagtg   4560
gttgtaattt atttatttcc tgttcaacat aaataaatta cttgcaagca ctgcaaacac   4620
gctcccatag atgctggtcg tctctgcaaa gcagaggggc tagttatcca tgggacctgg   4680
tagctggggt agaaaggaaa ggccacttct cacttgcagg ttgaaactga gtgaacgagc   4740
ctgagacact agaggggtcc ttctttgccc aacatctcca aaacatttg cttccaagac   4800
acatgaagga cagatgtgat tctacaaaaa aaaaaaaaa aaaatcctct ctgaaatcat   4860
ctctgcaaat tactagagcc actatggaga tcaaatgctc tgtctggcca atccacgaat   4920
taattcctcc tctgccaccg acaccttgtc ttctccttag aagacttcta tgtatgtggt   4980
cttcagtgtg gagaaagctc tgccagctag tggggagact gcaggggcag aggctccctc   5040
tttgagttat ggaacattgg tggtagtttc ctctctgcta ttacctctct tggagttgac   5100
cattaattca gaagcaaaat aataggagag ggaagggcta ggctttggga gttctcgtgg   5160
ggacgggtgg agacagagcc ccatgtatct gcactgtagt gggtggttat aaactcccag   5220
ttagatccag tgctggtgga tgatatatgt gcaggtgacc ccttcccagc attcatacag   5280
atgtcctatc tccctgcaga gtgagtgggg acgcttgtgt aggttttttg ggtagctctt   5340
gctgtccgct tcctgctgaa gtagagaagg ccgtggcaag ggaagtgaga agctgccttt   5400
ccttaacact tcaccaacac tggctcccta atgtgcagat tcccagatcc tttctgaggg   5460
gcccgtgtga gtgaagtgtt gattgccttt actattttgc tgctactgtg aaggagaggt   5520
tattgactgg ggatggcaca ggctatgatg ctccgatgct cttcataact catatgcctt   5580
gctgtttttg tgttttattt tgtgcttgct tcaaggagac ccagctctaa tgtaagacct   5640
ttctaagtac ctaactcttc ctctgggagg gcttggggtt cgggaacggc tcctaccct   5700
gtgggggaa gagagactga atctgtgctt tccttcttgt ggctgattag atcttgagct   5760
cttcattgcc tttttgtgct gcccttgctc cttctttttg catgctgcct gcttttgaa   5820
taacaaagtc tgggtcacct ccattcctca tgggacctca gcaaccccag gccacagtg   5880
gccctaacac cccaacagag gggttcagtg gagtcacagg aagctgccgc cttccttgat   5940
tgtgtccttt tacttgtttg atctaatgag tgtttgagtg acaagaatag gtattttcc   6000
atctcaagat tcttaccttc ttcttctcta tatttttcc cttgcagggc aaccaggacc   6060
aaaggtaagg gctttcttct ttttcttttt tcatattttt ttggctttat attttctgct   6120
tcaaaagcaa tgctatgtta atccagtctg tgatttttta gacatcagaa gatatctgtt   6180
tcagagggta cctcaacaca ggggctgctg gcagggtttt agactagggg cttagtgggc   6240
ttactcggct taatcctgtg aatgtttcat gtttcaggga cagaaggag aacctggaga   6300
catcaaggat gtaagtgcaa attattctca cccggtattg cagctgctgc tctaaatggg   6360
tcatttcctt gtgctctcct ctaacttacc atcctgtggg gctctctctc acagattgta   6420
ggacccaaag gacctcctgg gcctcaggta agagagggag aaatctcttt ctccgtccct   6480
tcctcgctgc gcgcaagtta ctgatctgca ggctcctggc cttgctgtca tcttaccatg   6540
ttcttcacct tcagggacct gcaggggaac aaggacccag aggggatcgt ggtgacaaag   6600
gtgaaaaagt gagtaaaaag caatgctgct tgaccctggt ggacttccca ggtccccaa   6660
ggccccacca tgtgtttaag ggcctggtca cctcttaaag agcagccaag ggacagatgg   6720
ctcttggaga aacactgctt cccattgatg ccttttttctc tttatgccaa gggtgcccct   6780
```

```
ggacctcgtg gcagagatgg agaacctggg acccctggaa atcctggccc ccctggtcct   6840
cccggccccc ctggtccccc tggtcttggt ggagtaagta tccttacttc ccattccttc   6900
aggctgtccc tccagaaatg tggcttttaa attgctgctt gcacttacct ggctggctcc   6960
cagggctgcc agcagtgtgt acatagcctg tccatgggct ttgccctcag gcctgtaatt   7020
tagaagagtc acatattagg catgagactg tggtgctaag ggctggcttt tttcactaac   7080
tgggattcta taaagaaagt cctcagttac ctggcttcct ggcatctgta ccacgtagtt   7140
gatgctgggg ggtgggtgta agggatagga ggaaggatga ctgggcactt gtatttccct   7200
ggaagacgag tgaccactgt ccttggaaga catttatcct tggttcttgc caagtacatt   7260
ccaagcaact attcactctc atgaaagagc tccactgagt gaaggtgtgt ggctaaagtc   7320
aattctggaa tcaaccaat caacaaatta tatgattgcc tagtttttgc aggtttgcta   7380
ttttgatgtt tgctgtattt taaattctta aactcaaatg ggatcacaga tgcctactac   7440
atctcttgct gaaatattcc aagactgttg attttagtct tttgctgggc actaaagtct   7500
taaagaataa agaacaccct tagaaggttt ggttatgttt ctccatatac gttaaataac   7560
atctgtcata ttttagagca taaaaataat tttataaaat gaaatgcaag gaactgatac   7620
ttcctcaaat aacactttcc cttccagtga aatgattttg ccactgtcat ctaataatcc   7680
attcccaaaa ttactttcca ggcatcagtg gtaattctga tcaatgatag gttagtctcc   7740
aacaatcaga gtttatctca gtagagttct ttgtatccat atagagctta cctagccaag   7800
tagggaagac ctagtgcctt tcaacctcct aacgttgttg ggtttctttg cagaactttg   7860
ctgcccagat ggctggagga tttgatgaaa aggctggtgg cgcccagttg ggagtaatgc   7920
aaggaccaat ggtaagaaaa gacactagtt ctttgcagcc aaaatggcag gaggtggccc   7980
ttagcagagc cagagagtct gacaacctct gctttacaga taattgctta gagtggctct   8040
cctccgtagt tatgtaacct cccattcagc tagcccaaag catttggttt ttaatggcaa   8100
tggatgccac ttttaatgat gcgctggagt gactaagaag aatgaagatg gggagatgca   8160
tataggctga tctgttagaa gaccagttgc tattgctctt ggaatgagaa ctgaagaatg   8220
cagacagcag ctactgttct ccagcatcca cagacttcca gcaggaaatc tcagcccgca   8280
gctctgactt ggcacatgct aaatgaaact cagcctttag taaacatggc tgctgtccag   8340
gagaaagcaa ggccagcttt tctgtccaaa tggtgcctat aaataaaaat agagtgttgc   8400
gtggggagtg ggaaatgaga gggagcagcc actctaggcc ccttgcccac agagtaactt   8460
cttgtccttt gcccgggctg ttggctggga gaagatggca cactggaggc cactgaggaa   8520
gcatgtgtag taaacccctc attttctgtt ccgatgcagg gccccatggg acctcgagga   8580
cctccaggcc ctgcaggtgc tcctgtaagt atctgcaatt cttttttgcct ccatcgtgtc   8640
gcagatgatt cccaagcact atgatgtttt agcagtttat agggattgac ctggtatcct   8700
cattttactt tttaggggcc tcaaggattt caaggcaatc ctggtgaacc tggtgaacct   8760
ggtgtctctg tgagtaccag cacggccctg tcccttctct gggggagcct ctaatgatag   8820
accactagga ccgcagctgc tgtccctccc aggctctgcc cagctctttc ccacagtcgg   8880
tggcccaag gaaattcgga tgtcacttcc tagctgtgga ggaactctga cagacagccc   8940
aatgtggcaa ggaccaccag ggactctgtc ctaacagccc cctttccggg tcaccccagc   9000
ctgtgctatc tgctgcgtcc cactatgatc tctgcacctt tgctctgacc ttcccatctt   9060
tcttcttcat agaagaactg gcttccaaaa ctacaatgtc aaagttttgt ccattgctta   9120
```

-continued

```
ggtgtcttcc cactataacc atctcttaaa ctatcttcct ttgtttgtag ggtcccatgg    9180
gtccccgtgg tcctcctggt cccctggaa agcctggtga tgatgtgagt atacacgagt    9240
agacaaatga ggagctgcct cctttgaaag ggcctggaga gggtgtgtgc ttggggagtg   9300
acagggaggc acccagggtg gaggtatctt gaggagcaag actgggcagt cccaaaccct   9360
gacgccatct cctatctata tggccactgt gactgtgctg gcaagttccc tggggaccgc   9420
tttggatcca aggggaagac aaataattaa aacatcatta gccccaggaa gggaaattga   9480
gaaatgagag aagggagaga aaaaatacaa ggcagaaaga tgtagagaag gaaaaacaaa   9540
gaaagaagcg ttcaacaacc cagcattatc ttaattgtaa atgagttaga aaaagcacag   9600
cctgagtcag gatgtctaca aaggatgcaa acgaaatgaa gagacaagaa ttggcactct   9660
tgtgctattt ttatgaattg cattagacag taaaagtctc ttgaggttag agagagcaca   9720
tacagtcagc agaacctagg agaggagaga aaaagcctct caggggaagt tggaggctgg   9780
tgaggacaga ggagcttgcc catgggctat gcatgtgtcc aaaagaataa atggtgaccc   9840
atgaaaggca tccaggcacg tggagtctga aggaggtgag ggagatgagt gagccggtag   9900
gcaaaggcat ggagggctgg aaggagggaa gccctctggg gtgccccac tatgctactg    9960
cgtctctgag gaagctggga tatctctctc tctcccttca gggtgaagct ggaaaacctg   10020
gaaaagctgt tgaaaggggt ccgcctggtc ctcaggtaaa cgccaccgtt cccagcctca   10080
ggcatctttc ctagcgtctc cctccctgtg gccttaaaca cagtgcatcc agttcaatga   10140
ggtcacttct gagatgaaac gccagtagcc cctatattta tcacgaccat gtttgtaatt   10200
tccactcagg ctctcatgag ggaggctggg cagttgttat ttataccact ttgcataaaa   10260
tgggggtac ggggagggt ggtctgggtt ttacagaaag agctgtccaa gtgtggggat     10320
tcgagacaac gccctggtgg cccaagggaa ctggaggccc tcctgcagcc cagggcagct   10380
ttccactgtt attttactct gtgctctgaa cacctccact ttggattgca gggtgctcgt   10440
ggtttcccag gaaccccagg ccttcctggt gtcaaaggtc acagagtaag tatcacgggt   10500
gagaaggttg gaaggaagag atgcctggtg ggagagaaaa gcactttggg gtgcgtgcat   10560
ttcttccaac ttgggtttcc cagaagtctg attgaacatt ttctcttgtt ccctagggtt   10620
atccaggcct ggacggtgct aagggagagg cgggtgctcc tggtgtgaag gtgagaggcc   10680
agaaagtaca atgggatggg gaggagggag acaatgagga gccctcttc ctagccaggg    10740
agacactgtg gagctcagtg gaactagctc ctcagaacag ccttggctgg gaacaccagc   10800
cctacatcct gatgggccaa cagcaggcct ggagagctca gggcattgtc cctcacagga   10860
ctgaagtttg tgtcagtgcg agctgagatg accagggctt ttggcgtctt ccctaggagt   10920
ttgctggcgg ccaagaatgg ggtcccagac actgaccttg tgcatcattt ttccagggtg   10980
agagtggttc cccgggtgag aacggatctc cgggcccaat ggtaagtatg gacaccctcc   11040
aggaaggttt atcaaagact cttcagacta tcagatggct gcaaagagct ccctttgtgc   11100
aaagttcata ttctgtgttg tagatttcat ctgattgtga gcaaaaagca aatgtatta    11160
gacagatgat ttgttcaaga tttcaccaac atttccttaa gatacccatt ttatcacact   11220
aaagatgctc ccatttaaaa aaattctgtt gagtctcaac attttgtcaa gctcatctac   11280
tgcaaggagc aaggtgtgct tgtaacaaag gttcccaata ggtagcaaca ggaacattcg   11340
tgtgttccgc ctgtggagaa aactgttggg tgtgatctga ggcatcctgg ctagtcaagg   11400
agccagcacc atcaggaggt ccttgttttc ctgggtgtgg gcatcctccc tctcctctgg   11460
tatccgcaaa gggcctgcag gtagaaatgg tcaccctgag caccgtaaag ccaactcatg   11520
```

```
cttaggctgt cctggtgtgt gttccagggt cctcgtggcc tgcctggtga aagaggacgg    11580
actggccctg ctggcgctgc ggtgagtaat tgacaaagcc aaacaccacc atttgccgag    11640
cactttagag tttacaggtt tgtttctctt gaccctcgaa acaaccctgt gaggcatagg    11700
gagtattgtt atcccttaag aattcacccc cagtgtgccc atcaaaactt cccaggctga    11760
gtctgcacag ttgaaggagg aaggatagga atgggaggt cgatgggtga aagcatgatt    11820
ctcttaacca gtccagatta tcaggtaatc ccttcaacaa ccaccaccca ctccctgggc    11880
aatccagctg gagtttacag acagacttag ctggctatag caccaccgtg ctactctctg    11940
ttcttcctgg ttgctcaaat gccctagaaa agtggaacag gtgagcatca actcacaggg    12000
ctctatgctg gctgctgctg tgagggatgt tatgctatag taccaggggc caccattcca    12060
taggcacttc ctgtgtttaa taccctatat gctttacttc atctcatctt cctccatatc    12120
ctgagaggtg gttctattct tctccccatt ttacggatga aaaaccgag acacagaaag    12180 gtgaaatagc ttaagataaa tagtgccttg cagccttaga ctctggtggc ctctagttaa    12240
tgtgggaaat taagggtgag gggattggca gctgatggag ggtgcagggt gccagacaga    12300
ggcgtttagc tctgattcct tagcaataga gagtccttgt aggcacttgg tcaggcgagt    12360
gatgcgatga aagctgtgtt taagaaagat tatgcttct gctgatttca taccccccaac   12420 acccaagctc tgaggcccct cctcacaggt ccttgcaggg ctggccaaaa taaagcagct    12480
tcactccgtt gtgctgcttt ccagctaatg tgtctgtttg gcagaagttt ccctcaaagg    12540
cagatcagtg aaataagcag aagcctcgac ccccctttgt cagccagagc tgctgaagtg    12600
ccttgcccca gggtcacttt gtgtgagggg attagagagc actggggctg ccaagaaaca    12660
ctgccgtttc tacagattag caggatgctg gcttgtggcc ttttagcgag gctcagagct    12720
gcggtggccc tagtctgcat gggctaaaga caagctccat ctcctgtcct tgttccctcc    12780
ttcctgggca cagccgccct gcttcttggt tctctctgtt ggttcctgtc cgcacggtag    12840
ttaggctggc agcgtgtgta ggatttggct tagaagattg acaacattgc ctttgagccc    12900
ttctttgcta ctcctccctc tcccctccca tcagactcct ctctggagtc tgctctgcga    12960
ggcctctgct ctgtggtatc ccagcagcct tctcagcctt gacttccaga aggggctgt    13020 gcagtgtccg gggtgtgcag gcccagaca cggggtaggc tcatggagat ccaagtgctg    13080
atctagtgtc aaggctggcc tggagactgg gctgggttgg tgtctgcctg ctgtggtcat    13140
gtgccctccc ttgggcctgt atcctctctc cagacttgct gcaggagag gtggcagatg    13200 tcagcctagt tctggcctct cagagcagca tggcagctcc ctttcactca ggcccaggct    13260
gggccctcct gctggctgac ccctggggag agggtgctcc agagctcccc aaggaactgc    13320
ttcccgaagc agccaggcca gcccagaggg gctgtggcca atcctgaagc tttatgttcc    13380
tgctgacatt ttttctaagt tttctcttgc tttcctctta aatgccaatc tggagagtct    13440
ccgttaggag aaatggaccc cagccaggaa gaagagttga gttgtattta aaacacgagc    13500 tcccccctaaa gcatccttct ttagcttcta aggagaggca gagactgaca ggcaggactc    13560
agcaggaaaa ggtaccccc tgacctgctc agtcaggccc taggcccagc tccacccagc    13620
ctgtggcccc cagagtttcg gtaaagagtt ccctgggcct taaggaacct tgagagagca    13680
tttgaggggt gccaccacaa acttggcaga aaaaaccctc cccctccaag tccagtccta    13740
gagaaggagc tggcaacctt gccttgcttt gtaagcaaaa gctcttagg gcttgagctc    13800 agatgtagtg tttgagctgt ggctggtgcc ctgccccatc agggagccaa tggtagacat    13860
```

```
cctatgggca tctttgtttt ccgtaagagc aggctgtctg gggatgggcc agaggaagag   13920
gcaacctgga gtcaaccaag aggaggcctt aaccaagcct taaccacaga ggttaaccaa   13980
gccttgaaag cgcttccccc tgagcaggca ggaagcactg agtccacatg gttgcctcgc   14040
tgtttcattt ccttacactc aattctctca gtctttaaat gatcacttgg ccttgaagtt   14100
acggatattt ggggtctgaa ctgaagttga agaaaagaga aaatgattta agctttgttt   14160
aagattaggg gccaggtgcg gtggctcacg cctgtaatcc cagcaccttg ggagcctgag   14220
gcgggtggat cacctgaggt caggagttcc agaccagcct ggccaacata gcaaaaccca   14280
gtctctacta aaaataacaa taaaaaaaat agccaggtgt ggtgacacat gcctgtaatc   14340
ccagttactc aggaggctga ggcagaattg cttgaacttg agaggtggag gttgtagtga   14400
gccaagaccg caccactgca ctccagcctg gcgacagagc cagactccgt ctcaaaaaca   14460
acaacaaaaa aagattagaa gaagcccatt actgccttct ggccacccac tcgcacagac   14520
accaaaactg cagcccacac ctcgccatcc tcgtgctctg ccctgggaca ccccaggcac   14580
agtgtgtcct tcgttttctg taagggtggg ctgggagcag ggacggacag ggcctgtggg   14640
cacctctcat ggtcacttcc ttcttgctca cagggtgccc gaggcaacga tggtcagcca   14700
ggccccgcag ggcctccggt aagttcattt catcctcagc aggtcattgt tgctgtgctt   14760
taagtcccgt taagcagccc aaggcagtct gcagggtgta ttgggtgcaa ccacagcagc   14820
actctgatgt ctactggaaa gggggaggaa agagaagaag tttgtaaata tcaattgagc   14880
atatcgataa caagctttga agcatgggct cattttcctc agccatcctt tcagcagtct   14940
ttttagagga gggaggtcaa aggagtttct gcttctcacc acagatgtag tcagaaactt   15000
gctttgcctt ctgaagccag gcaaagtttc ctggggacgc tggcaatggg gacaattttc   15060
atccaaggcc ttttagccac aatggatatg gagtgaaatc agtacagagg agggaaggag   15120
tgtgaggtgt cggggtggct cgctttggag gccagaactg gcattcacct ctcttctcat   15180
ccgcctactc tctccagggt cctgtcggtc ctgctggtgg tcctggcttc cctggtgctc   15240
ctggagccaa ggtacgtgcc ctgttgtcca gtcaggaact tctgggtgcc gagaagctgt   15300
cctttccccg taaccctgc tcattgctcc ctcaacaacc acctgctccc ttctgagaag   15360
tagctcccca ccaccccacc cactggcccc tccatccagg cagggcaaaa agccagacac   15420
tcgcagtctc acctggaggg aaagtaagac agaagataaa atgtgggaga tccagttaca   15480
actttggagt ggggaaaggt ggacagagaa gaagacgggg atacaccata ggcctggcag   15540
gggcagaagg ccaggagtgg cagcacaggg aagcaaacct aggggagacc caacagctga   15600
gcaagctcgg ggccctgacg ggcactggag ggaactgggc agggaaaagg gcacaggcag   15660
ggagcccctg ctcccctctg ggtttctgct ttatttgggg tgcctggctc ttccaaacca   15720
tgttaacgga gttctctgga ggattactag aggccagtgg gaggccagcc agttcaggga   15780
caggcctcgc agcccaggaa ggattccagt gtgaacgtcc ctgggaatga ataaggagcc   15840
tccatgtgtc actggcatca ggttgctttt cccctcctgg gggtttccat ggcaaccaga   15900
cagtgtctga ggtcccggag ccgggtgaag gagacccatt gtgaagaggg acagcggaag   15960 gtgaggggg ctgaccttt gaaaataata attaccacag tgaagcagga atgttctgag   16020
aagaaacctg aggaggctct gccctctctc caggtcagca gccctcccca gggactctgc   16080
catctagagt gggttgtaat tttcaggaaa aaatgaaagt aaaagcacaa gccattttgt   16140
ggggaggggg cttgccagag gcgcccgcta agggaattg ggctgtattg agagcaggga   16200
ggggcagagt ccccatgtgc ttttgccttg gctttctggc ttactgagaa cagactgggg   16260
```

```
ccggagccag ggtgtcactg ttcacccgtc agccagatgg gagtgaggtg gtgctctgag    16320
ctgggatgtt cagagactta aagggacct cagctcctca ataaaataga aaaacaggag     16380
gtgggggaga gagcggtgtc cgtccatcat cccacggtgc caggatggca gggtccccag    16440
cccacgcttt tctgatggtg tcgatggaac agcaggttgc ccattgctgt agtatgtagc    16500
tgtgccgtgg catgtggagg ctcactgtgt agagatgagg taagcagtag aggaggcagg    16560
cgtgggaagt catcaagtca tcagctcggt caggcaggga gaaaaacggc agcgtgaact    16620
gtgtgtgaac gcacatgttc atgtgcaggg ttgggtgcat gtgcataatt tagtgctgtg    16680
cttgcagctg gccctgagct attgcccacc cactagaggt ctgtgtcccc tctcttcttc    16740
ttcatttcat cctccctgtc tcttcccagg gtgaagccgg ccccactggt gcccgtggtc    16800
ctgaaggtgc tcaaggtcct cgcggtgaac ctggtactcc tgggtcccct gggcctgctg    16860
gtgcctccgt aagtgcagct tctctttggc ctgggggggg ctggggtctg tggctttgga    16920
actcttgact ctgtactttg ctctgacagt tgtgggctcc aaccaccaaa ccttcattct    16980
ggcccaatgc ctgtccccac ctctagatgt attcccttct atcccatctt cccctttgaaa   17040 cacatagtgg gaatgtccct gaaatggaca gcacctatgc caggtccctg gatctggatc    17100
ctggagggct ggaggtggtt gggttcatt cttttgctgct tatttgacaa tgtctccctt     17160
ttcagggtaa ccctggaaca gatggaattc ctggagccaa aggatctgct gtgagtgttg    17220
cccgtggact ttgctacccc aggagagccc agtcctgcct ctcccctctc ctgacacccc    17280
tcccttcttc tcatgcccac agggtgctcc tggcattgct ggtgctcctg gcttccctgg    17340
gccacggggc cctcctggcc ctcaaggtgc aactggtcct ctgggcccga aaggtcagac    17400
ggtaagagcc caaagtgacc cccaagttcc actgacatct ctggagtcaa accccatcac    17460
ccctctttcc catgctctcc tgccctggcc tcacagcggc ctccatccga gggcatcttg    17520 aacagggggtt ctggggaggg gcaggctccc tggagagaat ctggtgtgag gacctgcctc    17580
tcttttcaag ggtgaacctg gtattgctgg cttcaaaggt gaacaaggcc caagggaga    17640 acctgtgagt atctgccccc aagcccttgt cttctctgct gctgttctat gaggcacagg    17700
cctcagcccc actgacccac cacctccctc ctccagggct ctatcccca atctgggtcc    17760 tttcagatta tgcctggagg agacttaaca gggctgagaa ggcccagata cagcttcagc    17820
tcccatcctt ggtttggcta gtgtgaacag ttggatcttt agccctctc acttccctct    17880 gccctgccat ggctcgtcct ttatggcctc tcgtcctcaa gccccccccc agccctgaaa    17940
cagttgccaa ggctacttcc ttcatactct gagtcgaggc ttgctccaag gccaggtgaa    18000
ggctcactct gtttctcttt tttgctggtc ctcaggcccc tgctggcccc cagggagccc    18060
ctggacccgc tggtgaagaa ggcaagagag gtgcccgtgg agagcctggt ggcgttgggc    18120
ccatcggtcc ccctggagaa agagttaagt gaatgtggag gctccatccc atgggggcctg   18180 tgacctcgag agggaagtgg agtccttgtg gtccgtgttc tggtcaagtc tcgtgacttt    18240
tccgcatgtc atcctcctct ttctccatcc acaccgcggg gagagggagt ctgatcctga    18300
tttgtgccgc caaccaccag actgacatga aatagtctga gctccttccc aggaagcggg    18360
gcaggctcca gaagttaacc tctgagaatc ctgcaggcca cagctactgc tccccagaaa    18420 ttgggggttgg tgggttagtg ggatggaccc actggagcct ggctgggttg gggctgttct    18480
cactcactgc ctctcctccc tgtggctcct tagggtgctc ccggcaaccg cggtttccca    18540
ggtcaagatg gtctggcagg tcccaaggtg agtgggagaa gaggggctgg ggtccctccc    18600
```

-continued

```
tgcatcgctg aggtcacatg gtatcccact gactccctgt gtaccctttgt agggagcccc   18660 tggagagcga gggcccagtg gtcttgctgg ccccaaggga gccaacggtg accctggccg   18720
tcctggagaa cctggccttc ctggagcccg ggtaagtagc agagctgctg ttgcccttgg   18780
cttcagaccc tcaggcccct cctggctggc tccttccagc cctgcactgc caggattggg   18840
aggtcctggg gccggctcct gaccccaccc tcttctctct cctgaacaaa gggtctcact   18900
ggccgccctg gtgatgctgg tcctcaaggc aaagttggcc cttctgtaag tctatcctct   18960
gagggctgct aggagggtgg gggatctcc ctggggaagc aagggaaaag agagatggag   19020
tttgggttag ggaggcctga agtactgtga attttgagaa ttgtgacagg gggtagatgg   19080
taggcactgg ggccagatgt aacctgtgca gtagctgtga gcactgaaaa tgccacccca   19140
gtatgcattc ggggcttatc cttgggggaa tgatgacatc gtgtgtgcac tttctggggc   19200
agctttctaa gctcagcggt gtcttgttgt agatgggccc atgggtgtga tgtggtcaat   19260
cctagatgct gagcatgtgt ggctggtgcc tagtcctggg cctgccatgt aggcccttag   19320
tggatgttgg gtggatggat gtggtcagag tgtctatgtt ctgagaatgg tgttctgtct   19380
ttcagggagc ccctggtgaa gatggtcgtc ctggacctcc aggtcctcag ggggctcgtg   19440
ggcagcctgg tgtcatgggt ttccctggcc ccaaaggtgc caacgtaagt aataatttgc   19500 tcttctatttt ccttccatgt ggtgctacct acctccctgc cctcttgggg aaagggctgg   19560
gtcctgagta gagtttaacc agggacagtg atgagtgggg ctcctgtgcc atgggtggca   19620 gtggggtct gtatgtgatt tggggaaaat ccatggcccc acagagcctc ggggcattgc   19680
ggccataatt gttccatgtg gcagtgccca gcaggctggt tgccattatg gcccctgaac   19740
agaagagaag ggctgatact ttgctttatc ttggctgtcc atcaggatgt ggccccaggc   19800
ctcagtccct gcagcccgct ctgcccccaa ctccctccca aaccatccgc ctcatggccc   19860
tgccctctct ttccttcagg gtgagcctgg caaagctggt gagaagggac tgcctggtgc   19920
tcctggtctg agggtaagta tccttccccg ctgcccatga cttggtgttg gccgggcatc   19980
tgcagggagg acaggggaac ggcctcccca tggcatggtc ccgggacccc tcagtattga   20040
gtgttgatct ctgtggctga gccccatgct ggctgggccc tttgggtgtc tacacaggga   20100
gacttctgtt tgccattggt cagcaggccg gggagctggg gaaggcttcc atgctgagaa   20160
cagctaagaa aagacggggc ctgggaagga agggagggga aggtgtggaa atggagctca   20220
gctggggtac cgtggaggtc tggaaactct gggccagaag tacctttgcc caatcctagg   20280
gggactgcaa gtgggaagaa aagcgtgtca ttgacttttc ttttttctctt ctgtctaggg   20340 tcttcctggc aaagatggtg agacaggtgc tgcaggaccc cctggccctg ctgtaagtac   20400
ctgcccagcc tccccaggtg gccctggggg caggggctgg gaggggtggg ggtgggagag   20460
cccatccatt aatggagctg acagatgtga atgtgggctg agctgataca ccagactcac   20520
tctgagctga ggcagggtgt cccaggaggc tgtgtggacc cacattggtg gagaggagtg   20580
tgggtggctg atgggagtgc agggaggcat gcatgcactg tctgagtggt gcaggaagac   20640
gcctgtgctg cccaccctgc tgacctcccc tgggccctac tagctgtggc tctcagggtc   20700
tctggaacac tggctcagct cacctttttct tttccactgc agggacctgc tggtgaacga   20760
ggcgagcagg gtgctcctgg gccatctggg ttccaggtag gtggctggac caggctctct   20820
gtgcagtcct ttgccatacc cagggctccc tgggacagca gcaggcacta tcggtggagg   20880
gcccacacct cttgcagggt gccaggcatc gagccttccc tgcaccctg gctgtcactg   20940 ctgctgcttc ctttctttgg gtctgcccta tactgtgcct ccctggggc cagggcagca   21000
```

```
aactcactcc tttgctaacg cttgtcactt cggcttctag ggacttcctg gccctcctgg    21060
tcccccaggt gaaggtggaa accaggtga ccaggtgagt atgggctct ttggacctgc       21120 aacctgttta gatgggaagg tcttttctga tgcctaggag gcaagggcaa gagggcatga    21180
ggagccctgt gaggcctggg aatgtcctgg acccatgtcc cagcctccac agatgacaca    21240
atcccccatg ggaggagtga tattcagccc tgctgtggag aattgttcag ggtctgtga    21300 tatgaagcct tcactctcac acatctttct ttgttctcca gggtgttccc ggtgaagctg    21360
gagcccctgg cctcgtgggt cccagggtga gtatcctgtt ggccaatgcg ggctgcctcc    21420
ttgggcctgc cctgggtcct atgctcctgc tcctttcccc acctccctgc ttctccctgg    21480
accttctccc ccactgctgt tggttgatca cttcttggtg tctctgccgc agggtgaacg    21540
aggtttccca ggtgaacgtg gctctcccgg tgcccagggc ctccagggtc cccgtggcct    21600
ccccggcact cctggcactg atggtcccaa agtaagtgag gctgcatcct gtaggggtct    21660
tcgtggtagc ctgggagtcc cactgagcag ggagaagagg agcgggctca ggaggaatga    21720
agaacagaag tgggggagc tggaaaggag gtctacatgg gaggaaggga aggaagaggg    21780
gtttggggcc ctggttaccc aggctccatg aacatgggtt cagggagagg tgctgtccac    21840
tacagactcc ctcttacctc cctccccagg gtgcatctgg cccagcaggc cccctgggg    21900 ctcagggccc tccaggtctt cagggaatgc ctggcgagag gggagcagct ggtatcgctg    21960
ggcccaaagg cgacagggta agtactgagg ttacagcctc tcaccaaagc tgtggctttg    22020
ccacattcct gccccttgtg atcgcttccg ttcccttatg gcacctggtg atgaaggttt    22080
ctgttagccc tttttgagga gcttaaagac tcctttccaa agctccctgc cttttagtga    22140
catcctttcc cctgttcctt catctcaccc ctgctgctcc tcacccaccc tgagaccaca    22200
gcaaattcct cttgggcagg gactgggctt tccctagcac cccagcctgg gtgggactga    22260
gcaaaccatg ggggtcctgg ggtgcctggc tgaggcggct ggttttctct tccctcaggg    22320
tgacgttggt gagaaaggcc ctgagggagc ccctggaaag gatggtggac gagtaagtga    22380
atgcgggctg ctggactgct gggcattagg atcctagccc tgcacccagg agagcaggag    22440
agagggctgg gcagtctgcc actggggtcc ctggtcctgt ctctgtcggg gctgggcaac    22500
tgcagggact tctctgttaa aatggggcca gagggtaagt gggagctctg gaggcggtgg    22560
gagcacgcac caaggttggc ttggtgccgg gccgcacgtg ctcggctggc tcagcctgcc    22620
tccctcacct ctacctgctc tccccgcagg gcctgacagg tcccattggc cccctggcc    22680 cagctggtgc taatggcgag aaggtgagtc ccggctcctt tcctctccac accttgcctc    22740
cctgtcacac ctccttctta tctcctgcca aggcggttc tgtcttgtcc tccctcacca    22800
ctgtcaccct cggccaaggc cgtaggagtg aagaggggc cctctcagaa gtgaagccgc    22860
tggcagtgtt ccctgttggg tggggcaact gggctgggt aaacacacat tcagcagagg    22920
ccctcgagag ggtgcgggta tgggctgcac agtaacacag gctgtgccag ggggacctgg    22980 agccccttc ccacgagcaa ggcccccaa atgcactttg ccctctccca ctctgcctcc    23040
ccaccttctt accccagctc ttcctccctt ccccacccctc agggagaagt tggacctcct    23100
ggtcctgcag gaagtgctgg tgctcgtggc gctccggtga gtgtctgccc ctctgagcct    23160
ggctctgccc gaggcccctg ggaaccagag agccaggag tcagtgcagg ccctcatgct    23220
gcctggtggc cctgtgtgct gccaggcact ggctccctcc ctaccgctg gtctagggt    23280 gggaggagag atgggaaggg aaggggaag gcacgtcact cccatcatgt gttcagggtg    23340
```

```
agggcttttg ggttaacaga gcctctgcct gcgttcagga ctaaggctgc tttcagatcc    23400
ccgtctctgg ggaacaggag gctgggcagg gcccaagggg ctcttggagg ggagcagaag    23460
caggtcaggc agcggggcct gacctctcgc catgccccct tctctcacag ggtgaacgtg    23520
gagagactgg gcccccggga ccagcgggat ttgctgggcc tcctgtgagt atctctgtcc    23580
atcctcctgg gtccctccac tcaggccagt tccacatcca gcaccctcgg gcatcggagc    23640
ttgtcaggga gggaaatgga tgctcctctc ctctcctttc ccgcctccat actaatagaa    23700
ccatcatgtc cagaccagga cacacacgca gatactcaca gagtctcctg ctcttctgga    23760
agagctccag ggttttagcc tgcccctcat tcacctgctt cctccttccc attataggggt   23820
gctgatggcc agcctgggc caagggtgag caaggagagg ccggccagaa aggcgatgct      23880
ggtgcccctg gtcctcaggg cccctctgga gcacctgggc ctcaggtggg taacgctgca    23940
ctccaagaat tgttccctca aggaagggct cctggcgtgc agatgggaag ccccagcag     24000
gctgcgcaga ggatggttcg caggcctggg aacaccccca tgttggtaga aggagcttcc    24060
atgtggcatg tgggctgtgt gggtggggtg tagggactga cagagtacag gctggccaca    24120
gccagccaga accaagctgc tgatctcctg gggaggaggg ggcggtggca ggaagagctt    24180
cccgggaggc cagaccccag accggttctg tggttgcctg acaggcttct cctagaacac    24240
aagtctcctg tggcagaggg gacagagctg cctgtggcag cctcttcagg ctgggttttt    24300
agtgccaaga aagctgcatc ttcgaaaacc tcaggggtcc attgttgggg ctcagacaga    24360
agcccaccgt cttccttggg ccactgggcc tcactgtctc cctctttcct ttccagggtc    24420
ctactggagt gactggtcct aaaggagccc gaggtgccca aggccccccg gtgagtgagg    24480
cctctgacac cccaccctgc acctcacaaa gaggcctggc cccagaggct cccatggcgg    24540
gggtgttctg ggatgccccc gactgttttc ccagccctgc gttggtcccc agcctaagcc    24600
cacccacagc caggtgggag agagggcgcc tgtgggctgg gtgcactgtg gtcccggatt    24660
ccccagcccg aggcttgtcc ctcgttcagc tccctgaagt gctgactgtg gaaaccggag    24720
gcagggaaac agcctgtgcc tgcttctatg accagacccg ggggcccttt ctccctccct    24780
ggatccccct tgctgctttg cagtccctcg ccctttccat accaggctct gagaccaccc    24840
ccgcccccg cccatttaa tctcaaacct cctgagggct tgaggttctc aggggctctc      24900
ctctccccac acagggagcc actggattcc ctggagctgc tggccgcgtt ggaccccag     24960
gctccaatgt aagtgatgct cctggcatga gaggcacagg caggcatgga atagcctggc    25020
ccagcaccca acagggtctg gagagctcca ggctggcctt cactcctctg agtccgttcc    25080
tgccccctgg aggagtagct aactgatcat ggggacctat cccctgaggg tggctggggg    25140
cagggttgtg gccctgctgt cagcaatggg tggctgccct gctggcttgg tgggcaggac    25200
agggctgcca tgattacctt catcctggac agatgtttct tgagcatgtt ctgtgcactt    25260
gtctgtgtgc tttaaagcaa gtccgcatgt cctgggtcgc tctcagggag tttgcatgga    25320
gggagcagtg gtgatgaact cactgggttc accagcgcca taggcagagg gagagagtgc    25380
tgggggcaag ctcaggggtc agaggggcag ggctggagcg gctcctgagg aaggggattt    25440
gaggacaaag ggaggaggga ggagagattc caggtagatg ggagaaagca agcaagcag    25500
gagctggaga agttggggct gtctgcccag agctgtctca catggtgaga aggttgcagc    25560
ggtagattgg ggttgggggg gttaagctgc ctgcccttag tgtggggagg tagagaagcc    25620
cccagagagg aaactgctgt cactgaggcc acagtgactt tggcagcctg gatgaggaag    25680
ggtgagatga gtcctcactt cccgcatttt ctccttctag ggcaaccctg gacccctgg     25740
```

```
tccccctggt ccttctggaa aagatggtcc caaaggtgct cgaggagaca gcggccccc      25800
tggccgagct ggtgaacccg gcctccaagg tcctgctgga ccccctggcg agaagggaga      25860
gcctggagat gacggtccct ctgtaagtcc ctcaccaggc ccatgccaag gtccctggga      25920
gcagggtcgt gagtggcttc tgagctcaca gagcatgggg taggagggag cagggcccgt      25980
ggggatgcca gggagcgggg ctgcacagac agagctgtgc tgagaggaca gaagaggctg      26040
ggccactgtc agttctcatc tcctgcctct cctctctcag ggtgccgaag gtccaccagg      26100
tccccagggt ctggctggtc agagaggcat cgtcggtctg cctgggcaac gtggtgagag      26160
aggattccct ggcttgcctg gcccgtcggt gagtgtgggg tatccctccc tccatccaag      26220
ctgggccctg cctgccaagg cttctacctc cctcagcacc ctcaggactg tcccttgtct      26280
gccctctccc tgaagggtca gtgggccctg gcagggg tg cttaccactt gcactcatca      26340
tccttgtctc tgtccctcca gggtgagccc ggcaagcagg gtgctcctgg agcatctgga      26400
gacagaggtc ctcctggccc cgtgggtcct cctggcctga cgggtcctgc aggtgaacct      26460
ggacgagagg tgagcagtga accccctgg ggtggccctg attggggaga ggggccctgt      26520
gagtctctgt gctgggtcag caaggacaag tcccagtcag ggccctggag aagggggtgg      26580
cagtgtcggc cgacaggcct gaaagcctag gtacaatggg aaggttgtcg gggagagaga      26640
cgggcataga gaccaagggc tgcttccgga aggaggaggg aaacttggtg aggaaacttt      26700
ggcttcaaag tgtgagtgag ttgggcagaa gaggagaggc ctgggcttct gagagggct      26760
gggggagcag aggggagat gggcaggaag cagctctaag tgcattcttg tttcactttg      26820
tccagggaag ccccggtgct gatggccccc ctggcagaga tggcgctgct ggagtcaagg      26880
tgagtgtctg gtgtctgtgt gtgcagtggg ttggggagga cattgcctcg ggcctgacag      26940
gtcagctggg ggtggcaggt tggaacaagt ctcatctcag cctagaagga ccttctgttc      27000
ctgtctcttc tggaacattc ttctctgagc ctgagacctc tctcctgaca gggtgatcgt      27060
ggtgagactg gtgctgtggg agctcctgga gccctgggc cccctggctc cctggcccc      27120
gctggtccaa ctggcaagca aggagacaga ggagaagctg taagtatcct gaattcagta      27180
aaagccgcct tccctgcgc ggtggggctg aggcagtccc tgggtttccg cagtctctgg      27240
actaaggagc agtggcctca gatgcagagg aggccccac ctgtcctggc ttttctctga      27300
cgctgcgctc actctctcct cagggtgcac aaggccccat gggaccctca ggaccagctg      27360
gagcccgggg aatccaggtg agtatccaag tgtcctgcac tgagtcccca ccagggatag      27420
gctgggaggg cagccagcct ccaggtggtt cctgggcctc cagccctgtg tttccgggga      27480
ttcctcagct tgggtgggac aggaggggc tcctgtcctg gccctgacct gactcaatcg      27540
gtgtctgtct tgttcccagg gtcctcaagg ccccagaggt gacaaaggag aggctggaga      27600
gcctggcgag agaggcctga agggacaccg tggcttcact ggtctgcagg gtctgccgg      27660
ccctcctgtg agtgtcactg cctgcgtggg acttcccgag gcctcctgcc acacagagcc      27720
cacttgagct ccctgtgctg ccaggacagc ttgggatcac cctaagcagt ttctaggatt      27780
tcctcagggc tggagggagg aggaagtgga aagggaatgg ggctgggaca taaagctgtt      27840
cccccagctc ccagaatata gatagatatg tctgtgctga ccgtggcctt ttgcctcttc      27900
cttctacaca gggtccttct ggagaccaag gtgcttctgg tcctgctggt ccttctggcc      27960
ctagagtaag tgcatggag ttggaagatg gaggggcc ttcagagagt gtgggcctgt      28020
gttcccatgg ggagggaaat gctgctgctt ctggggaagc tgtgggctca gggtcctca       28080
```

```
ctcagtaatg ggggcaggac tggctcatgt gcctatggcc agaaaagcgc ctgaggccac   28140
aatggctgta agacaaacat gaatcagcct ctcgctgtca gacagaacag cattttacaa   28200
agaggagctt aggagggtag gcaagccatg gagctatcct gctggttctt ggccaaatag   28260
agaccaactt agggttccat gactgagcat gtgaagaact gggggcggag tggctggtgc   28320
tatcaggaca gccacctacc cagccccagc gactccccag ccttccctgt ggtgaccact   28380
cttccctcac gacctctctc tcttgcaggg tcctcctggc cccgtcggtc cctctggcaa   28440
agatggtgct aatggaatcc ctggcccat tgggcctcct ggtccccgtg gacgatcagg    28500
cgaaaccggc cctgctgtaa gtgtcctgac tccttccctg ctgtcgaggt gtccctacca   28560
tccgggaggc ttgagctctt ttttgctcag ggcctctttt agggcatcag cctgcagcta   28620
acagtgatgg catcctttat cctgaggtct cctcagaggt cacagggccc atgatcagtg   28680
ctgggaaact gaagagaagg gctaaggaag aaatagacat ggtgctgtgg tttccttggt   28740
cctcgcctgc tacacctccg ccccacccat ggggctggga agaggacac tctagtacat    28800 tctagcaaat ggggatggac atggaggggc actttcacac aatcctggct gatctctctg   28860
tttcctgctg cagggtcctc ctggaaatcc tggaccccct ggtcctccag gtccccctgg   28920
ccctggcatc gacatgtccg cctttgctgg cttaggcccg agagagaagg gccccgaccc   28980
cctgcagtac atgcgggccg accaggcagc cggtggcctg agacagcatg acgccgaggt   29040
ggatgccaca ctcaagtccc tcaacaacca gattgagagc atccgcagcc ccgagggctc   29100
ccgcaagaac cctgctcgca cctgcagaga cctgaaactc tgccaccctg agtggaagag   29160
tggtaagctt ggagaacagg atcccctgcc ccgggaagca gggagtcatc ccttaggcct   29220
agcagcaagg gaggagatgc cccctagtac agggcagagc tgggcctgga agtttccgcc   29280
agagggttcc tctcttattt cacagcagag aagctgcagc cctggcccct gtcctgccat   29340
ggctacctgg ccgaggtgac ctcagggtgg actccatcca ccagctgggc actgcttctg   29400
ctctctttgc atgtgttctt ccttagggct ggacttagct catgcagatc tccctgcccc   29460
tgcatcctcc caggtccccc tcctttcagg ccacatgtga acctcatccc ttgtccctgt   29520
aggcctctct gtctctttca gtcaggcctg ggtctctcaa gcttttgtgt ctgtgcctgt   29580 ctgagcccc atgggtgctg cctcttcccc ctgcaggaga ctactggatt gaccccaacc     29640
aaggctgcac cttggacgcc atgaaggttt tctgcaacat ggagactggc gagacttgcg   29700
tctaccccaa tccagcaaac gttcccaaga agaactggtg gagcagcaag agcaaggaga   29760
agaaacacat ctggtttgga gaaaccatca atggtggctt ccatgtgagt acctgggtgc   29820
cctagatgat gagcagagat ggctcctcaa actctttctt ttctttctcc ctggaagctt   29880
ttagcacctt ccccatattt tcctccagtt ttctgttggg cttgagagga gggaaagagg   29940
aggaaaagta ttttttcccc acgtggaggt gggaaaagag gtcctctgag cttgctccac   30000
tcctggaagc aaaaatgtcc aactagctcc ctgctgcccc agtacccttg aggtccttga   30060
accatgaact cttggcagcc cctacagccc ctggtcccat tgaatgccag ctcccaggcc   30120
tcacactgcc gctctctgcc ccaacagttc agctatggag atgacaatct ggctcccaac   30180
actgccaacg tccagatgac cttcctacgc ctgctgtcca cggaaggctc ccagaacatc   30240
acctaccact gcaagaacag cattgcctat ctggacgaag cagctggcaa cctcaagaag   30300
gccctgctca tccagggctc caatgacgtg gagatccggg cagagggcaa tagcaggttc   30360
acgtacactg ccctgaagga tggctgcacg gtgagtgggg ctgccagaga gaagagctgc   30420
ctgtgcccaa accgcctgga gcagggctga gggttggccc gcggcagctg tcaggtccta   30480
```

-continued

```
aagtgacagg atcatcagag gcatgagttt gagggtcatg tagagaagat aggctgagtg     30540
acaggtgaga gagaggcaca tatcattcca tcttctccat tcccctggct caggggaaca     30600
aaaccctacc tggaacccag tgactactgt agaagtgttc tcgcaatgtg tacagggtga     30660
agaagcggtc acaggttggg agctcactgt ggggagtggg gaaggagggg aagggcaggg     30720
tggagaaggg ccctgccgct aaggatagga gttgaagtgg agaggccttt ggcaagccaa     30780
gaagaggtct caggagcccc ctcagtgtgg ttcaaccttg tgggctctga tgctcgccag     30840
tttgttcagt tttgggcttc tgggcagctg gaactgggta gcaaggcatc tactgaacag     30900
agcctcctcc ttttttctcc cctagaaaca taccggtaag tggggcaaga ctgttatcga     30960
gtaccggtca cagaagacct cacgcctccc catcattgac attgcaccca tggacatagg     31020
agggcccgag caggaattcg gtgtggacat agggccggtc tgcttcttgt aaaaacctga     31080
acccagaaac aacacaatcc gttgcaaacc caaaggaccc aagtactttc caatctcagt     31140
cactctagga ctctgcactg aatggctgac ctgacctgat gtccattcat cccaccctct     31200
cacagttcgg acttttctcc cctctctttc taagagacct gaactgggca gactgcaaaa     31260
taaaatctcg gtgttctatt tatttattgt cttcctgtaa daccttcggg tcaaggcaga     31320
ggcaggaaac taactggtgt gagtcaaatg ccccctgagt gactgccccc agcccaggcc     31380
agaagacctc ccttcaggtg ccgggcgcag gaactgtgtg tgtcctacac aatggtgcta     31440
ttctgtgtca aacacctctg tatttttaa aacatcaatt gatattaaaa atgaaaagat     31500
tattggaaag t                                                         31511
```

<210> SEQ ID NO 2
<211> LENGTH: 5060
<212> TYPE: DNA
<213> ORGANISM: Homo sapiens

<400> SEQUENCE: 2

```
acgcagagcg ctgctgggct gccgggtctc ccgcttcctc ctcctgctcc aagggcctcc       60
tgcatgaggg cgcggtagag acccggaccc gcgccgtgct cctgccgttt cgctgcgctc      120
cgcccgggcc cggctcagcc aggccccgcg gtgagccatg attcgcctcg ggctcccca      180 gtcgctggtg ctgctgacgc tgctcgtcgc cgctgtcctt cggtgtcagg gccaggatgt      240
ccaggaggct ggcagctgtg tgcaggatgg gcagaggtat aatgataagg atgtgtggaa      300
gccggagccc tgccggatct gtgtctgtga cactgggact gtcctctgcg acgacataat      360
ctgtgaagac gtgaaagact gcctcagccc tgagatcccc ttcggagagt gctgccccat      420
ctgcccaact gacctcgcca ctgccagtgg gcaaccagga ccaaagggac agaaaggaga      480
acctggagac atcaaggata ttgtaggacc caaaggacct cctgggcctc agggacctgc      540
aggggaacaa ggacccagag gggatcgtgg tgacaaggt gaaaaggtg cccctggacc       600 tcgtggcaga gatggagaac ctgggacccc tggaaatcct ggcccccctg gtcctcccgg      660
cccccctggt ccccctggtc ttggtggaaa ctttgctgcc cagatggctg gaggatttga      720
tgaaaaggct ggtggcgccc agttgggagt aatgcaagga ccaatgggcc ccatgggacc      780
tcgaggacct ccaggccctg caggtgctcc tgggcctcaa ggatttcaag gcaatcctgg      840
tgaacctggt gaacctggtg tctctggtcc catgggtccc cgtggtcctc ctggtccccc      900
tggaaagcct ggtgatgatg gtgaagctgg aaaacctgga aaagctggtg aaagggtcc       960 gcctggtcct caggtgctcc gtggtttccc aggaacccca ggccttcctg gtgtcaaagg     1020
```

```
tcacagaggt tatccaggcc tggacggtgc taagggagag gcgggtgctc ctggtgtgaa    1080
gggtgagagt ggttccccgg gtgagaacgg atctccgggc ccaatgggtc ctcgtggcct    1140
gcctggtgaa agaggacgga ctggcccctg ctggcgctgcg ggtgcccgag gcaacgatgg    1200
tcagccaggc cccgcaggtc ctccgggtcc tgtcggtcct gctggtggtc ctggcttccc    1260
tggtgctcct ggagccaagg gtgaagccgg ccccactggt gcccgtggtc ctgaaggtgc    1320
tcaaggtcct cgcggtgaac ctggtactcc tgggtcccct gggcctgctg gtgcctccgg    1380
taaccctgga acagatggaa ttcctggagc caaaggatct gctggtgctc ctggcattgc    1440
tggtgctcct ggcttccctg gccacgggg tcctcctggc cctcaaggtg caactggtcc    1500
tctgggcccg aaaggtcaga cgggtgaacc tggtattgct ggcttcaaag gtgaacaagg    1560
ccccaaggga gaacctggcc ctgctggccc cagggagcc cctggacccg ctggtgaaga    1620
aggcaagaga ggtgcccgtg gagagcctgg tggcgttggg cccatcggtc ccctggaga    1680 aagaggtgct cccggaaacc gcggtttccc aggtcaagat ggtctggcag gtcccaaggg    1740 agccctgga gagcgagggc ccagtggtct tgctggcccc aagggagcca acggtgaccc    1800
tggccgtcct ggagaacctg gccttcctgg agcccggggt ctcactggcc gccctggtga    1860
tgctggtcct caaggcaaag ttggcccttc tggagcccct ggtgaagatg gtcgtcctgg    1920
acctccaggt cctcaggggg ctcgtgggca gcctggtgtc atgggtttcc ctggccccaa    1980
aggtgccaac ggtgagcctg gcaaagctgg tgagaaggga ctgcctggtg ctcctggtct    2040
gaggggtctt cctggcaaag atggtgagac aggtgctgca ggaccccctg gccctgctgg    2100
acctgctggt gaacgaggcg agcagggtgc tcctgggcca tctgggttcc agggacttcc    2160
tggccctcct ggtcccccag gtgaaggtgg aaaaccaggt gaccagggtg ttcccggtga    2220
agctggagcc cctggcctcg tgggtcccag gggtgaacga ggtttcccag gtgaacgtgg    2280
ctctcccggt gccagggcc tcagggtcc ccgtggcctc cccggcactc ctggcactga    2340
tggtcccaaa ggtgcatctg gcccagcagg cccccctggc gcacagggcc ctccaggtct    2400
tcagggaatg cctggcgaga ggggagcagc tggtatcgct gggcccaaag gcgacagggg    2460
tgacgttggt gagaaaggcc ctgagggagc ccctggaaag gatggtggac gaggcctgac    2520
aggtcccatt ggccccccctg gcccagctgg tgctaacggc gagaagggag aagttggacc    2580
tcctggtcct gcaggaagtg ctggtgctcg tggcgctccg ggtgaacgtg gagagactgg    2640 ccccccccgga ccagcgggat tgctgggcc tcctggtgct gatggccagc tggggccaa    2700 gggtgagcaa ggagaggccg gccagaaagg cgatgctggt gcccctggtc ctcagggccc    2760
ctctggagca cctgggcctc agggtcctac tggagtgact ggtcctaaag gagcccgagg    2820
tgcccaaggc ccccgggag ccactggatt ccctggagct gctggccgcg ttggacccca    2880
aggctccaat ggcaaccctg gaccccctgg tcccctggt ccttctggaa aagatggtcc    2940
caaaggtgct cgaggagaca gcggccccccc tggccgagct ggtgaacccg gcctccaagg    3000
tcctgctgga ccccctggcg agaagggaga gcctggagat gacggtcctc tggtgccga    3060 aggtccacca ggtcccccagg gtctggctgg tcagagaggc atcgtcggtc tgcctgggca    3120
acgtggtgag agaggattcc ctggcttgcc tggcccatcg ggtgagcccg gcaagcaggg    3180
tgctcctgga gcatcggag acagaggtcc tcctggcccc gtgggtcctc ctggcctgac    3240
gggtcctgca ggtgaacccg gacgagaggg aagcccccggt gctgatggcc ccctggcag    3300 agatggcgct gctggagtca aggtgatcg tggtgagact ggtgctgtgg gagctcctgg    3360 agccccctggg cccccctggct cccctggccc cgctggtcca actggcaagc aaggagacag    3420
```

```
aggagaagct ggtgcacaag gccccatggg accctcagga ccagctggag cccggggaat    3480
ccagggtcct caaggcccca gaggtgacaa aggagaggct ggagagcctg gcgagagagg    3540
cctgaaggga caccgtggct tcactggtct gcagggtctg cccggcctc ctggtccttc     3600 tggagaccaa ggtgcttctg gtcctgctgg tccttctggc cctagaggtc ctcctggccc    3660
cgtcggtccc tctggcaaag atggtgctaa tggaatccct ggccccattg ggcctcctgg    3720
tccccgtgga cgatcaggcg aaaccggtcc tgctggtcct cctggaaatc ctgggccccc    3780
tggtcctcca ggtcccctg gccctggcat cgacatgtcc gcctttgctg cttaggccc      3840 gagagagaag ggccccgacc ccctgcagta catgcgggcc gaccaggcag ccggtggcct    3900
gagacagcat gacgccgagg tggatgccac actcaagtcc ctcaacaacc agattgagag    3960
catccgcagc cccgagggct cccgcaagaa ccctgctcgc acctgcagag acctgaaact    4020
ctgccaccct gagtggaaga gtggagacta ctggattgac cccaaccaag ctgcacctt     4080 ggacgccatg aaggttttct gcaacatgga gactggcgag acttgcgtct accccaatcc    4140
agcaaacgtt cccaagaaga actggtggag cagcaagagc aaggagaaga acacatctg     4200 gtttggagaa accatcaatg gtggcttcca tttcagctat ggagatgaca atctggctcc    4260
caacactgcc aacgtccaga tgaccttcct acgcctgctg tccacggaag gctcccagaa    4320
catcacctac cactgcaaga acagcattgc ctatctggac gaagcagctg caacctcaa     4380 gaaggccctg ctcatccagg ctccaatga cgtggagatc cgggcagagg gcaatagcag    4440
gttcacgtac actgccctga aggatggctg cacgaaacat accggtaagt ggggcaagac    4500
tgttatcgag taccggtcac agaagacctc acgcctcccc atcattgaca ttgcacccat    4560
ggacatagga gggcccgagc aggaattcgg tgtggacata gggccggtct gcttcttgta    4620
aaaacctgaa cccagaaaca acacaatccg ttgcaaaccc aaaggaccca agtactttcc    4680
aatctcagtc actctaggac tctgcactga atggctgacc tgacctgatg tccattcatc    4740
ccaccctctc acagttcgga ctttttctccc ctctctttct aagagacctg aactgggcag    4800
actgcaaaat aaaatctcgg tgttctattt atttattgtc ttcctgtaag accttcgggt    4860
caaggcagag gcaggaaact aactggtgtg agtcaaatgc cccctgagtg actgccccca    4920
gcccaggcca gaagacctcc cttcaggtgc cgggcgcagg aactgtgtgt gtcctacaca    4980
atggtgctat tctgtgtcaa acacctctgt attttttaaa acatcaattg atattaaaaa    5040
tgaaaagatt attggaaagt                                               5060

<210> SEQ ID NO 3
<211> LENGTH: 1487
<212> TYPE: PRT
<213> ORGANISM: Homo sapiens

<400> SEQUENCE: 3

Met Ile Arg Leu Gly Ala Pro Gln Ser Leu Val Leu Leu Thr Leu Leu
  1               5                  10                  15

Val Ala Ala Val Leu Arg Cys Gln Gly Gln Asp Val Gln Glu Ala Gly
                 20                  25                  30

Ser Cys Val Gln Asp Gly Gln Arg Tyr Asn Asp Lys Asp Val Trp Lys
             35                  40                  45

Pro Glu Pro Cys Arg Ile Cys Val Cys Asp Thr Gly Thr Val Leu Cys
         50                  55                  60

Asp Asp Ile Ile Cys Glu Asp Val Lys Asp Cys Leu Ser Pro Glu Ile
 65                  70                  75                  80
```

-continued

```
Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
        115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

Gly Asn Phe Ala Ala Gln Met Ala Gly Gly Phe Asp Glu Lys Ala Gly
            180                 185                 190

Gly Ala Gln Leu Gly Val Met Gln Gly Pro Met Gly Pro Met Gly Pro
        195                 200                 205

Arg Gly Pro Pro Gly Pro Ala Gly Ala Pro Gly Pro Gln Gly Phe Gln
    210                 215                 220

Gly Asn Pro Gly Glu Pro Gly Glu Pro Gly Val Ser Gly Pro Met Gly
225                 230                 235                 240

Pro Arg Gly Pro Pro Gly Pro Pro Gly Lys Pro Gly Asp Asp Gly Glu
                245                 250                 255

Ala Gly Lys Pro Gly Lys Ala Gly Glu Arg Gly Pro Pro Gly Pro Gln
            260                 265                 270

Gly Ala Arg Gly Phe Pro Gly Thr Pro Gly Leu Pro Gly Val Lys Gly
        275                 280                 285

His Arg Gly Tyr Pro Gly Leu Asp Gly Ala Lys Gly Glu Ala Gly Ala
    290                 295                 300

Pro Gly Val Lys Gly Glu Ser Gly Ser Pro Gly Glu Asn Gly Ser Pro
305                 310                 315                 320

Gly Pro Met Gly Pro Arg Gly Leu Pro Gly Glu Arg Gly Arg Thr Gly
                325                 330                 335

Pro Ala Gly Ala Ala Gly Ala Arg Gly Asn Asp Gly Gln Pro Gly Pro
            340                 345                 350

Ala Gly Pro Pro Gly Pro Val Gly Pro Ala Gly Gly Pro Gly Phe Pro
        355                 360                 365

Gly Ala Pro Gly Ala Lys Gly Glu Ala Gly Pro Thr Gly Ala Arg Gly
    370                 375                 380

Pro Glu Gly Ala Gln Gly Pro Arg Gly Glu Pro Gly Thr Pro Gly Ser
385                 390                 395                 400

Pro Gly Pro Ala Gly Ala Ser Gly Asn Pro Gly Thr Asp Gly Ile Pro
                405                 410                 415

Gly Ala Lys Gly Ser Ala Gly Ala Pro Gly Ile Ala Gly Ala Pro Gly
            420                 425                 430

Phe Pro Gly Pro Arg Gly Pro Pro Gly Pro Gln Gly Ala Thr Gly Pro
        435                 440                 445

Leu Gly Pro Lys Gly Gln Thr Gly Glu Pro Gly Ile Ala Gly Phe Lys
    450                 455                 460

Gly Glu Gln Gly Pro Lys Gly Glu Pro Gly Pro Ala Gly Pro Gln Gly
465                 470                 475                 480

Ala Pro Gly Pro Ala Gly Glu Glu Gly Lys Arg Gly Ala Arg Gly Glu
                485                 490                 495
```

```
Pro Gly Gly Val Gly Pro Ile Gly Pro Pro Gly Glu Arg Gly Ala Pro
            500                 505                 510

Gly Asn Arg Gly Phe Pro Gly Gln Asp Gly Leu Ala Gly Pro Lys Gly
            515                 520                 525

Ala Pro Gly Glu Arg Gly Pro Ser Gly Leu Ala Gly Pro Lys Gly Ala
            530                 535                 540

Asn Gly Asp Pro Gly Arg Pro Gly Glu Pro Gly Leu Pro Gly Ala Arg
545                 550                 555                 560

Gly Leu Thr Gly Arg Pro Gly Asp Ala Gly Pro Gln Gly Lys Val Gly
            565                 570                 575

Pro Ser Gly Ala Pro Gly Glu Asp Gly Arg Pro Gly Pro Pro Gly Pro
            580                 585                 590

Gln Gly Ala Arg Gly Gln Pro Gly Val Met Gly Phe Pro Gly Pro Lys
            595                 600                 605

Gly Ala Asn Gly Glu Pro Gly Lys Ala Gly Glu Lys Gly Leu Pro Gly
            610                 615                 620

Ala Pro Gly Leu Arg Gly Leu Pro Gly Lys Asp Gly Glu Thr Gly Ala
625                 630                 635                 640

Ala Gly Pro Pro Gly Pro Ala Gly Pro Ala Gly Glu Arg Gly Glu Gln
            645                 650                 655

Gly Ala Pro Gly Pro Ser Gly Phe Gln Gly Leu Pro Gly Pro Pro Gly
            660                 665                 670

Pro Pro Gly Glu Gly Gly Lys Pro Gly Asp Gln Gly Val Pro Gly Glu
            675                 680                 685

Ala Gly Ala Pro Gly Leu Val Gly Pro Arg Gly Glu Arg Gly Phe Pro
            690                 695                 700

Gly Glu Arg Gly Ser Pro Gly Ala Gln Gly Leu Gln Gly Pro Arg Gly
705                 710                 715                 720

Leu Pro Gly Thr Pro Gly Thr Asp Gly Pro Lys Gly Ala Ser Gly Pro
            725                 730                 735

Ala Gly Pro Pro Gly Ala Gln Gly Pro Pro Gly Leu Gln Gly Met Pro
            740                 745                 750

Gly Glu Arg Gly Ala Ala Gly Ile Ala Gly Pro Lys Gly Asp Arg Gly
            755                 760                 765

Asp Val Gly Glu Lys Gly Pro Glu Gly Ala Pro Gly Lys Asp Gly Gly
            770                 775                 780

Arg Gly Leu Thr Gly Pro Ile Gly Pro Pro Gly Pro Ala Gly Ala Asn
785                 790                 795                 800

Gly Glu Lys Gly Glu Val Gly Pro Pro Gly Pro Ala Gly Ser Ala Gly
            805                 810                 815

Ala Arg Gly Ala Pro Gly Glu Arg Gly Glu Thr Gly Pro Pro Gly Pro
            820                 825                 830

Ala Gly Phe Ala Gly Pro Pro Gly Ala Asp Gly Gln Pro Gly Ala Lys
            835                 840                 845

Gly Glu Gln Gly Glu Ala Gly Gln Lys Gly Asp Ala Gly Ala Pro Gly
            850                 855                 860

Pro Gln Gly Pro Ser Gly Ala Pro Gly Pro Gln Gly Pro Thr Gly Val
865                 870                 875                 880

Thr Gly Pro Lys Gly Ala Arg Gly Ala Gln Gly Pro Pro Gly Ala Thr
            885                 890                 895

Gly Phe Pro Gly Ala Ala Gly Arg Val Gly Pro Pro Gly Ser Asn Gly
            900                 905                 910

Asn Pro Gly Pro Pro Gly Pro Pro Gly Pro Ser Gly Lys Asp Gly Pro
```

-continued

```
            915                 920                 925
Lys Gly Ala Arg Gly Asp Ser Gly Pro Pro Arg Ala Gly Glu Pro
        930                 935                 940
Gly Leu Gln Gly Pro Ala Gly Pro Pro Gly Lys Gly Glu Pro Gly
945                 950                 955                 960
Asp Asp Gly Pro Ser Gly Ala Glu Gly Pro Pro Gly Pro Gln Gly Leu
                965                 970                 975
Ala Gly Gln Arg Gly Ile Val Gly Leu Pro Gly Gln Arg Gly Glu Arg
            980                 985                 990
Gly Phe Pro Gly Leu Pro Gly Pro Ser Gly Glu Pro Gly Lys Gln Gly
            995                 1000                1005
Ala Pro Gly Ala Ser Gly Asp Arg Gly Pro Pro Gly Pro Val Gly Pro
        1010                1015                1020
Pro Gly Leu Thr Gly Pro Ala Gly Glu Pro Gly Arg Glu Gly Ser Pro
1025                1030                1035                1040
Gly Ala Asp Gly Pro Pro Gly Arg Asp Gly Ala Ala Gly Val Lys Gly
                1045                1050                1055
Asp Arg Gly Glu Thr Gly Ala Val Gly Ala Pro Gly Ala Pro Gly Pro
            1060                1065                1070
Pro Gly Ser Pro Gly Pro Ala Gly Pro Thr Gly Lys Gln Gly Asp Arg
            1075                1080                1085
Gly Glu Ala Gly Ala Gln Gly Pro Met Gly Pro Ser Gly Pro Ala Gly
        1090                1095                1100
Ala Arg Gly Ile Gln Gly Pro Gln Gly Pro Arg Gly Asp Lys Gly Glu
1105                1110                1115                1120
Ala Gly Glu Pro Gly Glu Arg Gly Leu Lys Gly His Arg Gly Phe Thr
                1125                1130                1135
Gly Leu Gln Gly Leu Pro Gly Pro Pro Gly Pro Ser Gly Asp Gln Gly
            1140                1145                1150
Ala Ser Gly Pro Ala Gly Pro Ser Gly Pro Arg Gly Pro Pro Gly Pro
            1155                1160                1165
Val Gly Pro Ser Gly Lys Asp Gly Ala Asn Gly Ile Pro Gly Pro Ile
        1170                1175                1180
Gly Pro Pro Gly Pro Arg Gly Arg Ser Gly Glu Thr Gly Pro Ala Gly
1185                1190                1195                1200
Pro Pro Gly Asn Pro Gly Pro Pro Gly Pro Pro Gly Pro Pro Gly Pro
                1205                1210                1215
Gly Ile Asp Met Ser Ala Phe Ala Gly Leu Gly Pro Arg Glu Lys Gly
            1220                1225                1230
Pro Asp Pro Leu Gln Tyr Met Arg Ala Asp Gln Ala Ala Gly Gly Leu
            1235                1240                1245
Arg Gln His Asp Ala Glu Val Asp Ala Thr Leu Lys Ser Leu Asn Asn
        1250                1255                1260
Gln Ile Glu Ser Ile Arg Ser Pro Glu Gly Ser Arg Lys Asn Pro Ala
1265                1270                1275                1280
Arg Thr Cys Arg Asp Leu Lys Leu Cys His Pro Glu Trp Lys Ser Gly
                1285                1290                1295
Asp Tyr Trp Ile Asp Pro Asn Gln Gly Cys Thr Leu Asp Ala Met Lys
            1300                1305                1310
Val Phe Cys Asn Met Glu Thr Gly Glu Thr Cys Val Tyr Pro Asn Pro
            1315                1320                1325
Ala Asn Val Pro Lys Lys Asn Trp Trp Ser Ser Lys Ser Lys Glu Lys
        1330                1335                1340
```

Lys His Ile Trp Phe Gly Glu Thr Ile Asn Gly Gly Phe His Phe Ser
1345                1350                1355                1360

Tyr Gly Asp Asp Asn Leu Ala Pro Asn Thr Ala Asn Val Gln Met Thr
            1365                1370                1375

Phe Leu Arg Leu Leu Ser Thr Glu Gly Ser Gln Asn Ile Thr Tyr His
        1380                1385                1390

Cys Lys Asn Ser Ile Ala Tyr Leu Asp Glu Ala Ala Gly Asn Leu Lys
        1395                1400                1405

Lys Ala Leu Leu Ile Gln Gly Ser Asn Asp Val Glu Ile Arg Ala Glu
    1410                1415                1420

Gly Asn Ser Arg Phe Thr Tyr Thr Ala Leu Lys Asp Gly Cys Thr Lys
1425                1430                1435                1440

His Thr Gly Lys Trp Gly Lys Thr Val Ile Glu Tyr Arg Ser Gln Lys
            1445                1450                1455

Thr Ser Arg Leu Pro Ile Ile Asp Ile Ala Pro Met Asp Ile Gly Gly
        1460                1465                1470

Pro Glu Gln Glu Phe Gly Val Asp Ile Gly Pro Val Cys Phe Leu
        1475                1480                1485

<210> SEQ ID NO 4
<211> LENGTH: 5060
<212> TYPE: DNA
<213> ORGANISM: Homo sapiens

<400> SEQUENCE: 4
acgcagagcg ctgctgggct gccgggtctc ccgcttcctc ctcctgctcc aagggcctcc    60
tgcatgaggg cgcggtagag acccggaccc gcgccgtgct cctgccgttt cgctgcgctc   120
cgcccgggcc cggctcagcc aggccccgcg gtgagccatg attcgcctcg ggctccccca   180
gtcgctggtg ctgctgacgc tgctcgtcgc cgctgtcctt cggtgtcagg gccaggatgt   240
ccaggaggct ggcagctgtg tgcaggatgg gcagaggtat aatgataagg atgtgtggaa   300
gccggagccc tgccggatct gtgtctgtga cactgggact gtcctctgcg acgacataat   360
ctgtgaagac gtgaaagact gcctcagccc tgagatcccc ttcggagagt gctgccccat   420
ctgcccaact gacctcgcca ctgccagtgg gcaaccagga ccaaagggac agaaaggaga   480
acctggagac atcaaggata ttgtaggacc caaaggacct cctgggcctc agggacctgc   540 agggggaacaa ggacccagag gggatcgtgg tgacaaaggt gaaaaggtgc ccctggacc   600 tcgtggcaga gatggagaac ctgggacccc tggaaatcct ggccccctg gtcctcccgg   660 cccccctggt cccctggtc ttggtggaaa ctttgctgcc cagatggctg aggatttga   720 tgaaaaggct ggtggcgccc agttgggagt aatgcaagga ccaatgggcc ccatgggacc   780
tcgaggacct ccaggccctg caggtgctcc tgggcctcaa ggatttcaag caatcctgg   840 tgaacctggt gaacctggtg tctctggtcc catgggtccc cgtggtcctc ctggtcccc   900 tggaaagcct ggtgatgatg gtgaagctgg aaaacctgga aaagctggtg aaggggtcc   960 gcctggtcct cagggtgctc gtggtttccc aggaaccccca ggccttcctg gtgtcaaagg  1020
tcacagaggt tatccaggcc tggacggtgc taagggagag gcgggtgctc ctggtgtgaa  1080
gggtgagagt ggttcccggg gtgagaacgg atctccgggc ccaatgggtc tcgtggcct   1140 gcctggtgaa agaggacgga ctggcccgtgc tggcgctgcg ggtgcccgag caacgatgg   1200 tcagccaggc cccgcaggtc ctccggggtcc tgtcggtcct gctggtggtc ctggcttccc  1260
tggtgctcct ggagccaagg gtgaagccgg ccccactggt gcccgtggtc ctgaaggtgc  1320

```
tcaaggtcct cgcggtgaac ctggtactcc tgggtcccct gggcctgctg gtgcctccgg   1380
taaccctgga acagatggaa ttcctggagc aaaggatct gctggtgctc ctggcattgc    1440
tggtgctcct ggcttccctg gccacgggg tcctcctggc cctcaaggtg caactggtcc    1500
tctgggcccg aaaggtcaga cgggtgaacc tggtattgct ggcttcaaag gtgaacaagg   1560
ccccaaggga gaacctggcc ctgctggccc cagggagcc cctggacccg ctggtgaaga    1620
aggcaagaga ggtgcccgtg gagagcctgg tggcgttggg cccatcggtc ccctggaga   1680
aagaggtgct cccggaaacc gcggtttccc aggtcaagat ggtctggcag gtcccaaggg   1740
agcccctgga gagcgagggc ccagtggtct tgctggcccc aagggagcca acggtgaccc   1800
tggccgtcct ggagaacctg gccttcctgg agcccggggt ctcactggcc gcctggtga    1860
tgctggtcct caaggcaaag ttggcccttc tggagcccct ggtgaagatg tcgtcctgg    1920
acctccaggt cctcagggg ctcgtgggca gctggtgtc atgggtttcc ctggccccaa     1980
aggtgccaac ggtgagcctg gcaaagctgg tgagaaggga ctgcctggtg ctcctggtct   2040
gaggggtctt cctggcaaag atggtgagac aggtgctgca ggaccccctg gccctgctgg   2100
acctgctggt gaacgaggcg agcagggtgc tcctgggcca tctgggttcc agggacttcc   2160
tggccctcct ggtccccag gtgaaggtgg aaaaccaggt gaccagggtg ttcccggtga    2220
agctggagcc cctggcctcg tgggtcccag gggtgaacga ggtttcccag gtgaacgtgg   2280
ctctcccggt gcccagggcc tccagggtcc ccgtggcctc ccggcactc ctggcactga    2340
tggtcccaaa ggtgcatctg gcccagcagg cccccctggc gcacgggcc ctccaggtct    2400
tcagggaatg cctggcgaga ggggagcagc tggtatcgct gggcccaaag gcgacagggg   2460
tgacgttggt gagaaaggcc ctgagggagc ccctggaaag gatggtggac gaggcctgac   2520
aggtccatt ggccccctg gcccagctgg tgctaacggc gagaagggag aagttggacc    2580
tcctggtcct gcaggaagtg ctggtgctcg tggcgctccg ggtgaacgtg gagagactgg   2640
ccccccgga ccagcgggat tgctgggcc tcctggtgct gatggccagc tggggccaa    2700
gggtgagcaa ggagaggccg gccagaaagg cgatgctggt gccccctggtc ctcagggccc   2760
ctctggagca cctgggcctc agggtcctac tggagtgact ggtcctaaag gagcccgagg   2820
tgcccaaggc cccccgggag ccactggatt ccctggagct gctggccgcg ttgaccccc    2880
aggctccaat ggcaaccctg gacccctg tcccctggt ccttctggaa aagatggtcc      2940
caaaggtgct cgaggagaca gcggccccc tggccgagct ggtgaacccg gcctccaagg    3000
tcctgctgga ccccctggcg agaagggaga gcctggagat gacggtccct ctggtgccga   3060
aggtccacca ggtcccccag gtctggctgg tcagagaggc atcgtcggtc tgcctgggca   3120
acgtggtgag agaggattcc ctggcttgcc tggcccatcg ggtgagcccg gcaagcaggg   3180
tgctcctgga gcatctggag acagaggtcc tctggccc gtgggtcctc ctggcctgac    3240
gggtcctgca ggtgaacccg gacgagaggg aagccccggt gctgatggcc ccctggcag    3300
agatggcgct gctggagtca aggtgatcg tggtgagact ggtgctgtgg agctcctgg     3360
agccctggg ccccctggct ccctggccc cgctggtcca actggcaagc aaggagacag     3420
aggagaagct ggtgcacaag gccccatggg accctcagga ccagctggag cccggggaat   3480
ccagggtcct caaggcccca gaggtgacaa aggagaggct ggagagcctg gcgagagagg   3540
cctgaaggga caccgtggct tcactggtct gcagggtctg ccggccctc ctggtccttc    3600
tggagaccaa ggtgcttctg gtcctgctgg tccttctggc cctagaggtc ctcctggccc   3660
```

```
cgtcagtccc tctggcaaag atggtgctaa tggaatccct ggccccattg ggcctcctgg    3720
tccccgtgga cgatcaggcg aaaccggtcc tgctggtcc cctggaaatc ctgggccccc    3780
tggtcctcca ggtcccctg gccctggcat cgacatgtcc gcctttgctg cttaggccc    3840 gagagagaag ggccccgacc ccctgcagta catgcgggcc gaccaggcag ccggtggcct    3900
gagacagcat gacgccgagg tggatgccac actcaagtcc ctcaacaacc agattgagag    3960
catccgcagc cccgagggct cccgcaagaa ccctgctcgc acctgcagag acctgaaact    4020
ctgccaccct gagtggaaga gtggagacta ctggattgac cccaaccaag gctgcacctt    4080
ggacgccatg aaggttttct gcaacatgga gactggcgag acttgcgtct accccaatcc    4140
agcaaacgtt cccaagaaga actggtggag cagcaagagc aaggagaaga aacacatctg    4200
gtttggagaa accatcaatg gtggcttcca tttcagctat ggagatgaca atctggctcc    4260
caacactgcc aacgtccaga tgaccttcct acgcctgctg tccacggaag gctcccagaa    4320
catcacctac cactgcaaga cagcattgc ctatctggac gaagcagctg gcaacctcaa    4380
gaaggccctg ctcatccagg gctccaatga cgtggagatc cgggcagagg gcaatagcag    4440
gttcacgtac actgccctga aggatggctg cacgaaacat accggtaagt ggggcaagac    4500
tgttatcgag taccggtcac agaagacctc acgcctcccc atcattgaca ttgcacccat    4560
ggacatagga gggcccgagc aggaattcgg tgtggacata gggccggtct gcttcttgta    4620
aaaacctgaa cccagaaaca acacaatccg ttgcaaaccc aaaggaccca agtactttcc    4680
aatctcagtc actctaggac tctgcactga atggctgacc tgacctgatg tccattcatc    4740
ccaccctctc acagttcgga ctttttctccc ctctcttctct aagagacctg aactgggcag    4800
actgcaaaat aaaatctcgg tgttctattt atttattgtc ttcctgtaag accttcgggt    4860
caaggcagag gcaggaaact aactggtgtg agtcaaatgc cccctgagtg actgcccca    4920 gcccaggcca aagaacctcc cttcaggtgc cgggcgcagg aactgtgtgt gtcctacaca    4980
atggtgctat tctgtgtcaa acacctctgt atttttttaaa acatcaattg atattaaaaa    5040
tgaaaagatt attggaaagt                                                5060
```

<210> SEQ ID NO 5
<211> LENGTH: 1487
<212> TYPE: PRT
<213> ORGANISM: Homo sapiens

<400> SEQUENCE: 5

```
Met Ile Arg Leu Gly Ala Pro Gln Ser Leu Val Leu Leu Thr Leu Leu
 1               5                  10                  15

Val Ala Ala Val Leu Arg Cys Gln Gly Gln Asp Val Gln Glu Ala Gly
                20                  25                  30

Ser Cys Val Gln Asp Gly Gln Arg Tyr Asn Asp Lys Asp Val Trp Lys
            35                  40                  45

Pro Glu Pro Cys Arg Ile Cys Val Cys Asp Thr Gly Thr Val Leu Cys
        50                  55                  60

Asp Asp Ile Ile Cys Glu Asp Val Lys Asp Cys Leu Ser Pro Glu Ile
 65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
           100                 105                 110

Lys Asp Ile Val Ser Pro Lys Gly Pro Pro Gly Pro Gln Gly Pro Ala
           115                 120                 125
```

-continued

```
Gly Glu Gln Gly Pro Arg Gly Asp Arg Gly Asp Lys Gly Glu Lys Gly
            130                 135                 140
Ala Pro Gly Pro Arg Gly Arg Asp Gly Glu Pro Gly Thr Pro Gly Asn
145                 150                 155                 160
Pro Gly Pro Pro Gly Pro Pro Gly Pro Pro Gly Pro Pro Gly Leu Gly
                165                 170                 175
Gly Asn Phe Ala Ala Gln Met Ala Gly Gly Phe Asp Glu Lys Ala Gly
            180                 185                 190
Gly Ala Gln Leu Gly Val Met Gln Gly Pro Met Gly Pro Met Gly Pro
                195                 200                 205
Arg Gly Pro Pro Gly Pro Ala Gly Ala Pro Gly Pro Gln Gly Phe Gln
        210                 215                 220
Gly Asn Pro Gly Glu Pro Gly Glu Pro Gly Val Ser Gly Pro Met Gly
225                 230                 235                 240
Pro Arg Gly Pro Pro Gly Pro Pro Gly Lys Pro Gly Asp Asp Gly Glu
                245                 250                 255
Ala Gly Lys Pro Gly Lys Ala Gly Glu Arg Gly Pro Pro Gly Pro Gln
            260                 265                 270
Gly Ala Arg Gly Phe Pro Gly Thr Pro Gly Leu Pro Gly Val Lys Gly
        275                 280                 285
His Arg Gly Tyr Pro Gly Leu Asp Gly Ala Lys Gly Glu Ala Gly Ala
    290                 295                 300
Pro Gly Val Lys Gly Glu Ser Gly Ser Pro Gly Glu Asn Gly Ser Pro
305                 310                 315                 320
Gly Pro Met Gly Pro Arg Gly Leu Pro Gly Glu Arg Gly Arg Thr Gly
                325                 330                 335
Pro Ala Gly Ala Ala Gly Ala Arg Gly Asn Asp Gly Gln Pro Gly Pro
            340                 345                 350
Ala Gly Pro Pro Gly Pro Val Gly Pro Ala Gly Pro Gly Phe Pro
        355                 360                 365
Gly Ala Pro Gly Ala Lys Gly Glu Ala Gly Pro Thr Gly Ala Arg Gly
    370                 375                 380
Pro Glu Gly Ala Gln Gly Pro Arg Gly Glu Pro Gly Thr Pro Gly Ser
385                 390                 395                 400
Pro Gly Pro Ala Gly Ala Ser Gly Asn Pro Gly Thr Asp Gly Ile Pro
                405                 410                 415
Gly Ala Lys Gly Ser Ala Gly Ala Pro Gly Ile Ala Gly Ala Pro Gly
            420                 425                 430
Phe Pro Gly Pro Arg Gly Pro Pro Gly Pro Gln Gly Ala Thr Gly Pro
        435                 440                 445
Leu Gly Pro Lys Gly Gln Thr Gly Glu Pro Gly Ile Ala Gly Phe Lys
    450                 455                 460
Gly Glu Gln Gly Pro Lys Gly Glu Pro Gly Pro Ala Gly Pro Gln Gly
465                 470                 475                 480
Ala Pro Gly Pro Ala Gly Glu Glu Gly Lys Arg Gly Ala Arg Gly Glu
                485                 490                 495
Pro Gly Gly Val Gly Pro Ile Gly Pro Pro Gly Glu Arg Gly Ala Pro
            500                 505                 510
Gly Asn Arg Gly Phe Pro Gly Gln Asp Gly Leu Ala Gly Pro Lys Gly
        515                 520                 525
Ala Pro Gly Glu Arg Gly Pro Ser Gly Leu Ala Gly Pro Lys Gly Ala
    530                 535                 540
```

-continued

```
Asn Gly Asp Pro Gly Arg Pro Gly Glu Pro Gly Leu Pro Gly Ala Arg
545                 550                 555                 560
Gly Leu Thr Gly Arg Pro Gly Asp Ala Gly Pro Gln Gly Lys Val Gly
            565                 570                 575
Pro Ser Gly Ala Pro Gly Glu Asp Gly Arg Pro Gly Pro Pro Gly Pro
                580                 585                 590
Gln Gly Ala Arg Gly Gln Pro Gly Val Met Gly Phe Pro Gly Pro Lys
            595                 600                 605
Gly Ala Asn Gly Glu Pro Gly Lys Ala Gly Glu Lys Gly Leu Pro Gly
        610                 615                 620
Ala Pro Gly Leu Arg Gly Leu Pro Gly Lys Asp Gly Glu Thr Gly Ala
625                 630                 635                 640
Ala Gly Pro Pro Gly Pro Ala Gly Pro Ala Gly Glu Arg Gly Glu Gln
            645                 650                 655
Gly Ala Pro Gly Pro Ser Gly Phe Gln Gly Leu Pro Gly Pro Pro Gly
                660                 665                 670
Pro Pro Gly Glu Gly Gly Lys Pro Gly Asp Gln Gly Val Pro Gly Glu
            675                 680                 685
Ala Gly Ala Pro Gly Leu Val Gly Pro Arg Gly Glu Arg Gly Phe Pro
        690                 695                 700
Gly Glu Arg Gly Ser Pro Gly Ala Gln Gly Leu Gln Gly Pro Arg Gly
705                 710                 715                 720
Leu Pro Gly Thr Pro Gly Thr Asp Gly Pro Lys Gly Ala Ser Gly Pro
            725                 730                 735
Ala Gly Pro Pro Gly Ala Gln Gly Pro Pro Gly Leu Gln Gly Met Pro
            740                 745                 750
Gly Glu Arg Gly Ala Ala Gly Ile Ala Gly Pro Lys Gly Asp Arg Gly
        755                 760                 765
Asp Val Gly Glu Lys Gly Pro Glu Gly Ala Pro Gly Lys Asp Gly Gly
    770                 775                 780
Arg Gly Leu Thr Gly Pro Ile Gly Pro Pro Gly Pro Ala Gly Ala Asn
785                 790                 795                 800
Gly Glu Lys Gly Glu Val Gly Pro Pro Gly Pro Ala Gly Ser Ala Gly
            805                 810                 815
Ala Arg Gly Ala Pro Gly Glu Arg Gly Glu Thr Gly Pro Pro Gly Pro
            820                 825                 830
Ala Gly Phe Ala Gly Pro Pro Gly Ala Asp Gly Gln Pro Gly Ala Lys
        835                 840                 845
Gly Glu Gln Gly Glu Ala Gly Gln Lys Gly Asp Ala Gly Ala Pro Gly
    850                 855                 860
Pro Gln Gly Pro Ser Gly Ala Pro Gly Pro Gln Gly Pro Thr Gly Val
865                 870                 875                 880
Thr Gly Pro Lys Gly Ala Arg Gly Ala Gln Gly Pro Pro Gly Ala Thr
            885                 890                 895
Gly Phe Pro Gly Ala Ala Gly Arg Val Gly Pro Pro Gly Ser Asn Gly
            900                 905                 910
Asn Pro Gly Pro Pro Gly Pro Pro Gly Pro Ser Gly Lys Asp Gly Pro
        915                 920                 925
Lys Gly Ala Arg Gly Asp Ser Gly Pro Pro Gly Arg Ala Gly Glu Pro
    930                 935                 940
Gly Leu Gln Gly Pro Ala Gly Pro Pro Gly Glu Lys Gly Glu Pro Gly
945                 950                 955                 960
Asp Asp Gly Pro Ser Gly Ala Glu Gly Pro Pro Gly Pro Gln Gly Leu
```

```
                    965                 970                 975
Ala Gly Gln Arg Gly Ile Val Gly Leu Pro Gly Gln Arg Gly Glu Arg
                980                 985                 990
Gly Phe Pro Gly Leu Pro Gly Pro Ser Gly Glu Pro Gly Lys Gln Gly
                995                 1000                1005
Ala Pro Gly Ala Ser Gly Asp Arg Gly Pro Pro Gly Pro Val Gly Pro
    1010                1015                1020
Pro Gly Leu Thr Gly Pro Ala Gly Glu Pro Gly Arg Glu Gly Ser Pro
1025                1030                1035                1040
Gly Ala Asp Gly Pro Pro Gly Arg Asp Gly Ala Ala Gly Val Lys Gly
            1045                1050                1055
Asp Arg Gly Glu Thr Gly Ala Val Gly Ala Pro Gly Ala Pro Gly Pro
        1060                1065                1070
Pro Gly Ser Pro Gly Pro Ala Gly Pro Thr Gly Lys Gln Gly Asp Arg
    1075                1080                1085
Gly Glu Ala Gly Ala Gln Gly Pro Met Gly Pro Ser Gly Pro Ala Gly
    1090                1095                1100
Ala Arg Gly Ile Gln Gly Pro Gln Gly Pro Arg Gly Asp Lys Gly Glu
1105                1110                1115                1120
Ala Gly Glu Pro Gly Glu Arg Gly Leu Lys Gly His Arg Gly Phe Thr
            1125                1130                1135
Gly Leu Gln Gly Leu Pro Gly Pro Pro Gly Pro Ser Gly Asp Gln Gly
        1140                1145                1150
Ala Ser Gly Pro Ala Gly Pro Ser Gly Pro Arg Gly Pro Pro Gly Pro
    1155                1160                1165
Val Ser Pro Ser Gly Lys Asp Gly Ala Asn Gly Ile Pro Gly Pro Ile
    1170                1175                1180
Gly Pro Pro Gly Pro Arg Gly Arg Ser Gly Glu Thr Gly Pro Ala Gly
1185                1190                1195                1200
Pro Pro Gly Asn Pro Gly Pro Pro Gly Pro Pro Gly Pro Pro Gly Pro
            1205                1210                1215
Gly Ile Asp Met Ser Ala Phe Ala Gly Leu Gly Pro Arg Glu Lys Gly
        1220                1225                1230
Pro Asp Pro Leu Gln Tyr Met Arg Ala Asp Gln Ala Ala Gly Gly Leu
    1235                1240                1245
Arg Gln His Asp Ala Glu Val Asp Ala Thr Leu Lys Ser Leu Asn Asn
    1250                1255                1260
Gln Ile Glu Ser Ile Arg Ser Pro Glu Gly Ser Arg Lys Asn Pro Ala
1265                1270                1275                1280
Arg Thr Cys Arg Asp Leu Lys Leu Cys His Pro Glu Trp Lys Ser Gly
            1285                1290                1295
Asp Tyr Trp Ile Asp Pro Asn Gln Gly Cys Thr Leu Asp Ala Met Lys
        1300                1305                1310
Val Phe Cys Asn Met Glu Thr Gly Glu Thr Cys Val Tyr Pro Asn Pro
    1315                1320                1325
Ala Asn Val Pro Lys Lys Asn Trp Trp Ser Ser Lys Ser Lys Glu Lys
    1330                1335                1340
Lys His Ile Trp Phe Gly Glu Thr Ile Asn Gly Gly Phe His Phe Ser
1345                1350                1355                1360
Tyr Gly Asp Asp Asn Leu Ala Pro Asn Thr Ala Asn Val Gln Met Thr
            1365                1370                1375
Phe Leu Arg Leu Leu Ser Thr Glu Gly Ser Gln Asn Ile Thr Tyr His
        1380                1385                1390
```

```
Cys Lys Asn Ser Ile Ala Tyr Leu Asp Glu Ala Ala Gly Asn Leu Lys
    1395                1400                1405

Lys Ala Leu Leu Ile Gln Gly Ser Asn Asp Val Glu Ile Arg Ala Glu
1410                1415                1420

Gly Asn Ser Arg Phe Thr Tyr Thr Ala Leu Lys Asp Gly Cys Thr Lys
1425                1430                1435                1440

His Thr Gly Lys Trp Gly Lys Thr Val Ile Glu Tyr Arg Ser Gln Lys
            1445                1450                1455

Thr Ser Arg Leu Pro Ile Ile Asp Ile Ala Pro Met Asp Ile Gly Gly
        1460                1465                1470

Pro Glu Gln Glu Phe Gly Val Asp Ile Gly Pro Val Cys Phe Leu
    1475                1480                1485

<210> SEQ ID NO 6
<211> LENGTH: 5060
<212> TYPE: DNA
<213> ORGANISM: Homo sapiens

<400> SEQUENCE: 6
```

| | | | | | |
|---|---|---|---|---|---|
| acgcagagcg | ctgctgggct | gccgggtctc | ccgcttcctc | ctcctgctcc | aagggcctcc | 60 |
| tgcatgaggg | cgcggtagag | acccggaccc | gcgccgtgct | cctgccgttt | cgctgcgctc | 120 |
| cgcccgggcc | cggctcagcc | aggccccgcg | gtgagccatg | attcgcctcg | ggctccccca | 180 |
| gtcgctggtg | ctgctgacgc | tgctcgtcgc | cgctgtcctt | cggtgtcagg | gccaggatgt | 240 |
| ccaggaggct | ggcagctgtg | tgcaggatgg | gcagaggtat | aatgataagg | atgtgtggaa | 300 |
| gccggagccc | tgccggatct | gtgtctgtga | cactgggact | gtcctctgcg | acgacataat | 360 |
| ctgtgaagac | gtgaaagact | gcctcagccc | tgagatcccc | ttcggagagt | gctgccccat | 420 |
| ctgcccaact | gacctcgcca | ctgccagtgg | gcaaccagga | ccaagggac | agaaaggaga | 480 |
| acctggagac | atcaaggata | ttgtaggacc | caaaggacct | cctgggcctc | agggacctgc | 540 |
| aggggaacaa | ggacccagag | gggatcgtgg | tgacaaaggt | gaaaaaggtg | ccctggacc | 600 |
| tcgtggcaga | gatggagaac | ctgggacccc | tggaaatcct | ggcccccctg | gtcctcccgg | 660 |
| cccccctggt | cccctggtc | ttggtggaaa | ctttgctgcc | cagatggctg | gaggatttga | 720 |
| tgaaaaggct | ggtggcgccc | agttgggagt | aatgcaagga | ccaatgggcc | catgggacc | 780 |
| tcgaggacct | ccaggccctg | caggtgctcc | tgggcctcaa | ggatttcaag | gcaatcctgg | 840 |
| tgaacctggt | gaacctggtg | tctctggtcc | catgggtccc | cgtggtcctc | ctggtccccc | 900 |
| tggaaagcct | ggtgatgatg | gtgaagctgg | aaaacctgga | aaagctggtg | aaagggtcc | 960 |
| gcctggtcct | cagggtgctc | gtggtttccc | aggaacccca | ggccttcctg | gtgtcaaagg | 1020 |
| tcacagaggt | tatccaggcc | tggacggtgc | taagggagag | gcgggtgctc | ctggtgtgaa | 1080 |
| gggtgagagt | ggttccccgg | gtgagaacgg | atctccgggc | ccaatgggtc | ctcgtggcct | 1140 |
| gcctggtgaa | agaggacgga | ctggccctgc | tggcgctgcg | ggtgcccgag | gcaacgatgg | 1200 |
| tcagccaggc | cccgcaggtc | ctccgggtcc | tgtcggtcct | gctggtggtc | ctggcttccc | 1260 |
| tggtgctcct | ggagccaagg | gtgaagccgg | ccccactggt | gccgtggtc | ctgaaggtgc | 1320 |
| tcaaggtcct | cgcggtgaac | ctggtactcc | tgggtcccct | gggcctgctg | gtgcctccgg | 1380 |
| taaccctgga | acagatggaa | ttcctggagc | caaaggatct | gctggtgctc | ctggcattgc | 1440 |
| tggtgctcct | ggcttccctg | ggccacgggg | tcctcctggc | cctcaaggtg | caactggtcc | 1500 |
| tctgggcccg | aaaggtcaga | cgggtgaacc | tggtattgct | ggcttcaaag | gtgaacaagg | 1560 |

```
ccccaaggga gaacctggcc ctgctggccc ccagggagcc cctggacccg ctggtgaaga    1620
aggcaagaga ggtgcccgtg gagagcctgg tggcgttggg cccatcggtc ccctggagag    1680
aagaggtgct cccggaaacc gcggtttccc aggtcaagat ggtctggcag gtcccaaggg    1740
agcccctgga gagcgagggc ccagtggtct tgctggcccc aagggagcca acggtgaccc    1800
tggccgtcct ggagaacctg gccttcctgg agcccggggt ctcactggcc gccctggtga    1860
tgctggtcct caaggcaaag ttggcccttc tggagcccct ggtgaagatg gtcgtcctgg    1920
acctccaggt cctcagggg ctcgtgggca gcctggtgtc atgggtttcc ctggccccaa     1980
aggtgccaac ggtgagcctg gcaaagctgg tgagaaggga ctgcctggtg ctcctggtct    2040
gaggggtctt cctggcaaag atggtgagac aggtgctgca ggaccccctg gccctgctgg    2100
acctgctggt gaacgaggcg agcagggtgc tcctgggcca tctgggttcc agggacttcc    2160
tggccctcct ggtccccag gtgaaggtgg aaaaccaggt gaccagggtg ttccggtga     2220
agctggagcc cctggcctcg tgggtccag gggtgaacga ggtttcccag gtgaacgtgg    2280
ctctcccggt gcccagggcc tccagagtcc ccgtggcctc cccggcactc ctggcactga    2340
tggtcccaaa ggtgcatctg gcccagcagg ccccctggc gcacagggcc tccaggtct      2400
tcagggaatg cctggcgaga ggggagcagc tggtatcgct gggcccaaag gcgacagggg    2460
tgacgttggt gagaaaggcc ctgagggagc cctggaaag gatggtggac gaggcctgac     2520
aggtcccatt ggcccccctg gccagctgg tgctaacggc gagaagggag aagttggacc     2580
tcctggtcct gcaggaagtg ctggtgctcg tggcgctccg ggtgaacgtg gagagactgg    2640
cccccccgga ccagcgggat tgctgggcc tcctggtgct gatggccagc tggggccaa      2700
gggtgagcaa ggagaggccg gccagaaagg cgatgctggt gcccctggtc tcagggccc    2760
ctctggagca cctgggcctc aggtcctac tggagtgact ggtcctaaag gagcccgagg     2820
tgcccaaggc ccccgggag ccactggatt ccctggagct gctggccgcg ttggaccccc    2880
aggctccaat ggcaaccctg gacccctgg tccccctggt ccttctggaa aagatggtcc     2940
caaaggtgct cgaggagaca gcggccccc tggccgagct ggtgaacccg gcctccaagg    3000
tcctgctgga ccccctggcg agaagggaga gcctggagat gacggtccct ctggtgccga    3060
aggtccacca ggtccccagg gtctggctgg tcagagagc atcgtcggtc tgcctgggca     3120
acgtggtgag agaggattcc ctggcttgcc tggcccatcg ggtgagcccg gcaagcaggg    3180
tgctcctgga gcatctggag acagaggtcc tcctggcccc gtgggtcctc ctggcctgac    3240
gggtcctgca ggtgaacccg gacgagaggg aagcccggt gctgatggcc ccctggcag     3300
agatggcgct gctggagtca agggtgatcg tggtgagact ggtgctgtgg gagctcctgg    3360
agccccctggg cccccctggct cccctggccc cgctggtcca actggcaagc aaggagacag   3420
aggagaagct ggtgcacaag gccccatggg accctcagga ccagctggag cccggggaat    3480
ccagggtcct caaggcccca gagtgacaa aggagaggg ggagagcctg gcgagagagg      3540
cctgaaggga caccgtggct tcactggtct gcagggtctg cccggccct ctggtccttc     3600
tggagaccaa ggtgcttctg gtcctgctgg tccttctggc cctagaggtc ctcctggccc    3660
cgtcggtccc tctggcaaag atggtgctaa tggaatccct ggccccattg gcctcctgg     3720
tccccgtgga cgatcaggcg aaaccggtcc tgctggtcct cctggaaatc ctgggccccc    3780
tggtcctcca ggtcccctg gccctggcat cgacatgtcc gcctttctg gcttaggccc     3840
gagagagaag ggccccgacc ccctgcagta catgcgggcc gaccaggcag ccggtggcct    3900
gagacagcat gacgccgagg tggatgccac actcaagtcc ctcaacaacc agattgagag    3960
```

-continued

| | |
|---|---|
| catccgcagc cccgagggct cccgcaagaa ccctgctcgc acctgcagag acctgaaact | 4020 |
| ctgccaccct gagtggaaga gtggagacta ctggattgac ccaaccaag gctgcacctt | 4080 |
| ggacgccatg aaggttttct gcaacatgga gactggcgag acttgcgtct accccaatcc | 4140 |
| agcaaacgtt cccaagaaga actggtggag cagcaagagc aaggagaaga acacatctg | 4200 |
| gtttggagaa accatcaatg gtggcttcca tttcagctat ggagatgaca atctggctcc | 4260 |
| caacactgcc aacgtccaga tgaccttcct acgcctgctg tccacggaag gctcccagaa | 4320 |
| catcacctac cactgcaaga acagcattgc ctatctggac gaagcagctg gcaacctcaa | 4380 |
| gaaggccctg ctcatccagg gctccaatga cgtggagatc cgggcagagg gcaatagcag | 4440 |
| gttcacgtac actgccctga aggatggctg cacgaaacat accggtaagt ggggcaagac | 4500 |
| tgttatcgag taccggtcac agaagacctc acgcctcccc atcattgaca ttgcacccat | 4560 |
| ggacatagga gggcccgagc aggaattcgg tgtggacata gggccggtct gcttcttgta | 4620 |
| aaaacctgaa cccagaaaca acacaatccg ttgcaaaccc aaaggaccca agtactttcc | 4680 |
| aatctcagtc actctaggac tctgcactga atggctgacc tgacctgatg tccattcatc | 4740 |
| ccaccctctc acagttcgga cttttctccc ctctctttct aagagacctg aactgggcag | 4800 |
| actgcaaaat aaaatctcgg tgttctattt atttattgtc ttcctgtaag accttcgggt | 4860 |
| caaggcagag gcaggaaact aactggtgtg agtcaaatgc cccctgagtg actgccccca | 4920 |
| gcccaggcca aagacctcc cttcaggtgc cgggcgcagg aactgtgtgt gtcctacaca | 4980 |
| atggtgctat tctgtgtcaa acacctctgt attttttaaa acatcaattg atattaaaaa | 5040 |
| tgaaaagatt attggaaagt | 5060 |

<210> SEQ ID NO 7
<211> LENGTH: 1487
<212> TYPE: PRT
<213> ORGANISM: Homo sapiens

<400> SEQUENCE: 7

Met Ile Arg Leu Gly Ala Pro Gln Ser Leu Val Leu Leu Thr Leu Leu
 1               5                   10                  15

Val Ala Ala Val Leu Arg Cys Gln Gly Gln Asp Val Gln Glu Ala Gly
                20                  25                  30

Ser Cys Val Gln Asp Gly Gln Arg Tyr Asn Asp Lys Asp Val Trp Lys
            35                  40                  45

Pro Glu Pro Cys Arg Ile Cys Val Cys Asp Thr Gly Thr Val Leu Cys
        50                  55                  60

Asp Asp Ile Ile Cys Glu Asp Val Lys Asp Cys Leu Ser Pro Glu Ile
65                  70                  75                  80

Pro Phe Gly Glu Cys Cys Pro Ile Cys Pro Thr Asp Leu Ala Thr Ala
                85                  90                  95

Ser Gly Gln Pro Gly Pro Lys Gly Gln Lys Gly Glu Pro Gly Asp Ile
            100                 105                 110

Lys Asp Ile Val Gly Pro Lys Gly Pro Pro Gly Pro Gln Gly Pro Ala
        115                 120                 125

Gly Glu Gln Gly Pro Arg Gly Asp Arg Gly Asp Lys Gly Glu Lys Gly
    130                 135                 140

Ala Pro Gly Pro Arg Gly Arg Asp Gly Glu Pro Gly Thr Pro Gly Asn
145                 150                 155                 160

Pro Gly Pro Pro Gly Pro Pro Gly Pro Pro Gly Pro Pro Gly Leu Gly
                165                 170                 175

```
Gly Asn Phe Ala Ala Gln Met Ala Gly Gly Phe Asp Glu Lys Ala Gly
            180                 185                 190
Gly Ala Gln Leu Gly Val Met Gln Gly Pro Met Gly Pro Met Gly Pro
        195                 200                 205
Arg Gly Pro Pro Gly Pro Ala Gly Ala Pro Gly Pro Gln Gly Phe Gln
    210                 215                 220
Gly Asn Pro Gly Glu Pro Gly Glu Pro Gly Val Ser Gly Pro Met Gly
225                 230                 235                 240
Pro Arg Gly Pro Pro Gly Pro Pro Gly Lys Pro Gly Asp Asp Gly Glu
                245                 250                 255
Ala Gly Lys Pro Gly Lys Ala Gly Glu Arg Gly Pro Pro Gly Pro Gln
            260                 265                 270
Gly Ala Arg Gly Phe Pro Gly Thr Pro Gly Leu Pro Gly Val Lys Gly
        275                 280                 285
His Arg Gly Tyr Pro Gly Leu Asp Gly Ala Lys Gly Glu Ala Gly Ala
    290                 295                 300
Pro Gly Val Lys Gly Glu Ser Gly Ser Pro Gly Glu Asn Gly Ser Pro
305                 310                 315                 320
Gly Pro Met Gly Pro Arg Gly Leu Pro Gly Glu Arg Gly Arg Thr Gly
                325                 330                 335
Pro Ala Gly Ala Ala Gly Ala Arg Gly Asn Asp Gly Gln Pro Gly Pro
            340                 345                 350
Ala Gly Pro Pro Gly Pro Val Gly Pro Ala Gly Gly Pro Gly Phe Pro
        355                 360                 365
Gly Ala Pro Gly Ala Lys Gly Glu Ala Gly Pro Thr Gly Ala Arg Gly
    370                 375                 380
Pro Glu Gly Ala Gln Gly Pro Arg Gly Glu Pro Gly Thr Pro Gly Ser
385                 390                 395                 400
Pro Gly Pro Ala Gly Ala Ser Gly Asn Pro Gly Thr Asp Gly Ile Pro
                405                 410                 415
Gly Ala Lys Gly Ser Ala Gly Ala Pro Gly Ile Ala Gly Ala Pro Gly
            420                 425                 430
Phe Pro Gly Pro Arg Gly Pro Pro Gly Pro Gln Gly Ala Thr Gly Pro
        435                 440                 445
Leu Gly Pro Lys Gly Gln Thr Gly Glu Pro Gly Ile Ala Gly Phe Lys
    450                 455                 460
Gly Glu Gln Gly Pro Lys Gly Glu Pro Gly Pro Ala Gly Pro Gln Gly
465                 470                 475                 480
Ala Pro Gly Pro Ala Gly Glu Glu Gly Lys Arg Gly Ala Arg Gly Glu
                485                 490                 495
Pro Gly Gly Val Gly Pro Ile Gly Pro Pro Gly Glu Arg Gly Ala Pro
            500                 505                 510
Gly Asn Arg Gly Phe Pro Gly Gln Asp Gly Leu Ala Gly Pro Lys Gly
        515                 520                 525
Ala Pro Gly Glu Arg Gly Pro Ser Gly Leu Ala Gly Pro Lys Gly Ala
    530                 535                 540
Asn Gly Asp Pro Gly Arg Pro Gly Glu Pro Gly Leu Pro Gly Ala Arg
545                 550                 555                 560
Gly Leu Thr Gly Arg Pro Gly Asp Ala Gly Pro Gln Gly Lys Val Gly
                565                 570                 575
Pro Ser Gly Ala Pro Gly Glu Asp Gly Arg Pro Gly Pro Pro Gly Pro
            580                 585                 590
```

-continued

```
Gln Gly Ala Arg Gly Gln Pro Gly Val Met Gly Phe Pro Gly Pro Lys
            595                 600                 605
Gly Ala Asn Gly Glu Pro Gly Lys Ala Gly Glu Lys Gly Leu Pro Gly
        610                 615                 620
Ala Pro Gly Leu Arg Gly Leu Pro Gly Lys Asp Gly Glu Thr Gly Ala
625                 630                 635                 640
Ala Gly Pro Pro Gly Pro Ala Gly Pro Ala Gly Glu Arg Gly Glu Gln
                645                 650                 655
Gly Ala Pro Gly Pro Ser Gly Phe Gln Gly Leu Pro Gly Pro Pro Gly
            660                 665                 670
Pro Pro Gly Glu Gly Gly Lys Pro Gly Asp Gln Gly Val Pro Gly Glu
        675                 680                 685
Ala Gly Ala Pro Gly Leu Val Gly Pro Arg Gly Glu Arg Gly Phe Pro
        690                 695                 700
Gly Glu Arg Gly Ser Pro Gly Ala Gln Gly Leu Gln Ser Pro Arg Gly
705                 710                 715                 720
Leu Pro Gly Thr Pro Gly Thr Asp Gly Pro Lys Gly Ala Ser Gly Pro
                725                 730                 735
Ala Gly Pro Pro Gly Ala Gln Gly Pro Pro Gly Leu Gln Gly Met Pro
            740                 745                 750
Gly Glu Arg Gly Ala Ala Gly Ile Ala Gly Pro Lys Gly Asp Arg Gly
        755                 760                 765
Asp Val Gly Glu Lys Gly Pro Glu Gly Ala Pro Gly Lys Asp Gly Gly
        770                 775                 780
Arg Gly Leu Thr Gly Pro Ile Gly Pro Pro Gly Pro Ala Gly Ala Asn
785                 790                 795                 800
Gly Glu Lys Gly Glu Val Gly Pro Pro Gly Pro Ala Gly Ser Ala Gly
                805                 810                 815
Ala Arg Gly Ala Pro Gly Glu Arg Gly Glu Thr Gly Pro Pro Gly Pro
            820                 825                 830
Ala Gly Phe Ala Gly Pro Pro Gly Ala Asp Gly Gln Pro Gly Ala Lys
        835                 840                 845
Gly Glu Gln Gly Glu Ala Gly Gln Lys Gly Asp Ala Gly Ala Pro Gly
        850                 855                 860
Pro Gln Gly Pro Ser Gly Ala Pro Gly Pro Gln Gly Pro Thr Gly Val
865                 870                 875                 880
Thr Gly Pro Lys Gly Ala Arg Gly Ala Gln Gly Pro Pro Gly Ala Thr
                885                 890                 895
Gly Phe Pro Gly Ala Ala Gly Arg Val Gly Pro Pro Gly Ser Asn Gly
            900                 905                 910
Asn Pro Gly Pro Pro Gly Pro Pro Gly Pro Ser Gly Lys Asp Gly Pro
        915                 920                 925
Lys Gly Ala Arg Gly Asp Ser Gly Pro Pro Gly Arg Ala Gly Glu Pro
        930                 935                 940
Gly Leu Gln Gly Pro Ala Gly Pro Pro Gly Glu Lys Gly Glu Pro Gly
945                 950                 955                 960
Asp Asp Gly Pro Ser Gly Ala Glu Gly Pro Pro Gly Pro Gln Gly Leu
                965                 970                 975
Ala Gly Gln Arg Gly Ile Val Gly Leu Pro Gly Gln Arg Gly Glu Arg
            980                 985                 990
Gly Phe Pro Gly Leu Pro Gly Pro Ser Gly Glu Pro Gly Lys Gln Gly
        995                 1000                1005
Ala Pro Gly Ala Ser Gly Asp Arg Gly Pro Pro Gly Pro Val Gly Pro
```

-continued

```
            1010                1015                1020
Pro Gly Leu Thr Gly Pro Ala Gly Glu Pro Gly Arg Glu Gly Ser Pro
1025                1030                1035                1040

Gly Ala Asp Gly Pro Pro Gly Arg Asp Gly Ala Ala Gly Val Lys Gly
                1045                1050                1055

Asp Arg Gly Glu Thr Gly Ala Val Gly Ala Pro Gly Ala Pro Gly Pro
                    1060                1065                1070

Pro Gly Ser Pro Gly Pro Ala Gly Pro Thr Gly Lys Gln Gly Asp Arg
                        1075                1080                1085

Gly Glu Ala Gly Ala Gln Gly Pro Met Gly Pro Ser Gly Pro Ala Gly
            1090                1095                1100

Ala Arg Gly Ile Gln Gly Pro Gln Gly Pro Arg Gly Asp Lys Gly Glu
1105                1110                1115                1120

Ala Gly Glu Pro Gly Glu Arg Gly Leu Lys Gly His Arg Gly Phe Thr
                1125                1130                1135

Gly Leu Gln Gly Leu Pro Gly Pro Pro Gly Pro Ser Gly Asp Gln Gly
                    1140                1145                1150

Ala Ser Gly Pro Ala Gly Pro Ser Gly Pro Arg Gly Pro Pro Gly Pro
                        1155                1160                1165

Val Gly Pro Ser Gly Lys Asp Gly Ala Asn Gly Ile Pro Gly Pro Ile
            1170                1175                1180

Gly Pro Pro Gly Pro Arg Gly Arg Ser Gly Glu Thr Gly Pro Ala Gly
1185                1190                1195                1200

Pro Pro Gly Asn Pro Gly Pro Pro Gly Pro Pro Gly Pro Pro Gly Pro
                1205                1210                1215

Gly Ile Asp Met Ser Ala Phe Ala Gly Leu Gly Pro Arg Glu Lys Gly
                    1220                1225                1230

Pro Asp Pro Leu Gln Tyr Met Arg Ala Asp Gln Ala Ala Gly Gly Leu
                        1235                1240                1245

Arg Gln His Asp Ala Glu Val Asp Ala Thr Leu Lys Ser Leu Asn Asn
             1250                1255                1260

Gln Ile Glu Ser Ile Arg Ser Pro Glu Gly Ser Arg Lys Asn Pro Ala
1265                1270                1275                1280

Arg Thr Cys Arg Asp Leu Lys Leu Cys His Pro Glu Trp Lys Ser Gly
                1285                1290                1295

Asp Tyr Trp Ile Asp Pro Asn Gln Gly Cys Thr Leu Asp Ala Met Lys
                    1300                1305                1310

Val Phe Cys Asn Met Glu Thr Gly Glu Thr Cys Val Tyr Pro Asn Pro
                        1315                1320                1325

Ala Asn Val Pro Lys Lys Asn Trp Trp Ser Ser Lys Ser Lys Glu Lys
             1330                1335                1340

Lys His Ile Trp Phe Gly Glu Thr Ile Asn Gly Gly Phe His Phe Ser
1345                1350                1355                1360

Tyr Gly Asp Asp Asn Leu Ala Pro Asn Thr Ala Asn Val Gln Met Thr
                1365                1370                1375

Phe Leu Arg Leu Leu Ser Thr Glu Gly Ser Gln Asn Ile Thr Tyr His
                    1380                1385                1390

Cys Lys Asn Ser Ile Ala Tyr Leu Asp Glu Ala Ala Gly Asn Leu Lys
                        1395                1400                1405

Lys Ala Leu Leu Ile Gln Gly Ser Asn Asp Val Glu Ile Arg Ala Glu
             1410                1415                1420

Gly Asn Ser Arg Phe Thr Tyr Thr Ala Leu Lys Asp Gly Cys Thr Lys
1425                1430                1435                1440
```

His Thr Gly Lys Trp Gly Lys Thr Val Ile Glu Tyr Arg Ser Gln Lys
                1445                1450                1455

Thr Ser Arg Leu Pro Ile Ile Asp Ile Ala Pro Met Asp Ile Gly Gly
            1460                1465                1470

Pro Glu Gln Glu Phe Gly Val Asp Ile Gly Pro Val Cys Phe Leu
        1475                1480                1485

<210> SEQ ID NO 8
<211> LENGTH: 25
<212> TYPE: PRT
<213> ORGANISM: Homo sapiens

<400> SEQUENCE: 8

Met Ile Arg Leu Gly Ala Pro Gln Ser Leu Val Leu Leu Thr Leu Leu
 1               5                  10                  15

Val Ala Ala Val Leu Arg Cys Gln Gly
            20                  25

<210> SEQ ID NO 9
<211> LENGTH: 56
<212> TYPE: PRT
<213> ORGANISM: Homo sapiens

<400> SEQUENCE: 9

Cys Val Gln Asp Gly Gln Arg Tyr Asn Asp Lys Asp Val Trp Lys Pro
 1               5                  10                  15

Glu Pro Cys Arg Ile Cys Val Cys Asp Thr Gly Thr Val Leu Cys Asp
            20                  25                  30

Asp Ile Ile Cys Glu Asp Val Lys Asp Cys Leu Ser Pro Glu Ile Pro
        35                  40                  45

Phe Gly Glu Cys Cys Pro Ile Cys
    50                  55

<210> SEQ ID NO 10
<211> LENGTH: 60
<212> TYPE: PRT
<213> ORGANISM: Homo sapiens

<400> SEQUENCE: 10

Gly Pro Lys Gly Pro Pro Gly Pro Gln Gly Pro Ala Gly Glu Gln Gly
 1               5                  10                  15

Pro Arg Gly Asp Arg Gly Asp Lys Gly Glu Lys Gly Ala Pro Gly Pro
            20                  25                  30

Arg Gly Arg Asp Gly Glu Pro Gly Thr Pro Gly Asn Pro Gly Pro Pro
        35                  40                  45

Gly Pro Pro Gly Pro Pro Gly Pro Pro Gly Leu Gly
    50                  55                  60

<210> SEQ ID NO 11
<211> LENGTH: 59
<212> TYPE: PRT
<213> ORGANISM: Homo sapiens

<400> SEQUENCE: 11

Met Gln Gly Pro Met Gly Pro Met Gly Pro Arg Gly Pro Pro Gly Pro
 1               5                  10                  15

Ala Gly Ala Pro Gly Pro Gln Gly Phe Gln Gly Asn Pro Gly Glu Pro
            20                  25                  30

Gly Glu Pro Gly Val Ser Gly Pro Met Gly Pro Arg Gly Pro Pro Gly

```
            35                  40                  45
Pro Pro Gly Lys Pro Gly Asp Asp Gly Glu Ala
    50                  55

<210> SEQ ID NO 12
<211> LENGTH: 60
<212> TYPE: PRT
<213> ORGANISM: Homo sapiens

<400> SEQUENCE: 12

Gly Lys Pro Gly Lys Ala Gly Glu Arg Gly Pro Pro Gly Pro Gln Gly
1               5                  10                  15

Ala Arg Gly Phe Pro Gly Thr Pro Gly Leu Pro Gly Val Lys Gly His
                20                  25                  30

Arg Gly Tyr Pro Gly Leu Asp Gly Ala Lys Gly Glu Ala Gly Ala Pro
            35                  40                  45

Gly Val Lys Gly Glu Ser Gly Ser Pro Gly Glu Asn
    50                  55                  60

<210> SEQ ID NO 13
<211> LENGTH: 60
<212> TYPE: PRT
<213> ORGANISM: Homo sapiens

<400> SEQUENCE: 13

Gly Ser Pro Gly Pro Met Gly Pro Arg Gly Leu Pro Gly Glu Arg Gly
1               5                  10                  15

Arg Thr Gly Pro Ala Gly Ala Ala Gly Ala Arg Gly Asn Asp Gly Gln
                20                  25                  30

Pro Gly Pro Ala Gly Pro Pro Gly Pro Val Gly Pro Ala Gly Gly Pro
            35                  40                  45

Gly Phe Pro Gly Ala Pro Gly Ala Lys Gly Glu Ala
    50                  55                  60

<210> SEQ ID NO 14
<211> LENGTH: 60
<212> TYPE: PRT
<213> ORGANISM: Homo sapiens

<400> SEQUENCE: 14

Gly Pro Thr Gly Ala Arg Gly Pro Glu Gly Ala Gln Gly Pro Arg Gly
1               5                  10                  15

Glu Pro Gly Thr Pro Gly Ser Pro Gly Pro Ala Gly Ala Ser Gly Asn
                20                  25                  30

Pro Gly Thr Asp Gly Ile Pro Gly Ala Lys Gly Ser Ala Gly Ala Pro
            35                  40                  45

Gly Ile Ala Gly Ala Pro Gly Phe Pro Gly Pro Arg
    50                  55                  60

<210> SEQ ID NO 15
<211> LENGTH: 60
<212> TYPE: PRT
<213> ORGANISM: Homo sapiens

<400> SEQUENCE: 15

Gly Pro Pro Gly Pro Gln Gly Ala Thr Gly Pro Leu Gly Pro Lys Gly
1               5                  10                  15

Gln Thr Gly Glu Pro Gly Ile Ala Gly Phe Lys Gly Glu Gln Gly Pro
                20                  25                  30
```

```
Lys Gly Glu Pro Gly Pro Ala Gly Pro Gln Gly Ala Pro Gly Pro Ala
             35                  40                  45

Gly Glu Glu Gly Lys Arg Gly Ala Arg Gly Glu Pro
         50                  55                  60

<210> SEQ ID NO 16
<211> LENGTH: 60
<212> TYPE: PRT
<213> ORGANISM: Homo sapiens

<400> SEQUENCE: 16

Gly Gly Val Gly Pro Ile Gly Pro Pro Gly Glu Arg Gly Ala Pro Gly
  1               5                  10                  15

Asn Arg Gly Phe Pro Gly Gln Asp Gly Leu Ala Gly Pro Lys Gly Ala
             20                  25                  30

Pro Gly Glu Arg Gly Pro Ser Gly Leu Ala Gly Pro Lys Gly Ala Asn
         35                  40                  45

Gly Asp Pro Gly Arg Pro Gly Glu Pro Gly Leu Pro
         50                  55                  60

<210> SEQ ID NO 17
<211> LENGTH: 60
<212> TYPE: PRT
<213> ORGANISM: Homo sapiens

<400> SEQUENCE: 17

Gly Ala Arg Gly Leu Thr Gly Arg Pro Gly Asp Ala Gly Pro Gln Gly
  1               5                  10                  15

Lys Val Gly Pro Ser Gly Ala Pro Gly Glu Asp Gly Arg Pro Gly Pro
             20                  25                  30

Pro Gly Pro Gln Gly Ala Arg Gly Gln Pro Gly Val Met Gly Phe Pro
         35                  40                  45

Gly Pro Lys Gly Ala Asn Gly Glu Pro Gly Lys Ala
         50                  55                  60

<210> SEQ ID NO 18
<211> LENGTH: 60
<212> TYPE: PRT
<213> ORGANISM: Homo sapiens

<400> SEQUENCE: 18

Gly Glu Lys Gly Leu Pro Gly Ala Pro Gly Leu Arg Gly Leu Pro Gly
  1               5                  10                  15

Lys Asp Gly Glu Thr Gly Ala Ala Gly Pro Pro Gly Pro Ala Gly Pro
             20                  25                  30

Ala Gly Glu Arg Gly Glu Gln Gly Ala Pro Gly Pro Ser Gly Phe Gln
         35                  40                  45

Gly Leu Pro Gly Pro Pro Gly Pro Pro Gly Glu Gly
         50                  55                  60

<210> SEQ ID NO 19
<211> LENGTH: 60
<212> TYPE: PRT
<213> ORGANISM: Homo sapiens

<400> SEQUENCE: 19

Gly Lys Pro Gly Asp Gln Gly Val Pro Gly Glu Ala Gly Ala Pro Gly
  1               5                  10                  15

Leu Val Gly Pro Arg Gly Glu Arg Gly Phe Pro Gly Glu Arg Gly Ser
             20                  25                  30
```

Pro Gly Ala Gln Gly Leu Gln Gly Pro Arg Gly Leu Pro Gly Thr Pro
        35                  40                  45

Gly Thr Asp Gly Pro Lys Gly Ala Ser Gly Pro Ala
        50                  55                  60

<210> SEQ ID NO 20
<211> LENGTH: 60
<212> TYPE: PRT
<213> ORGANISM: Homo sapiens

<400> SEQUENCE: 20

Gly Pro Pro Gly Ala Gln Gly Pro Pro Gly Leu Gln Gly Met Pro Gly
1               5                   10                  15

Glu Arg Gly Ala Ala Gly Ile Ala Gly Pro Lys Gly Asp Arg Gly Asp
            20                  25                  30

Val Gly Glu Lys Gly Pro Glu Gly Ala Pro Gly Lys Asp Gly Gly Arg
        35                  40                  45

Gly Leu Thr Gly Pro Ile Gly Pro Pro Gly Pro Ala
    50                  55                  60

<210> SEQ ID NO 21
<211> LENGTH: 60
<212> TYPE: PRT
<213> ORGANISM: Homo sapiens

<400> SEQUENCE: 21

Gly Glu Lys Gly Glu Val Gly Pro Pro Gly Pro Ala Gly Ser Ala Gly
1               5                   10                  15

Ala Arg Gly Ala Pro Gly Glu Arg Gly Glu Thr Gly Pro Pro Gly Pro
            20                  25                  30

Ala Gly Phe Ala Gly Pro Pro Gly Ala Asp Gly Gln Pro Gly Ala Lys
        35                  40                  45

Gly Glu Gln Gly Glu Ala Gly Gln Lys Gly Asp Ala
    50                  55                  60

<210> SEQ ID NO 22
<211> LENGTH: 60
<212> TYPE: PRT
<213> ORGANISM: Homo sapiens

<400> SEQUENCE: 22

Gly Ala Pro Gly Pro Gln Gly Pro Ser Gly Ala Pro Gly Pro Gln Gly
1               5                   10                  15

Pro Thr Gly Val Thr Gly Pro Lys Gly Ala Arg Gly Ala Gln Gly Pro
            20                  25                  30

Pro Gly Ala Thr Gly Phe Pro Gly Ala Ala Gly Arg Val Gly Pro Pro
        35                  40                  45

Gly Ser Asn Gly Asn Pro Gly Pro Pro Gly Pro Pro
    50                  55                  60

<210> SEQ ID NO 23
<211> LENGTH: 60
<212> TYPE: PRT
<213> ORGANISM: Homo sapiens

<400> SEQUENCE: 23

Gly Pro Ser Gly Lys Asp Gly Pro Lys Gly Ala Arg Gly Asp Ser Gly
1               5                   10                  15

Pro Pro Gly Arg Ala Gly Glu Pro Gly Leu Gln Gly Pro Ala Gly Pro

```
                    20                  25                  30
Pro Gly Glu Lys Gly Glu Pro Gly Asp Gly Pro Ser Gly Ala Glu
        35                  40                  45

Gly Pro Pro Gly Pro Gln Gly Leu Ala Gly Gln Arg
    50                  55                  60

<210> SEQ ID NO 24
<211> LENGTH: 60
<212> TYPE: PRT
<213> ORGANISM: Homo sapiens

<400> SEQUENCE: 24

Gly Ile Val Gly Leu Pro Gly Gln Arg Gly Glu Arg Gly Phe Pro Gly
1               5                  10                  15

Leu Pro Gly Pro Ser Gly Glu Pro Gly Lys Gln Gly Ala Pro Gly Ala
            20                  25                  30

Ser Gly Asp Arg Gly Pro Pro Gly Pro Val Gly Pro Pro Gly Leu Thr
        35                  40                  45

Gly Pro Ala Gly Glu Pro Gly Arg Glu Gly Ser Pro
    50                  55                  60

<210> SEQ ID NO 25
<211> LENGTH: 60
<212> TYPE: PRT
<213> ORGANISM: Homo sapiens

<400> SEQUENCE: 25

Gly Ala Asp Gly Pro Pro Gly Arg Asp Gly Ala Ala Gly Val Lys Gly
1               5                  10                  15

Asp Arg Gly Glu Thr Gly Ala Val Gly Ala Pro Gly Ala Pro Gly Pro
            20                  25                  30

Pro Gly Ser Pro Gly Pro Ala Gly Pro Thr Gly Lys Gln Gly Asp Arg
        35                  40                  45

Gly Glu Ala Gly Ala Gln Gly Pro Met Gly Pro Ser
    50                  55                  60

<210> SEQ ID NO 26
<211> LENGTH: 60
<212> TYPE: PRT
<213> ORGANISM: Homo sapiens

<400> SEQUENCE: 26

Gly Pro Ala Gly Ala Arg Gly Ile Gln Gly Pro Gln Gly Pro Arg Gly
1               5                  10                  15

Asp Lys Gly Glu Ala Gly Glu Pro Gly Glu Arg Gly Leu Lys Gly His
            20                  25                  30

Arg Gly Phe Thr Gly Leu Gln Gly Leu Pro Gly Pro Pro Gly Pro Ser
        35                  40                  45

Gly Asp Gln Gly Ala Ser Gly Pro Ala Gly Pro Ser
    50                  55                  60

<210> SEQ ID NO 27
<211> LENGTH: 60
<212> TYPE: PRT
<213> ORGANISM: Homo sapiens

<400> SEQUENCE: 27

Gly Pro Arg Gly Pro Pro Gly Pro Val Gly Pro Ser Gly Lys Asp Gly
1               5                  10                  15
```

```
Ala Asn Gly Ile Pro Gly Pro Ile Gly Pro Pro Gly Pro Arg Gly Arg
         20                  25                  30

Ser Gly Glu Thr Gly Pro Ala Gly Pro Pro Gly Asn Pro Gly Pro Pro
         35                  40                  45

Gly Pro Pro Gly Pro Pro Gly Pro Gly Ile Asp Met
         50                  55                  60

<210> SEQ ID NO 28
<211> LENGTH: 218
<212> TYPE: PRT
<213> ORGANISM: Homo sapiens

<400> SEQUENCE: 28

Ile Arg Ser Pro Glu Gly Ser Arg Lys Asn Pro Ala Arg Thr Cys Arg
  1               5                  10                  15

Asp Leu Lys Leu Cys His Pro Glu Trp Lys Ser Gly Asp Tyr Trp Ile
             20                  25                  30

Asp Pro Asn Gln Gly Cys Thr Leu Asp Ala Met Lys Val Phe Cys Asn
         35                  40                  45

Met Glu Thr Gly Glu Thr Cys Val Tyr Pro Asn Pro Ala Asn Val Pro
     50                  55                  60

Lys Lys Asn Trp Trp Ser Ser Lys Ser Lys Glu Lys His Ile Trp
 65                  70                  75                  80

Phe Gly Glu Thr Ile Asn Gly Gly Phe His Phe Ser Tyr Gly Asp Asp
                 85                  90                  95

Asn Leu Ala Pro Asn Thr Ala Asn Val Gln Met Thr Phe Leu Arg Leu
            100                 105                 110

Leu Ser Thr Glu Gly Ser Gln Asn Ile Thr Tyr His Cys Lys Asn Ser
        115                 120                 125

Ile Ala Tyr Leu Asp Glu Ala Ala Gly Asn Leu Lys Lys Ala Leu Leu
    130                 135                 140

Ile Gln Gly Ser Asn Asp Val Glu Ile Arg Ala Glu Gly Asn Ser Arg
145                 150                 155                 160

Phe Thr Tyr Thr Ala Leu Lys Asp Gly Cys Thr Lys His Thr Gly Lys
                165                 170                 175

Trp Gly Lys Thr Val Ile Glu Tyr Arg Ser Gln Lys Thr Ser Arg Leu
            180                 185                 190

Pro Ile Ile Asp Ile Ala Pro Met Asp Ile Gly Gly Pro Glu Gln Glu
        195                 200                 205

Phe Gly Val Asp Ile Gly Pro Val Cys Phe
    210                 215

<210> SEQ ID NO 29
<211> LENGTH: 99
<212> TYPE: DNA
<213> ORGANISM: Homo sapiens

<400> SEQUENCE: 29
ggtgaacgag gtttcccagg tgaacgtggc tctcccggtg cccagggcct ccagggtccc    60
cgtggcctcc ccggcactcc tggcactgat ggtcccaaa                           99

<210> SEQ ID NO 30
<211> LENGTH: 30
<212> TYPE: PRT
<213> ORGANISM: Homo sapiens

<400> SEQUENCE: 30
```

-continued

Gly Glu Arg Gly Phe Pro Gly Glu Arg Gly Ser Pro Gly Ala Gln Gly
1               5                   10                  15

Leu Gln Gly Pro Arg Gly Leu Pro Gly Thr Pro Gly Thr Asp
            20                  25                  30

<210> SEQ ID NO 31
<211> LENGTH: 108
<212> TYPE: DNA
<213> ORGANISM: Homo sapiens

<400> SEQUENCE: 31
ggtcctcctg gccccgtcgg tccctctggc aaagatggtg ctaatggaat ccctggcccc    60
attgggcctc ctggtccccg tggacgatca ggcgaaaccg gtcctgct                108

<210> SEQ ID NO 32
<211> LENGTH: 30
<212> TYPE: PRT
<213> ORGANISM: Homo sapiens

<400> SEQUENCE: 32

Gly Pro Pro Gly Pro Val Gly Pro Ser Gly Lys Asp Gly Ala Asn Gly
1               5                   10                  15

Ile Pro Gly Pro Ile Gly Pro Pro Gly Pro Arg Gly Arg Ser
            20                  25                  30

<210> SEQ ID NO 33
<211> LENGTH: 19
<212> TYPE: DNA
<213> ORGANISM: Homo sapiens

<400> SEQUENCE: 33
gcgtcaggcg tttgggagt                                                 19

<210> SEQ ID NO 34
<211> LENGTH: 18
<212> TYPE: DNA
<213> ORGANISM: Homo sapiens

<400> SEQUENCE: 34
ggggccgact gggaaatt                                                  18

<210> SEQ ID NO 35
<211> LENGTH: 19
<212> TYPE: DNA
<213> ORGANISM: Homo sapiens

<400> SEQUENCE: 35
ccgctgggct gtaacctga                                                 19

<210> SEQ ID NO 36
<211> LENGTH: 20
<212> TYPE: DNA
<213> ORGANISM: Homo sapiens

<400> SEQUENCE: 36
accaggtact gcagggaagg                                                20

<210> SEQ ID NO 37
<211> LENGTH: 20
<212> TYPE: DNA
<213> ORGANISM: Homo sapiens

<400> SEQUENCE: 37

```
accctgggac agagtccttg                                              20

<210> SEQ ID NO 38
<211> LENGTH: 19
<212> TYPE: DNA
<213> ORGANISM: Homo sapiens

<400> SEQUENCE: 38
ttcaggttac agcccagcg                                               19

<210> SEQ ID NO 39
<211> LENGTH: 20
<212> TYPE: DNA
<213> ORGANISM: Homo sapiens

<400> SEQUENCE: 39
aactagcccc tctgctttgc                                              20

<210> SEQ ID NO 40
<211> LENGTH: 20
<212> TYPE: DNA
<213> ORGANISM: Homo sapiens

<400> SEQUENCE: 40
caacatggtg caaggtgcat                                              20

<210> SEQ ID NO 41
<211> LENGTH: 20
<212> TYPE: DNA
<213> ORGANISM: Homo sapiens

<400> SEQUENCE: 41
aagatgacag caaggccagg                                              20

<210> SEQ ID NO 42
<211> LENGTH: 20
<212> TYPE: DNA
<213> ORGANISM: Homo sapiens

<400> SEQUENCE: 42
cgccttcctt gattgtgtcc                                              20

<210> SEQ ID NO 43
<211> LENGTH: 19
<212> TYPE: DNA
<213> ORGANISM: Homo sapiens

<400> SEQUENCE: 43
acaggcctga gggcaaagc                                               19

<210> SEQ ID NO 44
<211> LENGTH: 20
<212> TYPE: DNA
<213> ORGANISM: Homo sapiens

<400> SEQUENCE: 44
cgcgcaagtt actgatctgc                                              20

<210> SEQ ID NO 45
<211> LENGTH: 18
<212> TYPE: DNA
<213> ORGANISM: Homo sapiens
```

-continued

```
<400> SEQUENCE: 45
atctccccat cttcattc                                                     18

<210> SEQ ID NO 46
<211> LENGTH: 18
<212> TYPE: DNA
<213> ORGANISM: Homo sapiens

<400> SEQUENCE: 46
ttgccactgt catctaat                                                     18

<210> SEQ ID NO 47
<211> LENGTH: 18
<212> TYPE: DNA
<213> ORGANISM: Homo sapiens

<400> SEQUENCE: 47
tggtccttgc cacattgg                                                     18

<210> SEQ ID NO 48
<211> LENGTH: 20
<212> TYPE: DNA
<213> ORGANISM: Homo sapiens

<400> SEQUENCE: 48
ccccttgccc acagagtaac                                                   20

<210> SEQ ID NO 49
<211> LENGTH: 20
<212> TYPE: DNA
<213> ORGANISM: Homo sapiens

<400> SEQUENCE: 49
ttctcaattt cccttcctgg                                                   20

<210> SEQ ID NO 50
<211> LENGTH: 20
<212> TYPE: DNA
<213> ORGANISM: Homo sapiens

<400> SEQUENCE: 50
tgtcctaaca gccccctttc                                                   20

<210> SEQ ID NO 51
<211> LENGTH: 19
<212> TYPE: DNA
<213> ORGANISM: Homo sapiens

<400> SEQUENCE: 51
ttcctgggaa accacgagc                                                    19

<210> SEQ ID NO 52
<211> LENGTH: 18
<212> TYPE: DNA
<213> ORGANISM: Homo sapiens

<400> SEQUENCE: 52
aaaggcatgg agggctgg                                                     18

<210> SEQ ID NO 53
<211> LENGTH: 20
<212> TYPE: DNA
<213> ORGANISM: Homo sapiens
```

-continued

<400> SEQUENCE: 53
gcacaaggtc agtgtctggg    20

<210> SEQ ID NO 54
<211> LENGTH: 20
<212> TYPE: DNA
<213> ORGANISM: Homo sapiens

<400> SEQUENCE: 54
cagggcagct ttccactgtt    20

<210> SEQ ID NO 55
<211> LENGTH: 20
<212> TYPE: DNA
<213> ORGANISM: Homo sapiens

<400> SEQUENCE: 55
aatcatgctt tcacccatcg    20

<210> SEQ ID NO 56
<211> LENGTH: 20
<212> TYPE: DNA
<213> ORGANISM: Homo sapiens

<400> SEQUENCE: 56
actgcaagga gcaaggtgtg    20

<210> SEQ ID NO 57
<211> LENGTH: 20
<212> TYPE: DNA
<213> ORGANISM: Homo sapiens

<400> SEQUENCE: 57
gactgctgaa aggatggctg    20

<210> SEQ ID NO 58
<211> LENGTH: 20
<212> TYPE: DNA
<213> ORGANISM: Homo sapiens

<400> SEQUENCE: 58
cgacagagcc agactccgtc    20

<210> SEQ ID NO 59
<211> LENGTH: 19
<212> TYPE: DNA
<213> ORGANISM: Homo sapiens

<400> SEQUENCE: 59
cctgccaggc ctatggtgt    19

<210> SEQ ID NO 60
<211> LENGTH: 20
<212> TYPE: DNA
<213> ORGANISM: Homo sapiens

<400> SEQUENCE: 60
ccttctgaag ccaggcaaag    20

<210> SEQ ID NO 61
<211> LENGTH: 19
<212> TYPE: DNA

<210> SEQ ID NO 61
<211> LENGTH: 19
<212> TYPE: DNA
<213> ORGANISM: Homo sapiens

<400> SEQUENCE: 61
gatcctttgg ctccaggaa                                            19

<210> SEQ ID NO 62
<211> LENGTH: 18
<212> TYPE: DNA
<213> ORGANISM: Homo sapiens

<400> SEQUENCE: 62
agggttgggt gcatgtgc                                             18

<210> SEQ ID NO 63
<211> LENGTH: 20
<212> TYPE: DNA
<213> ORGANISM: Homo sapiens

<400> SEQUENCE: 63
ggcctgtgcc tcatagaaca                                           20

<210> SEQ ID NO 64
<211> LENGTH: 20
<212> TYPE: DNA
<213> ORGANISM: Homo sapiens

<400> SEQUENCE: 64
ggggttcatt ctttgctgct                                           20

<210> SEQ ID NO 65
<211> LENGTH: 20
<212> TYPE: DNA
<213> ORGANISM: Homo sapiens

<400> SEQUENCE: 65
ccacaaggac tccacttccc                                           20

<210> SEQ ID NO 66
<211> LENGTH: 20
<212> TYPE: DNA
<213> ORGANISM: Homo sapiens

<400> SEQUENCE: 66
cccaagggag aacctgtgag                                           20

<210> SEQ ID NO 67
<211> LENGTH: 20
<212> TYPE: DNA
<213> ORGANISM: Homo sapiens

<400> SEQUENCE: 67
acttcaggcc tccctaaccc                                           20

<210> SEQ ID NO 68
<211> LENGTH: 20
<212> TYPE: DNA
<213> ORGANISM: Homo sapiens

<400> SEQUENCE: 68
gtgggttagt gggatggacc                                           20

<210> SEQ ID NO 69
<211> LENGTH: 19

```
<212> TYPE: DNA
<213> ORGANISM: Homo sapiens

<400> SEQUENCE: 69
ctgggcactg ccacatgga                                              19

<210> SEQ ID NO 70
<211> LENGTH: 20
<212> TYPE: DNA
<213> ORGANISM: Homo sapiens

<400> SEQUENCE: 70
gggggaatga tgacatcgtg                                             20

<210> SEQ ID NO 71
<211> LENGTH: 20
<212> TYPE: DNA
<213> ORGANISM: Homo sapiens

<400> SEQUENCE: 71
gctgttctca gcatggaagc                                             20

<210> SEQ ID NO 72
<211> LENGTH: 20
<212> TYPE: DNA
<213> ORGANISM: Homo sapiens

<400> SEQUENCE: 72
gcagtggggg tctgtatgtg                                             20

<210> SEQ ID NO 73
<211> LENGTH: 20
<212> TYPE: DNA
<213> ORGANISM: Homo sapiens

<400> SEQUENCE: 73
gtccaggaca ttcccaggcc                                             20

<210> SEQ ID NO 74
<211> LENGTH: 20
<212> TYPE: DNA
<213> ORGANISM: Homo sapiens

<400> SEQUENCE: 74
aagacgcctg tgctgcccac                                             20

<210> SEQ ID NO 75
<211> LENGTH: 20
<212> TYPE: DNA
<213> ORGANISM: Homo sapiens

<400> SEQUENCE: 75
cctgagcccg ctcctcttct                                             20

<210> SEQ ID NO 76
<211> LENGTH: 20
<212> TYPE: DNA
<213> ORGANISM: Homo sapiens

<400> SEQUENCE: 76
ggctctttgg acctgcaacc                                             20

<210> SEQ ID NO 77
```

```
<211> LENGTH: 20
<212> TYPE: DNA
<213> ORGANISM: Homo sapiens

<400> SEQUENCE: 77
gctgtggtct cagggtgggt                                                   20

<210> SEQ ID NO 78
<211> LENGTH: 19
<212> TYPE: DNA
<213> ORGANISM: Homo sapiens

<400> SEQUENCE: 78
tgggagtccc actgagcag                                                    19

<210> SEQ ID NO 79
<211> LENGTH: 20
<212> TYPE: DNA
<213> ORGANISM: Homo sapiens

<400> SEQUENCE: 79
ccttggccga gggtgacagt                                                   20

<210> SEQ ID NO 80
<211> LENGTH: 19
<212> TYPE: DNA
<213> ORGANISM: Homo sapiens

<400> SEQUENCE: 80
tgggcaggga ctgggcttt                                                    19

<210> SEQ ID NO 81
<211> LENGTH: 20
<212> TYPE: DNA
<213> ORGANISM: Homo sapiens

<400> SEQUENCE: 81
agagacgggg atctgaaagc                                                   20

<210> SEQ ID NO 82
<211> LENGTH: 20
<212> TYPE: DNA
<213> ORGANISM: Homo sapiens

<400> SEQUENCE: 82
gcagtgttcc ctgttgggtg                                                   20

<210> SEQ ID NO 83
<211> LENGTH: 20
<212> TYPE: DNA
<213> ORGANISM: Homo sapiens

<400> SEQUENCE: 83
caggcctgcg aaccatcctc                                                   20

<210> SEQ ID NO 84
<211> LENGTH: 20
<212> TYPE: DNA
<213> ORGANISM: Homo sapiens

<400> SEQUENCE: 84
agaagcaggt caggcagcgg                                                   20
```

```
<210> SEQ ID NO 85
<211> LENGTH: 19
<212> TYPE: DNA
<213> ORGANISM: Homo sapiens

<400> SEQUENCE: 85
ccccgggtct ggtcataga                                             19

<210> SEQ ID NO 86
<211> LENGTH: 20
<212> TYPE: DNA
<213> ORGANISM: Homo sapiens

<400> SEQUENCE: 86
caagtctcct gtggcagagg                                            20

<210> SEQ ID NO 87
<211> LENGTH: 19
<212> TYPE: DNA
<213> ORGANISM: Homo sapiens

<400> SEQUENCE: 87
tgtcctgccc accaagcca                                             19

<210> SEQ ID NO 88
<211> LENGTH: 19
<212> TYPE: DNA
<213> ORGANISM: Homo sapiens

<400> SEQUENCE: 88
attccccagc ccgaggctt                                             19

<210> SEQ ID NO 89
<211> LENGTH: 18
<212> TYPE: DNA
<213> ORGANISM: Homo sapiens

<400> SEQUENCE: 89
ccaggcaagc cagggaat                                              18

<210> SEQ ID NO 90
<211> LENGTH: 20
<212> TYPE: DNA
<213> ORGANISM: Homo sapiens

<400> SEQUENCE: 90
ccccagagag gaaactgctg                                            20

<210> SEQ ID NO 91
<211> LENGTH: 20
<212> TYPE: DNA
<213> ORGANISM: Homo sapiens

<400> SEQUENCE: 91
tctatgcccg tctctctccc                                            20

<210> SEQ ID NO 92
<211> LENGTH: 20
<212> TYPE: DNA
<213> ORGANISM: Homo sapiens

<400> SEQUENCE: 92
tgggccactg tcagttctca                                            20
```

```
<210> SEQ ID NO 93
<211> LENGTH: 18
<212> TYPE: DNA
<213> ORGANISM: Homo sapiens

<400> SEQUENCE: 93
tgagcgcagc gtcagaga                                              18

<210> SEQ ID NO 94
<211> LENGTH: 20
<212> TYPE: DNA
<213> ORGANISM: Homo sapiens

<400> SEQUENCE: 94
gttgggcaga agaggagagg                                            20

<210> SEQ ID NO 95
<211> LENGTH: 20
<212> TYPE: DNA
<213> ORGANISM: Homo sapiens

<400> SEQUENCE: 95
ctccagccct gaggaaatcc                                            20

<210> SEQ ID NO 96
<211> LENGTH: 19
<212> TYPE: DNA
<213> ORGANISM: Homo sapiens

<400> SEQUENCE: 96
gggtttccgc agtctctgg                                             19

<210> SEQ ID NO 97
<211> LENGTH: 20
<212> TYPE: DNA
<213> ORGANISM: Homo sapiens

<400> SEQUENCE: 97
tttggccaag aaccagcagg                                            20

<210> SEQ ID NO 98
<211> LENGTH: 20
<212> TYPE: DNA
<213> ORGANISM: Homo sapiens

<400> SEQUENCE: 98
actgcctgcg tgggacttcc                                            20

<210> SEQ ID NO 99
<211> LENGTH: 20
<212> TYPE: DNA
<213> ORGANISM: Homo sapiens

<400> SEQUENCE: 99
tttcccagca ctgatcatgg                                            20

<210> SEQ ID NO 100
<211> LENGTH: 20
<212> TYPE: DNA
<213> ORGANISM: Homo sapiens

<400> SEQUENCE: 100
gcctctcgct gtcagacaga                                            20
```

<210> SEQ ID NO 101
<211> LENGTH: 20
<212> TYPE: DNA
<213> ORGANISM: Homo sapiens

<400> SEQUENCE: 101
aagagaggaa ccctctggcg					20

<210> SEQ ID NO 102
<211> LENGTH: 18
<212> TYPE: DNA
<213> ORGANISM: Homo sapiens

<400> SEQUENCE: 102
tggtcctcgc ctgctaca					18

<210> SEQ ID NO 103
<211> LENGTH: 20
<212> TYPE: DNA
<213> ORGANISM: Homo sapiens

<400> SEQUENCE: 103
tggagcaagc tcagaggacc					20

<210> SEQ ID NO 104
<211> LENGTH: 19
<212> TYPE: DNA
<213> ORGANISM: Homo sapiens

<400> SEQUENCE: 104
cctcctttca ggccacatg					19

<210> SEQ ID NO 105
<211> LENGTH: 20
<212> TYPE: DNA
<213> ORGANISM: Homo sapiens

<400> SEQUENCE: 105
ccctcaaact catgcctctg					20

<210> SEQ ID NO 106
<211> LENGTH: 20
<212> TYPE: DNA
<213> ORGANISM: Homo sapiens

<400> SEQUENCE: 106
gctccactcc tggaagcaaa					20

<210> SEQ ID NO 107
<211> LENGTH: 20
<212> TYPE: DNA
<213> ORGANISM: Homo sapiens

<400> SEQUENCE: 107
ttttgcagtc tgcccagttc					20

<210> SEQ ID NO 108
<211> LENGTH: 19
<212> TYPE: DNA
<213> ORGANISM: Homo sapiens

<400> SEQUENCE: 108

```
cctgccgcta aggatagga                                           19

<210> SEQ ID NO 109
<211> LENGTH: 20
<212> TYPE: DNA
<213> ORGANISM: Homo sapiens

<400> SEQUENCE: 109
ggactgctat ttgggcatgc                                          20

<210> SEQ ID NO 110
<211> LENGTH: 20
<212> TYPE: DNA
<213> ORGANISM: Homo sapiens

<400> SEQUENCE: 110
gccggtctgc ttcttgtaaa                                          20

<210> SEQ ID NO 111
<211> LENGTH: 22
<212> TYPE: DNA
<213> ORGANISM: Homo sapiens

<400> SEQUENCE: 111
tggccccgtc ggtccctctg gc                                       22

<210> SEQ ID NO 112
<211> LENGTH: 22
<212> TYPE: DNA
<213> ORGANISM: Homo sapiens

<400> SEQUENCE: 112
tggccccgtc agtccctctg gc                                       22

<210> SEQ ID NO 113
<211> LENGTH: 21
<212> TYPE: DNA
<213> ORGANISM: Homo sapiens

<400> SEQUENCE: 113
gggcctccag ggtccccgtg g                                        21

<210> SEQ ID NO 114
<211> LENGTH: 21
<212> TYPE: DNA
<213> ORGANISM: Homo sapiens

<400> SEQUENCE: 114
gggcctccag agtccccgtg g                                        21

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
cagaaaggag ccagcgcc                                            18

<210> SEQ ID NO 116
<211> LENGTH: 18
<212> TYPE: DNA
```

```
-continued
<213> ORGANISM: Artificial Sequence
<220> FEATURE:
<223> OTHER INFORMATION: Description of Artificial Sequence: Synthetic
      primer

<400> SEQUENCE: 116
ggctaaggtg agagaggg                                                   18
```